US011931422B2

(12) United States Patent
Chao et al.

(10) Patent No.: US 11,931,422 B2
(45) Date of Patent: Mar. 19, 2024

(54) ANTIBODY-UREASE CONJUGATES FOR THERAPEUTIC PURPOSES

(71) Applicant: HELIX BIOPHARMA CORPORATION, Toronto (CA)

(72) Inventors: Heman Chao, Aurora (CA); Wah Yau Wong, Edmonton (CA); Baomin Tian, Edmonton (CA); Kimberly Jayne Gaspar, Saskatoon (CA); Praveen Kumar, Saskatoon (CA)

(73) Assignee: HELIX BIOPHARMA CORPORATION, Toronto (CA)

( * ) Notice: Subject to any disclaimer, the term of this patent is extended or adjusted under 35 U.S.C. 154(b) by 381 days.

(21) Appl. No.: 15/545,549

(22) PCT Filed: Jan. 22, 2016

(86) PCT No.: PCT/IB2016/050342
§ 371 (c)(1),
(2) Date: Jul. 21, 2017

(87) PCT Pub. No.: WO2016/116907
PCT Pub. Date: Jul. 28, 2016

(65) Prior Publication Data

US 2018/0000963 A1 Jan. 4, 2018

Related U.S. Application Data

(60) Provisional application No. 62/107,210, filed on Jan. 23, 2015.

(51) Int. Cl.
*A61K 47/68* (2017.01)
*A61K 39/395* (2006.01)
(Continued)

(52) U.S. Cl.
CPC .... *A61K 47/6815* (2017.08); *A61K 39/39558* (2013.01); *A61K 47/6853* (2017.08);
(Continued)

(58) Field of Classification Search
None
See application file for complete search history.

(56) References Cited

U.S. PATENT DOCUMENTS 4,762,707 A 8/1988 Jansen et al.
7,872,105 B2 * 1/2011 Mackenzie ........ C07K 16/2803 530/388.1

FOREIGN PATENT DOCUMENTS

CA 2130072 A1 2/1996
CA 2492472 1/2004
(Continued)

OTHER PUBLICATIONS

Chao, Drug Development & Delivery, Jan. 2011, vol. 11, No. 1 (Year: 2011).*
(Continued)

*Primary Examiner* — Karl J Puttlitz
(74) *Attorney, Agent, or Firm* — Dinsmore & Shohl LLP

(57) ABSTRACT

Pharmaceutical compositions comprising antibody-urease conjugates and substantially free of unconjugated urease are disclosed. These compositions are prepared by a method that does not require chromatographic purification. These pharmaceutical compositions have utility in the treatment of cancer by antibody-directed enzyme prodrug therapy wherein the urease converts endogenous urea into ammonia in situ to induce cytotoxicity.

26 Claims, 15 Drawing Sheets

Specification includes a Sequence Listing.

A
[Ammonia] μM
0 500 1000 1500 2000 2500 3000
0.0 0.5 1.0 1.5 2.0
[L-DOS47] μg/mL B
% Viability of cells
0 20 40 60 80 100 120
0 1 2 3 4 5 6 7 8
[L-DOS47] μg/mL

(51) Int. Cl.

| | |
|---|---|
| ***C07K 16/28*** | (2006.01) |
| ***C07K 16/30*** | (2006.01) |
| ***C12N 9/80*** | (2006.01) |

(52) U.S. Cl.

CPC ...... *A61K 47/6857* (2017.08); *C07K 16/2803* (2013.01); *C07K 16/30* (2013.01); *C07K 16/3007* (2013.01); *C07K 16/3023* (2013.01); *C12N 9/80* (2013.01); *C07K 2317/22* (2013.01); *C07K 2317/569* (2013.01); *C07K 2317/90* (2013.01); *C07K 2317/92* (2013.01)

(56) References Cited

FOREIGN PATENT DOCUMENTS

| | | | | |
|---|---|---|---|---|
| CA | 2877505 | | * | 12/2013 |
| CA | 2908475 | | * | 10/2014 |
| EP | 0824019 | A1 | | 2/1998 |
| EP | 3261678 | B | | 11/2020 |
| WO | 1991016071 | | | 10/1991 |
| WO | 9715316 | A1 | | 5/1997 |
| WO | 2004009112 | A1 | | 1/2004 |
| WO | 2006032705 | A2 | | 3/2006 |
| WO | 2010106127 | A2 | | 9/2010 |
| WO | 2012066036 | A1 | | 5/2012 |
| WO | 2013185215 | A1 | | 12/2013 |
| WO | 2014165985 | A1 | | 10/2014 |

OTHER PUBLICATIONS

Cheng et al., European Journal of Cancer (2014) 50, 713-721 (Year: 2014).*

Reeck GR, de Haën C, Teller DC, Doolittle RF, Fitch WM, Dickerson RE, et al. (Aug. 1987). "Homology in proteins and nucleic acids: a terminology muddle and a way out of it". Cell. 50 (5): 667. (Year: 1987).*

Holman, Christopher (Jan. 1, 2004). "Protein Similarity Score: A Simplified Version of the Blast Score as a Superior Alternative to Percent Identity for Claiming Genuses of Related Protein Sequences". Santa Clara High Technology Law Journal. 21 (1): 55. ISSN 0882-3383 (Year: 2004).*

Koonin EV (2005). "Orthologs, paralogs, and evolutionary genomics". Annual Review of Genetics. 39: 309-38 (Year: 2005).*

William K. Strohl and Lila M. Strohl, Therapeutic Antibody Engineering, Woodhead Publishing, 2012, p. 375.

HelixBioPharmaCorp. News Release: Helix BioPharma's L-DOS47 to be Highlighted at Pharmaceutical Industry Conference, Oct. 14, 2009.

Baomin Tian et al, "Production and Characterization of a Camelid Single Domain Antibody—Urease Enzyme Conjugate for the Treatment of Cancer"; Bionconjugate Chem., 2015, 26, 1144-1155.

Tsai-Mu Cheng et al, "Single domain antibody against carcinoembryonic antigen-related cell adhesion molecule 6 (CEACAM6) inhibits proliferation, migration, invasion and angiogenesis of pancreatic cancer cells"; European Journal of Cancer (2014) 50, 713-721.

H. Chao et al, "Treating Lung Tumour Through Alkalization"; Helix BioPharma Corporatin, 14th World Conference on Lung Cancer, Jul. 3-7, 2011, Amsterdam, RAI, The Netherlands.

Heman Chao et al, P2.026 Treating Lung Tumour Through Alkalization; 14th World Conference on Lung Cancer, Jun. 2011; Journal of Thoracic Oncology, vol. 6, No. 6, Supplement 2, S935.

Baomin Tian et al, Production and Characterization of a Camelid Single Domain Antibody-Urease Enzyme Conjugate for the Treatment of Cancer; Bioconjugate Chem. 2015, 26, 1144-1155.

Chao, Heman et al, "Development of an alkalizing antibody-enzyme conjugate for NSCLC treatment that is in Phase I clinical testing," AACR Annual Meeting, Helix BioPharma Corp., May 4, 2013.

Chao, Heman, "DOS47—Killing Cancer by Altering the Tumor Microenvironment," Drug Development & Delivery, Jan. 2011, vol. 11, No. 1, pp. 68-72.

"LDOS47: Single Domain Antibody Conjugated Anticancer Therapeutic," BIT's 5th Annual International Congress of Antibodies, Helix BioPharma Corp., 2013.

Wong, Wah Yau et al, "Urease-induced alkalinization of extracellular pH and its antitumor activity in human breast and lung cancers," Journal of Experimental Therapeutics and Oncology, vol. 5, 2005, pp. 93-99.

IPRP for corresponding PCT Application No. PCT/IB2016/050342 dated Apr. 20, 2016.

Chao, et al, "Development of an Alkalizing Antibody-Enzyme Conjugate for NSCLC Treatment that is in Phase I Clinical Testing"; AACR Annual Meeting, Apr. 5, 2013 (Apr. 5, 2013) retrieved from http://helixbiopharma.com/wp-content/uploads/2014/02/Helix-BioPharma-AACR.pdf.

Helix Biopharma, L-DOS47: Single domain antibody conjugated anticancer therapy, BIT's 5th Annual International Congress of Antibodies, 2013. Retrieved from: http://www.helixbiopharma.com/wp-content/uploads/2014/02/LDOS47-ICA-2013-HZ-.pdf.

Chao, DOS47—Killing cancer by altering the tumor microenvironment, Drug Dev. & Del. 11(1): 68-72 (2011).

Chandler et al, "An investigation of the use of urease-antibody conjugates in enzyme immunoassays", Journal of Immunological Methods, Elsevier Science Publishers B.V., Amsterdam, NL. 53(2), 187-194. Sep. 17, 1982.

Sigma: "Anti-Mouse IgG (Whole Molecule) Urease Conjugate", Jan. 6, 2006 from https://www.sigmaaldrich.com/content/dam/sigma-aldrich/docs/Sigma/Datasheet/8/u1004dat.pdf, retrieved on Oct. 22, 2018.

Meyerhoff et al, "Electrode-based enzyme immunoassays using urease conjugates", Analytical Biochemistry, Elsevier, Amsterdam, NL. 95(2), 483-493. Jun. 1, 1979.

Deng et al, "Application of a polyaniline based ammonium sensor for the amperometric immunoassay of a urease conjugated Tal 1 protein", Analytica Chimica Acta, Amsterdam, NL. 461(1), 49-55. Jun. 1, 2002.

Extended European Search Report pertaining to EP Application No. 16739870.0 dated Nov. 11, 2018.

Zhang, et al., A pentavalent single-domain antibody approach to tumor antigen discovery and the development of novel proteomics reagents, J. Mol. Biol. 341:161-9 (2004).

* cited by examiner

Colon Adenocarcinoma

Lung Adenocarcinoma

| | | |
|---|---|---|
| 1 | MDVQL QASGG GVVQP GGSLR LSCAA HDPIF DKNLM GWGRQ APGKQ REYVA | 50 |
| 51 | TISGS GGTNY ASSVE GRFTI SRDNA KKTVY LQMND LKPED TAVYY CNSAF | 100 |
| 101 | AIWGQ GTQVT VSSGG GEEDD GK | 122 |

Residues indicated in red are putative locations for attachment to urease

FIG. 5

ANTIBODY-UREASE CONJUGATES FOR THERAPEUTIC PURPOSES

CROSS REFERENCE TO RELATED APPLICATIONS

This application claims the benefit of the filing date of U.S. Provisional Application No. 62/107,210, filed Jan. 23, 2015. This application is incorporated by reference herein.

SEQUENCE LISTING

The instant application contains a Sequence Listing which has been submitted electronically in ASCII format and is hereby incorporated by reference in its entirety. Said ASCII copy, created on Jan. 14, 2016, is named 105013-1610_SL.txt and is 11,000 bytes in size.

FIELD OF THE INVENTION

This disclosure provides antibody-urease conjugates having therapeutic utility. More specifically, the disclosure relates to therapeutic conjugates having one or more antibodies conjugated to urease, compositions, uses, and preparation thereof.

BACKGROUND

Urease is an enzyme that catalyzes the hydrolysis of urea into carbon dioxide and ammonia. Specifically, urease catalyzes the hydrolysis of urea to produce ammonia and carbamate, the carbamate produced is subsequently degraded by spontaneous hydrolysis to produce another ammonia and carbonic acid. In this regard, urease activity tends to increase the pH of the local environment in which it produces ammonia, which is a basic molecule having general toxicity.

The concept of using antibodies to target tumor associated antigens in the treatment of cancer has been appreciated for some time (Herlyn et. al., (1980) Cancer Research 40, 717). However, as to urease, the toxic component is the alkaline environment produced by enzymatic degradation of urea, and high affinity antibody fragments were employed.

SUMMARY OF THE INVENTION

The present technology is directed to an antibody-urease conjugate. The present technology provides for a pharmaceutical composition comprising a pharmaceutically acceptable aqueous solution suitable for intravenous injection and an antibody-urease conjugate substantially free of urease, free of unconjugated antibody, and/or free of non-aqueous HPLC solvents.

In some aspects, the conjugate has a conjugation ratio of 3, 4, 5, 6, 7, 8, 9, 10, 11, or 12 antibody moieties per urease moiety. In some aspects, the conjugate has a conjugation ratio of about 6 or more antibody moieties per urease moiety. In some aspects, the conjugate has a conjugation ratio of 6, 7, 8, 9, 10, 11, or 12 antibody moieties per urease moiety. In some aspects, the conjugate has a conjugation ratio of 8, 9, 10, 11, or 12 antibody moieties per urease moiety. In some aspects, the conjugate has an average conjugation ratio of about 6 or more antibody moieties per urease moiety. In some aspects, the conjugate has an average conjugation ratio of about 8-11 antibody moieties per urease moiety. In some aspects, the urease is a Jack bean urease.

In some aspects, the antibody is a humanized or non-human antibody. In some aspects, the molecular weight of the antibody is from about 5 kDa to about 200 kDa. In some aspects, the molecular weight of the antibody is from about 5 kDa to about 50 kDa. In some aspects, the antibody is a single domain antibody. In some aspects, the single domain antibody has a size of no more than 110 amino acid residues, or from about 90 to 130 amino acid residues. In some aspects, the molecular weight of the single domain antibody is from about 10 kDa to about 50 kDa. In some aspects, the molecular weight of the single domain antibody is from about 12 kDa to about 15 kDa. In some aspects, the antibody has specificity to an antigen a tumor cell. In some aspects, the antibody has specificity to a tumor antigen expressed by non-small cell lung carcinoma. In some aspects, the antibody has specificity to CEACAM6.

In some aspects, the antibody has a binding affinity to CEACAM6 with a $K_d$ value of higher than about $1\times10^{-6}$ M. In some aspects, the conjugate has a binding affinity to CEACAM6 with a $K_d$ value of no more than about $1\times10^{-8}$ M. In some aspects, the conjugate has a binding affinity to CEACAM6 with a $K_d$ value of no more than about $1\times10^{-10}$ M. In some aspects, the conjugate has a binding affinity to CEACAM6 with an $IC_{50}$ value of no more than about 5 nM. In some aspects, the $IC_{50}$ value is about 3 nM to about 5 nM. In some aspects, the $IC_{50}$ value is about 3.22 nM. In some aspects, the conjugate binds to CEACAM6 with an $IC_{50}$ value of about 10 μg/mL to about 30 μg/mL. In some aspects, the conjugate binds to CEACAM6 with an $IC_{50}$ value of about 20 μg/mL.

In some aspects, the antibody comprises a polypeptide comprising an amino acid sequence of SEQ ID NO. 1. In some aspects, the antibody comprises a polypeptide comprising at least one modification to the amino acid sequence of SEQ ID NO. 1.

The present technology provides for a method of treating cancer in a subject in need thereof, comprising administering to the subject a therapeutically effective amount of the composition provided herein, thereby treating cancer in the subject.

In some aspects, the cancer is one or more of non-small cell lung carcinoma, breast, pancreatic, ovarian, lung, colon cancer, or a combination thereof. In some aspects, the cancer is non-small cell lung carcinoma. In some aspects, the subject is a human.

The present technology provides for a method of preparing a composition comprising an antibody-urease conjugate substantially free of urease, which method comprises combining activated antibody and urease in an aqueous buffer having a pH of about 6.0-7.0, such as about 6.5, adjusting the pH to 8.0-9.0, such as about 8.3 to form the antibody-urease conjugate, and purifying the antibody-urease conjugate, wherein the method does not comprise a chromatographic purification step, such as commonly used chromatographic methods for protein purifications, including size exclusion chromatography (SEC), ion exchange chromatography, affinity chromatography, immobilized metal affinity chromatography, immunoaffinity chromatography, liquid-solid adsorption chromatography, hydrophobic interaction chromatography (HIC), revered phase chromatography (RPC), and high performance liquid chromatography (HPLC), etc. In some aspects, antibody-urease conjugate is purified by ultradiafiltration.

In some aspects, the antibody-urease conjugate has a conjugation ratio of 8-11 antibody moieties per urease moiety. In some aspects, the buffer having a pH of about 6.5 is a sodium acetate buffer. In some aspects, the pH is adjusted to about 8.3 by a method comprising addition of a sodium borate solution.

The present technology provides for a method of increasing antibody binding affinity to a tumor antigen, comprising conjugating a plurality of the antibody molecules to a urease molecule to form an antibody-urease conjugate, wherein the conjugate has a binding affinity to the tumor antigen at least about 100 times higher than the un-conjugated antibody.

In some aspects, the antibody is a humanized or non-human antibody. In some aspects, the antibody is a single domain antibody. In some aspects, the tumor antigen is expressed by non-small cell lung carcinoma. In some aspects, the antibody has specificity to CEACAM6.

The present technology further provides for a kit comprising the composition provided herein and instructions for use of the composition.

These and other aspects of the disclosure are further described below.

BRIEF DESCRIPTION OF THE DRAWINGS

FIG. 5 depicts an amino acid sequence of AFAIKL2 antibody (SEQ ID NO: 1).

probed with anti-AFAIKL2 antibody. Right panel: Western blot of AFAIKL2, urease, and L-DOS47 (standard load and 5× overload) probed with anti-urease antibody. Inset box: magnification of L-DOS47.

Figure 13:
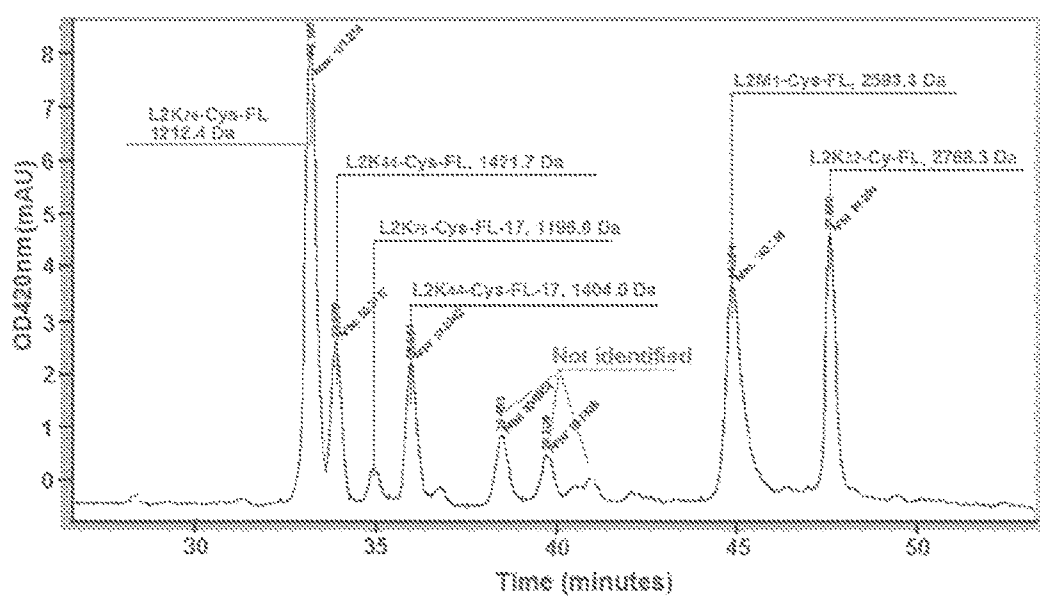

FIG. 13 depicts an exemplifying RP-HPLC chromatogram at 420 nm of a tryptic digest of AFAIKL2-Cys-FL. The identified conjugated peptides and their peptide masses are denoted at the corresponding HPLC peaks.

Figure 14:
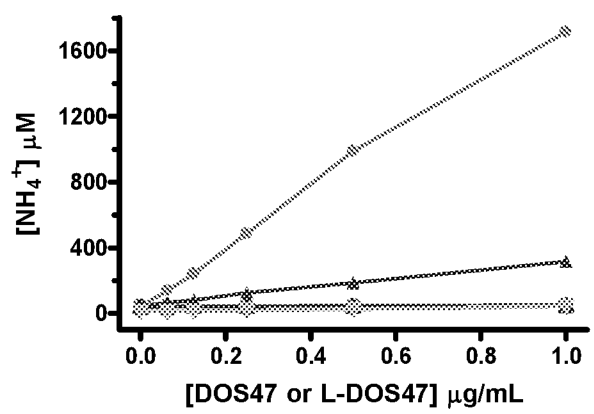

FIG. 14 depicts exemplifying direct binding of L-DOS47 to cancer cell lines BxPC-3, A549, and MCF7. The binding signal was represented by the amount of ammonia generated upon incubation with 20 mM urea. Elevated L-DOS47 binding was observed in BxPC-3 (●), while moderate binding was observed in A549 cells (▲) and no binding was found in MCF7 cells (▼). In addition, no binding was found with the unconjugated DOS47 control in the corresponding cell lines (○, Δ, ∇), suggesting that L-DOS47 binding was specific to BxPC-3 and A549 cells.

Figure 15:
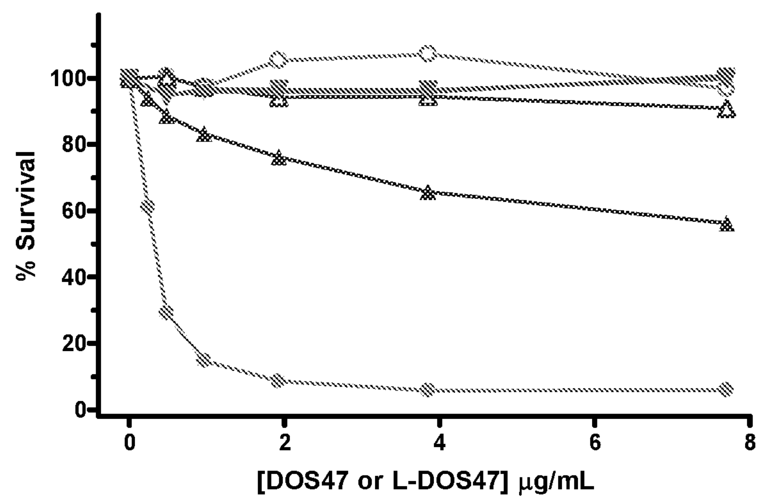

FIG. 15 depicts an example of L-DOS47 induced cytotoxicity on BxPC-3 and A549 cells upon addition of 20 mM urea. No effects were observed in MCF7 cells (▼). BxPC-3 (●) was highly susceptible to L-DOS47, whereas only moderate effects were observed in A549 cells (▲). In addition, no binding was observed with the unconjugated DOS47 control to the corresponding cell lines (○, Δ, ∇). The results of the graphs represent the mean (n=3) of representative experiments. The standard deviation (SD) was less than 10% for all values.

DETAILED DESCRIPTION

It is to be understood that the present disclosure is not limited to particular aspects or embodiments described, as such may, of course, vary. It is also to be understood that the terminology used herein is for the purpose of describing particular aspects or embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

Definitions

It must be noted that as used herein and in the appended claims, the singular forms "a", "an", and "the" include plural referents unless the context clearly dictates otherwise. Thus, for example, reference to "a compound" includes a plurality of compounds.

As used herein, the term "about" when used before a numerical designation, e.g., temperature, time, amount, concentration, and such other, including a range, indicates approximations which may vary by (+) or (−) 10%, 5% or 1% of the stated value.

As used herein, the term "administration" can be effected in one dose, continuously or intermittently or by several sub-doses which in the aggregate provide for a single dose. Dosing can be conducted throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, vaginal, nasal administration, injection, topical application, sublingual, pulmonary, and by suppository.

As used herein, the term "affinity" refers to the strength of binding between receptors and their ligands, for example, between an antibody and its antigen. The term "$K_d$" or "dissociation constant" refers to the affinity between an antibody and an antigen, i.e., how tightly the antibody binds to the particular antigen. The term "$IC_{50}$" or "the half maximal inhibitory concentration" represents the amount of competitor required to cause 50% decrease in binding of the test articles.

As used herein, the term "amino acid" refers to L-amino acid or D-amino acid or a mixture thereof, including both natural amino acid and synthetic amino acid or the like as long as the desired functional property is retained by the polypeptide. $NH_2$, when used at the beginning of a peptide sequence, refers to the free amino group present at the amino terminus (or N-terminus) of a polypeptide. COOH, when used at the end of a peptide sequence, refers to the free carboxy group present at the carboxy terminus (or C-terminus) of a polypeptide. Standard polypeptide abbreviations for amino acid residues are as follows: A (Ala or Alanine); C (Cys or Cysteine); D (Asp or Aspartic Acid); E (Glu or Glutamic Acid); F (Phe or Phenylalanine); G (Gly or Glycine); H (His or Histidine); I (Ile or Isoleucine); K (Lys or Lysine); L (Leu or Leucine); M (Met or Methionine); N (Asn or Asparagine); P (Pro or Proline); Q (Gln or Glutamine); R (Arg or Arginine); S (Ser or Serine); T (Thr or Threonine); V (Val or Valine); W (Trp or Tryptophan); X (Xaa or Unknown or Other); Y (Tyr or Tyrosine); Z (Glx/Gln/Glu or Glutamic Acid/Glutamine); and Dpr (2,3-diaminopropionic acid). All amino acid residue sequences represented herein by formula have a left-to-right orientation in the conventional direction of amino terminus to carboxy terminus. A dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the disclosure. "Consisting of" shall mean excluding more than trace elements of other ingredients and substantial method steps. Embodiments defined by each of these transition terms are within the scope of this disclosure.

As used herein, the terms "active agent", "drug" and "pharmacologically active agent" are used interchangeably herein to refer to a chemical material or compound which, when administered to a subject induces a desired pharmacologic effect, and is intended to include a therapeutic agent, including radionuclides, drugs, anti-cancer agents, toxins and the like. An exemplary active agent is an antibody urease conjugate.

As used herein, the term "antibody" refers to a peptide, polypeptide, or protein that has binding affinity to an antigen. A typical antibody structural unit comprises a tetramer. Each tetramer is composed of two identical pairs of polypeptide chains, each pair having one "light" chain and one "heavy" chain. The N-terminus of each chain defines a variable region of about 100 to 110 or more amino acids primarily responsible for antigen recognition. The terms "variable light chain" (VL) and "variable heavy chain" (VH) refer to these light and heavy chains, respectively. Antibodies exist as intact immunoglobulins or as fragments such as F(ab)'2, a dimer of Fab which itself is a light chain joined to VH-CH1 by a disulfide bond, or an Fab' monomer, which can result from breaking of the disulfide linkage in the hinge region. The Fab' monomer is essentially a Fab with part of the hinge region (see *Fundamental Immunology*, W. E. Paul, ed., Raven Press, N.Y. (1993), for a more detailed description of other antibody fragments). Antibody fragments can be produced by digestion of an intact antibody by, for example, various peeptidases, synthesized de novo either chemically or by utilizing recombinant DNA methodology. Thus, the term "antibody", as used herein, also includes antibody fragments either produced by the modification of antibodies or synthesized de novo using recombinant DNA methodologies. Antibodies include single chain antibodies, including single chain Fv (sFv) antibodies in which a VH and a VL are joined together (directly or through a peptide linker) to form a continuous polypeptide.

As used herein, the term "single domain antibody" (sdAb or "VHH") refers to the single heavy chain variable domain of antibodies of the type and in some aspects can be found in Camelid mammals which are naturally devoid of light chains. In some aspects, the single domain antibody may be derived from a VH region, a VHH region or a VL region. In some aspects, the single domain antibody is of human origin. In some aspects, the human single domain antibody comprises heavy or light chain sequences disclosed in WO2006/099747 and WO2009/079793 and WO2012/100343, incorporated herein by reference in their entirety. In one aspect, the human single domain antibody comprises heavy or light chain sequences with a disulfide bonds within the framework region as discussed in WO2012/100343.

As used herein, the term "antibody fragment" also includes any synthetic or genetically engineered protein that acts like an antibody by binding to a specific antigen to form a complex.

As used herein, the term "conjugate" refers to two or more molecules that are covalently linked to form a larger construct. In one aspect, the two molecules are linked by a direct linkage wherein a reactive functional group on the urease binds to a complementary reactive functional group on the antibody such as an amino functionality of lysine binding to a carboxyl functionality of aspartic or glutamic acid. It being understood, that such reactions may require conventional modification of the carboxyl group to render it more reactive. In another aspect, the two molecules are linked through a linker moiety.

As used herein, the terms "protein", "polypeptide" or "peptide", as used herein, refer interchangeably. The protein has a primary structure represented by its subunit sequence, and may have secondary helical or pleat structures, as well as overall three-dimensional structure. Although "protein" commonly refers to a relatively large polypeptide, e.g., containing 100 or more amino acids, and "peptide" to smaller polypeptides, the terms are used interchangeably herein. That is, the term "protein" may refer to a larger polypeptide, as well as to a smaller peptide, and vice versa.

As used herein, the term "targeting moiety" refers to a molecule that binds to a defined population of cells or selected cell type. The targeting moiety may bind a receptor, an oligonucleotide, an enzymatic substrate, an antigenic determinant, or other binding site present on or in the target cell or cell population. An exemplary targeting moiety is an antibody. Antibody fragments and small peptide sequences capable of recognizing expressed antigens are also contemplated targeting moieties.

As used herein, the terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder.

The terms "subject", "individual" and "patient" are used interchangeably herein to refer to any target of the treatment. Also provided by the present technology is a method of treating tumor cells in situ, or in their normal position or location, for example, neoplastic cells of breast or prostate tumors. These in situ tumors can be located within or on a wide variety of hosts; for example, human to hosts, canine hosts, feline hosts, equine hosts, bovine hosts, porcine hosts, and the like. Any host in which is found a tumor or tumor cells can be treated and is in accordance with the present technology. A subject thus includes a vertebrate, preferably a mammal, more preferably a human.

As used herein, the term "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof. The term "substantially" unless indicated otherwise means greater than about 90%, greater than about 95%, greater than about 96%, greater than about 97%, greater than about 98%, or greater than about 99%. In some embodiments, the composition comprising the antibody-urease conjugates is substantially free of unconjugated urease, meaning that the composition contains greater than about 90% antibody-urease conjugates, greater than about 95% antibody-urease conjugates, greater than about 96% antibody-urease conjugates, greater than about 97% antibody-urease conjugates, greater than about 98% antibody-urease conjugates, or greater than about 99% antibody-urease conjugates. In other words, the composition contains less than about 0.1% unconjugated urease, less than about 0.5% unconjugated urease, less than about 1% unconjugated urease, less than about 2% unconjugated urease, less than about 3% unconjugated urease, less than about 4% unconjugated urease, less than about 5% unconjugated urease, or less than about 10% unconjugated urease. The term "unconjugated urease" refers to an urease without being conjugated to an antibody.

As used herein, the term "urease" refers to an enzyme having the enzymatic activity of a urea amidohydrolase (E.C. 3.5.1.5), either naturally occurring or obtained by, e.g., recombinant nucleic acid techniques and/or chemical synthesis. Urease also includes fusion proteins comprising the entire urease, subunits, or fragments thereof, and/or urease with amino acid substitutions, deletions or additions that preserve the urea amidohydrolase activity of the polypeptide.

As used herein, the term "DOS47" refers to a purified urease.

Antibody-Urease Conjugation

The present technology is directed to an antibody-urease conjugate. The present technology provides for a pharmaceutical composition comprising a pharmaceutically acceptable aqueous solution suitable for intravenous injection and an antibody-urease conjugate substantially free of urease, free of unconjugated antibody, and free of non-aqueous HPLC solvents. Non-aqueous HPLC solvents include organic solvents commonly used in preparative HPLC or HPLC purification, such as methanol, acetonitrile, trifluoroacetic acid, etc. In some aspects, the antibody-urease conjugate is substantially free of phosphate from a phosphate buffer. In some aspects, phosphate buffer containing 10 mM phosphate, 50 mM NaCl pH 7.0 is used for SEC purification. In some aspects, no HPLC purification is performed in the manufacturing production of antibody-urease conjugate.

In some aspects, the conjugate has a conjugation ratio of about 3, 4, 5, 6, 7, 8, 9, 10, 11, 12, 13, 14, 15, 16, 17, 18, 19, or 20 antibody moieties per urease moiety. In some aspects, the conjugate has a conjugation ratio of about 6, 7, 8, 9, 10, 11, or 12 antibody moieties per urease moiety. In some aspects, the conjugate has a conjugation ratio of about 8, 9, 10, 11, or 12 antibody moieties per urease moiety. In some aspects, the conjugate has an average conjugation ratio of about 6 or more antibody moieties per urease moiety. In some aspects, the conjugate has an average conjugation ratio of about 8, 9, 10, or 11 antibody moieties per urease moiety.

In some aspects, the linkage is a covalent bond or direct linkage wherein a reactive functional group on the urease binds to a complementary reactive functional group on the antibody such as an amino ($NH_2$) functionality of e.g., lysine binding to a carboxyl (COOH) functionality of e.g., aspartic or glutamic acid, or a sulfhydryl (SH) of cysteine. It being understood, that such reactions may require conventional modification of the carboxyl group to render it more reactive.

The reactive functionalities can be the same such as oxalic acid, succinic acid, and the like or can be orthogonal functionalities such as amino (which becomes NH after conjugation) and carboxyl (which becomes CO or COO after conjugation) groups. Alternatively, the antibody and/or urease may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting moiety to the active agent, such as antibody to urease. The linker is capable of forming covalent bonds to both the targeting moiety and to the active agent. Suitable linkers are well known to those of skill in the art and include, but are not limited to, straight or branched-chain carbon linkers, heterocyclic carbon linkers, or peptide linkers. Where the targeting moiety and the active agent molecule are polypeptides, the linkers may be joined to the constituent amino acids through their side groups (e.g., through a disulfide linkage to cysteine). In one preferred aspect, the linkers will be joined to the alpha carbon amino and carboxyl groups of the terminal amino acids. In some aspects, the linkage is through a linker having two or more functionalities, such as carboxy or amino, that allow it to react with both the ureases and the antibody. Linkers are well known in the art and typically comprise from 1-20 atoms including carbon, nitrogen, hydrogen, oxygen, sulfur and the like.

A bifunctional linker having one functional group reactive with a group on urease, and another group reactive with an antibody, may be used to form the desired immunoconjugate. Alternatively, derivatization may involve chemical treatment of the targeting moiety, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (see U.S. Pat. No. 4,671,958). Procedures for generation of free sulfhydryl groups on polypeptide, such as antibodies or antibody fragments, are also known (see U.S. Pat. No. 4,659,839).

Other linker molecules and use thereof include those described in, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075).

In some aspects, the linkage is cleavable at or in the vicinity of the target site and the urease is freed from the targeting moiety when the conjugate molecule has reached its target site. Cleaving of the linkage to release the urease from the targeting moiety may be prompted by enzymatic activity or conditions to which the conjugate is subjected either inside the target cell or in the vicinity of the target site. In some aspects, a linker which is cleavable under conditions present at the tumor site (e.g., when exposed to tumor-associated enzymes or acidic pH) may be used.

Cleavable linkers include those described in, e.g., U.S. Pat. Nos. 4,618,492; 4,542,225, and 4,625,014. The mechanisms for release of an active agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In some aspects, a suitable linker is a residue of an amino acid or a peptide spacer consisting of two or more amino acids.

In some aspects, a suitable linker is $R^1$-L-$R^2$, wherein $R^1$ and $R^2$ are the same or different functional groups, one of which is connected to the antibody and the other is connected to urease. $R^1$ and $R^2$ can be independently selected from, but not limited to, —NH—, —CO—, —COO—, —O—, —S—, —NHNH—, —N═N—, ═N—NH—, etc. L can be a straight or branched-hydrocarbon chain, such as an alkyl chain, wherein one or more of the carbons are optionally replaced with oxygen, nitrogen, amide, sulfur, sulfoxide, sulfone, cycloalkyl, heterocycloalkyl, aryl, heteroaryl, etc. In some aspects, the linker can be an amino acid residue or a peptide. In some circumstances, the linker is cleavable by an enzyme or change in pH at or approximate to the target site. Certain linkers and procedures suitable for preparing conjugates are described in U.S. Pat. Nos. 4,414,148, 4,545,985, 4,569,789, 4,671,958, 4,659,839, 4,680,338, 4,699,784, 4,894,443, and 6,521,431. In some aspects, the linker is

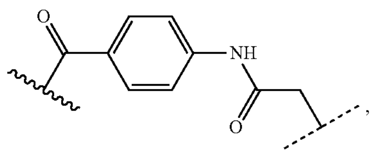

wherein ∿∿ and ----- represents the points of connection to the antibody or urease. In some aspect, ∿∿ represents the point of connection to an amino group of an antibody and ----- represents the point of connection to a S atom of a thio group of urease. This linker is the residue of using the linking agent SIAB (N-succinimidyl(4-iodoacetyl)amino-benzoate) to conjugate the antibody and urease. In some aspects, ultrapurification is the separation method suitable for the conjugation method using SIAB as the cross linking agent.

In some aspects, the linker is the residue of using a linking agent of the formula:

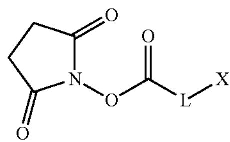

wherein X is bromo or iodo, and L is the linker as described herein.

In some aspects, the linking agent is SBAP (succinimidyl 3-[bromoacetamino]propionate) or SIA (N-succinimidyl iodoacetate), which can be used for the conjugation under the similar conditions (e.g., no HPLC chromatographic purification is needed and only ultrafiltration may be needed) as that of SIAB. In some aspects, the linkage arm length of SIAB (10.6 Anstrong) is more suitable/reflexable than that of SBAP (6.2 Å) and SIA (1.5 Å). In some aspects, the linking agent is SPDP (succinimidyl 3-(pyridyldithio) propionate), SMPT (succinimidyloxycarbonyl-methyl-(2-pyridldithio) toluene) or SMCC (succinimidyl 4-(N-maleimidomethyl) cyclohexane-carboxylate), which can be used for the conjugation, but more than one separation methods such as IEC and ethanol fractionation may be need to separate unreacted urease from the conjugation reaction solution with lower yield.

Even further, additional components, such as but not limited to, therapeutic agents such as anti-cancer agents can also be bound to the antibodies to further enhance the therapeutic effect.

Urease

A number of studies have provided detailed information about the genetics of ureases from a variety of evolutionarily diverse bacteria, plants, fungi and viruses (Mobley, H. L. T. et al. (1995) Microbiol. Rev. 59: 451-480; Eur J. Biochem., 175, 151-165 (1988); Labigne, A. (1990) International publication No. WO 90/04030; Clayton, C. L. et al. (1990) Nucleic Acid Res. 18, 362; and U.S. Pat. Nos. 6,248,330 and 5,298,399, each of which is incorporated herein by reference). Of particular interest is urease that is found in plants (Sirko, A. and Brodzik, R. (2000) Acta Biochim Pol 47(4): 1189-95). One exemplary plant urease is jack bean urease. Other useful urease sequences may be identified in public databases, e.g., Entrez (ncbi.nlm.nih.gov/Entrez).

In some aspects, the urease is a Jack bean urease. The jack bean urease has an amino acid sequence of SEQ ID NO. 2, as shown below:

```
                                          (SEQ ID No. 2)
MKLSPREVEKLGLHNAGYLAQKRLARGVRLNYTEAVALIASQ

IMEYARDGEKTVAQLMCLGQHLLGRRQVLPAVPHLLNAVQVE

ATFPDGTKLVTVHDPISRENGELQEALFGSLLPVPSLDKFAE

TKEDNRIPGEILCEDECLTLNIGRKAVILKVTSKGDRPIQVG

SHYHFIEVNPYLTFDRRKAYGMRLNIAAGTAVRFEPGDCKSV

TLVSIEGNKVIRGGNAIADGPVNETNLEAAMHAVRSKGFGHE

EEKDASEGFTKEDPNCPFNTFIHRKEYANKYGPTTGDKIRLG

DTNLLAEIEKDYALYGDECVFGGGKVIRDGMGQSCGHPPAIS

LDTVITNAVIIDYTGIIKADIGIKDGLIASIGKAGNPDIMNG

VFSNMIIGANTEVIAGEGLIVTAGAIDCHVHYICPQLVYEAI

SSGITTLVGGGTGPAAGTRATTCTPSPTQMRLMLQSTDDLPL

NFGFTGKGSSSKPDELHEIIKAGAMGLKLHEDWGSTPAAIDN

CLTIAEHHDIQINIHTDTLNEAGFVEHSIAAFKGRTIHTYHS

EGAGGGHAPDIIKVCGIKNVLPSSTNPTRPLTSNTIDEHLDM

LMVCHHLDREIPEDLAFAHSRIRKKTIAAEDVLNDIGAISII

SSDSQAMGRVGEVISRTWQTADKMKAQTGPLKCDSSDNDNFR

IRRYIAKYTINPAIANGFSQYVGSVEVGKLADLVMWKPSFFG

TKPEMVIKGGMVAWADIGDPNASIPTPEPVKMRPMYGTLGKA

GGALSIAFVSKAALDQRVNVLYGLNKRVEAVSNVRKLTKLDM

KLNDALPEITVDPESYTVKADGKLLCVSEATTVPLSRNYFLF
```

Useful urease sequences may be identified in public databases, e.g., Entrez (http://www.ncbi.nlm.nih.gov/Entrez/). Additionally, primers that are useful for amplifying ureases from a wide variety of organisms may be utilized as described by Baker, K. M. and Collier, J. L. (http://www.science.smith.eduklepartments/Biology/lkatz/NEMEBwebpage/abstracts.html) or using the CODEHOP (COnsensus-DEgenerate Hybrid Oligonucleotide Primer) as described in Rose, et al. (1998) *Nucl. Acids Res.* 26:1628.

Urease can convert the substrate urea to ammonia and carbamate. This enzymatic activity may increase the pH making the environment more basic. The environment around a cancer cell is typically acidic (Webb, S. D., et al. (2001) *Novartis Found Symp* 240:169-81. Thus, by raising the pH of the extracellular environment in this manner, growth of the cancer cell is inhibited. Accordingly, addition of the antibody-urease conjugates in certain aspects of the present technology causes the pH of the interstitial fluid to be raised by about 0.1 pH unit, e.g., 0.1-0.5 pH units or greater.

The urease of the present technology includes the naturally occurring forms of urease as well as functionally active variants thereof. Two general types of amino acid sequence variants are contemplated. Amino acid sequence variants are those having one or more substitutions in specific amino acids which do not destroy the urease activity. These variants include silent variants and conservatively modified variants which are substantially homologous and functionally equivalent to the native protein. A variant of a native protein is "substantially homologous" to the native protein when at least about 80%, more preferably at least about 90%, even more preferably at least about 95%, yet even more preferably 98%, and most preferably at least about 99% of its amino acid sequence is identical to the amino acid sequence of the native protein. A variant may differ by as few as 1 or up to 10 or more amino acids.

A second type of variant includes size variants of urease which are isolated active fragments of urease. Size variants may be formed by, e.g., fragmenting urease, by chemical modification, by proteolytic enzyme digestion, or by combinations thereof. Additionally, genetic engineering techniques, as well as methods of synthesizing polypeptides directly from amino acid residues, can be employed to produce size variants.

By "functionally equivalent" is intended that the sequence of the variant defines a chain that produces a protein having substantially the same biological activity as the native urease. Such functionally equivalent variants that comprise substantial sequence variations are also encompassed by the present technology. Thus, a functionally equivalent variant of the native urease protein will have a sufficient biological activity to be therapeutically useful. Methods are available in the art for determining functional equivalence. Biological activity can be measured using assays specifically designed for measuring activity of the native urease protein. Additionally, antibodies raised against the biologically active native protein can be tested for their ability to bind to the functionally equivalent variant, where effective binding is indicative of a protein having a conformation similar to that of the native protein.

The urease protein sequences of the present technology, including conservatively substituted sequences, can be present as part of larger polypeptide sequences such as occur upon the addition of one or more domains for purification of the protein (e.g., poly His segments, FLAG tag segments, etc.), where the additional functional domains have little or no effect on the activity of the urease protein portion of the protein, or where the additional domains can be removed by post synthesis processing steps, such as by treatment with a protease.

The addition of one or more nucleic acids or sequences that do not alter the encoded activity of a nucleic acid molecule of the present technology, such as the addition of a non-functional sequence, is a conservative variation of the basic nucleic acid molecule, and the addition of one or more amino acid residues that do not alter the activity of a polypeptide of the present technology is a conservative variation of the basic polypeptide. Both such types of additions are features of the present technology. One of ordinary skill in the art will appreciate that many conservative variations of the nucleic acid constructs which are disclosed yield a functionally identical construct.

A variety of methods of determining sequence relationships can be used, including manual alignment, and computer assisted sequence alignment and analysis. This later approach is a preferred approach in the present technology, due to the increased throughput afforded by computer-assisted methods. A variety of computer programs for performing sequence alignment are available, or can be produced by one of skill.

As noted above, the sequences of the nucleic acids and polypeptides (and fragments thereof) employed in the present technology need not be identical, but can be substantially identical (or substantially similar), to the corresponding sequence of a urease polypeptide or nucleic acid molecule (or fragment thereof) of the present technology or related molecule. For example, the polypeptides can be subject to various changes, such as one or more amino acid or nucleic acid insertions, deletions, and substitutions, either conservative or non-conservative, including where, e.g., such changes might provide for certain advantages in their use, e.g., in their therapeutic or administration application.

Targeting Moieties

Targeting moieties are contemplated as chemical entities of the present technology, and bind to a defined, selected cell type or target cell population, such as cancer cells. Targeting moieties useful in this regard include antibodies and antibody fragments, peptides, and hormones. Proteins corresponding to known cell surface receptors (including low density lipoproteins, transferrin and insulin), fibrinolytic enzymes, platelet binding proteins such as annexins, and biological response modifiers (including interleukin, interferon, erythropoietin and colony-stimulating factor) are also contemplated targeting moieties. Oligonucleotides, e.g., antisense oligonucleotides that are complementary to a portion of a target cell nucleic acid, may be used as targeting moieties in the present technology. Targeting moieties may also be oligonucleotides that bind to a target cell surface. Analogs of the above-listed targeting moieties that retain the ability to bind to a defined target cell population may also be used as targeting moieties.

Functional equivalents of the aforementioned targeting moieties are also useful as targeting moieties of the present technology. An exemplary targeting moiety functional equivalent is an organic chemical construct designed to mimic the proper configuration and/or orientation for targeting moiety target cell binding. Another targeting moiety functional equivalent is a short polypeptide that exhibits the binding affinity of the targeting moiety.

In some aspects, the targeting moieties of the present disclosure are antibodies, peptides, oligonucleotides or the like, that are reactive with an antigen on the surface of a target cell. Both polyclonal and monoclonal antibodies which are either available commercially or described in the literature may be employed. The antibodies may be whole antibodies or fragments thereof. Monoclonal antibodies and fragments may be produced in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species.

In some aspects, the targeting moiety is a humanized or non-human antibody. In some aspects, the targeting moiety is a single domain antibody. In some aspects, the single domain antibody (sdAb) or "VHH" refers to the single heavy chain variable domain of antibodies of the type that can be found in Camelid mammals which are naturally devoid of light chains. In some aspects, the single domain antibody may be derived from a VH region, a VHH region or a VL region. In some aspects, the single domain antibody is of human origin. In some aspects, the human single domain antibody comprises heavy or light chain sequences disclosed in WO2006/099747 and WO2009/079793 and WO2012/100343, incorporated herein by reference in their entirety. In one aspect, the human single domain antibody comprises heavy or light chain sequences with a disulfide bonds within the framework region as discussed in WO2012/100343.

In some aspects, the targeting moiety (e.g., antibody) has specificity to a tumor antigen expressed by carcinomas, leukemias, lymphomas, and sarcomas. Carcinomas may be of the anus, biliary tract, bladder, breast, colon, rectum, lung, oropharynx, hypopharynx, esophagus, stomach, pancreas, liver, kidney, gallbladder and bile ducts, small intestine, urinary tract, ovarian, colon, non-small cell lung carcinoma, genital tract, endocrine glands, thyroid, and skin. In some aspects, the targeting moiety (e.g., antibody) has specificity to a tumor antigen expressed by carcinoid tumors, gastrointestinal stromal tumors, head and neck tumors, primary tumors, hemangiomas, melanomas, malignant mesothelioma, multiple myeloma, and tumors of the brain, nerves, eyes, and meninges. In some aspects, the targeting moiety (e.g., antibody) has specificity to a tumor antigen expressed by carcinoma, breast, pancreatic, ovarian, lung, and colon cancer. In some aspects, the targeting moiety (e.g., antibody) has specificity to a tumor antigen expressed by non-small cell lung carcinoma.

In some aspects, the antibody has specificity to a tumor antigen expressed by non-small cell lung carcinoma. In some aspects, the tumor antigen expressed by non-small cell lung carcinoma is CEACAM6 (carcinoembryonic antigen-related cell adhesion molecule 6), and the antibody has specificity to CEACAM6. CEACAM6, also known as non-specific cross-reacting antigen (NCA) or CD66c, is a well characterized cancer antigen (11, 12). It shares high sequence homology with other human carcinoembryonic antigens such CEACAM1, CEACAM7, and CEACAM8. It is a glycosylphosphoinositol (GPI)-linked cell surface protein but with no known cytoplasmic domain. CEACAM6 expression is significantly elevated in breast, pancreatic, ovarian, lung, and colon cancer tissues. Its increased expression is implicated in the invasive and metastatic behavior of tumor cells (13). In some aspects, the antibody has a binding affinity to CEACAM6 with a $K_d$ value of higher than about $1\times10^{-6}$ M. In some aspects, the conjugate has a binding affinity to CEACAM6 with a $K_d$ value of no more than about $1\times10^{-8}$ M, $1\times10^{-9}$ M, $1\times10^{-10}$ M, or $1\times10^{-20}$ M. In some aspects, the antibody is a single-domain camelid antibody fragment (AFAIKL2, SEQ ID NO. 1) that recognizes CEACAM6 on lung adenocarcinoma cells. In some aspects, the antibody comprises a polypeptide comprising an amino acid sequence of SEQ ID NO. 1 as shown in FIG. 5. In some aspects, the antibody comprises a polypeptide comprising at least one modification to the amino acid sequence of SEQ ID NO. 1. In some aspects, the antibody comprises a polypeptide comprising at least 80%, 85%, 90%, 95%, 98% and 99% of sequence homology to the amino acid sequence of SEQ ID NO. 1.

In some aspects, CEACAM6 antibody is an anti-CEACAM6 antibody (9A6): sc-59899 available from Santa Cruz Biotech. CEACAM6 Antibody (9A6) is a mouse monoclonal IgG1 provided at 200 μg/ml, which is raised against CEACAM6-expressing tumor cell lines of human origin. It is recommended for detection of CEACAM6 of human origin.

In some aspects, CEACAM6 antibody is an anti-CEACAM6 antibody (ab56234) available from abcam. The anti-CEACAM6 antibody (ab56234) is a rabbit polyclonal to CEACAM6. It was raised against a region within synthetic peptide (IQNPASANRS DPVTLNVLYG PDGPTISPSK ANYRPGENLN LSCHAASNPP (SEQ ID NO: 3)), which corresponds to internal sequence amino acids 217-266 of human CEACAM6.

In some aspects, CEACAM6 antibody is an anti-CEACAM-6/CD66c antibody available from Novus Biologicals, which is a rabbit polyclonal antibody against CEACAM6 and was validated on Western Blot and immunohistochemistry-P. It was raised against synthetic peptide (EIQNPASANRSD (SEQ ID NO: 4)) directed towards the middle region of human CEACAM6 (NP_002474).

In some aspects, CEACAM6 antibody is an anti-CEACAM6 Antibody EPR4403 available from OriGene, which is a rabbit monoclonal antibody against CEACAM6 (clone EPR4403). It was raised against a synthetic peptide corresponding to residues in human CEACAM6. It has reactivity to mouse, rat, and human CEACAM6.

In some aspects, the conjugate has a binding affinity to CEACAM6 with an $IC_{50}$ value of no more than about 10 nM. In some aspects, the conjugate has a binding affinity to CEACAM6 with an $IC_{50}$ value of no more than about 5 nM. In some aspects, the conjugate has a binding affinity to CEACAM6 with an $IC_{50}$ value of no more than about 4 nM. In some aspects, the $IC_{50}$ value is about 3.22 nM. In some aspects, the conjugate binds to CEACAM6 with an $IC_{50}$ value of about 10-30 μg/mL. In some aspects, the conjugate binds to CEACAM6 with an $IC_{50}$ value of about 20 μg/mL. The binding affinity of an antibody or a conjugate to a target antigen can be determined according to methods described herein or known in the art. In some aspects, the present technology describes this anti-CEACAM6-urease conjugate (L-DOS47). In some aspects, the present technology describes an antibody-urease conjugate, e.g., AFAIKL2-urease. A phage library derived from the heavy chain antibody repertoire of a llama is used to identify a single-domain antibody (sdAb) by panning against the non-small cell lung adenocarcinoma A549. The sdAb is designated AFAI. The gene sequence of AFAI is optimized for conjugation purpose and renamed as AFAIKL2. In some aspects, the AFAIKL2 antibody is cloned and expressed in *E. coli* BL21 (DE3) pT7-7 system.

Humanized targeting moieties are capable of decreasing the immunoreactivity of the antibody or polypeptide in the host recipient, permitting an increase in the half-life and a reduction in adverse immune reactions. Murine monoclonal antibodies may be humanized by, e.g., genetically recombining the nucleotide sequence encoding the murine Fv region or the complementarity determining regions thereof with the nucleotide sequence encoding a human constant domain region and an Fc region. Murine residues may also be retained within the human variable region framework domains to ensure proper target site binding characteristics. Genetically engineered antibodies for delivery of various active agents to cancer cells is reviewed in Bodey, B. (2001) *Expert Opin Biol. Ther.* 1(4):603-17.

In some aspects, the targeting moiety is a ligand which is reactive with a receptor on the surface of the target cell. Thus, the targeting moiety may include without limitation hormones with affinity for a cellular binding component, any molecule containing a carbohydrate moiety recognized by a cellular binding component and drugs or small molecules that bind to a cellular binding component. The phrase "binding component" includes both receptor and acceptor molecules. Preferably, the binding component is a cell-surface binding component. In one aspect, the targeting moiety is a naturally occurring protein, such as insulin, that binds to a target site. Cytokines, including interleukins and factors such as granulocyte/macrophage colony stimulating factor (GM-CSF) and tumor necrosis factor (TNF) are also specific targeting moieties, known to bind to specific cells expressing high levels of their receptors (Terlikowski, S J (2002) *Toxicology* 174(3):143-152).

In order to decrease urease or other active agent exposure to non-target cells or tissues, targeting moieties may be screened to identify those that display minimal non-target reactivity, while retaining target specificity and reactivity. By reducing non-target exposure (and adverse non-target localization and/or toxicity), increased doses of urease or other active agent may be administered. This allows the administration of the highest possible concentration of urease or other therapeutic agent in order to maximize exposure of target cells, while remaining below the threshold of unacceptable non-target cell toxicity.

In some aspects, two or more active agent-targeting moiety conjugates are employed, wherein each conjugate includes a different targeting moiety, e.g., a different antibody species. Each of the utilized targeting moieties binds to a different target site region that may be associated with the same or a different target site. The active agent component of each administered conjugate may be the same or different. See, e.g., U.S. Pat. Nos. 4,867,962 and 5,976,535, each of which are incorporated by reference herein. In some aspects, the target site accretion of active agent conjugate to the target site is improved, because each targeting moiety, e.g., antibody species, recognizes a different target site region (i.e., epitope). This alternative target site region approach provides more potential target site binding points for the active agent. Consequently, actual or effective target site saturation, e.g., via epitope saturation and/or steric hindrance, may be avoided. Thus, additive accumulation of active agent, e.g., urease, may be accomplished. Alternatively, or in combination, additional urease specific gene products may be employed as active agents, e.g., for the production of a catalytically active holoenzyme at the target site. An exemplary urease apoenzyme includes the gamma, beta and alpha subunits encoded by the bacterial ureABC genes (Burne, R. A. and Chen, Y. M. (2000) *Microbes and Infection* 2:533-542).

The patterns of cross-reactivity for monoclonal antibodies directed against a particular target site may be analyzed to identify a set of two or more target-specific monoclonal antibodies with non-overlapping cross-reactivity for use in a therapeutic application. The phrase "non-overlapping patterns of cross-reactivity" indicates that the non-target tissues bound by one antibody species differs substantially from the non-target tissues bound by another antibody species. The patterns of cross-reactivity differ to the extent necessary to proportionately reduce the exposure of active agent for therapeutic applications. Less antibody pair (or larger set of antibodies) overlap is preferred.

Antibodies may be screened by a variety of methods. Immunohistochemical analysis may be employed to determine reactivity with target tissue and cross-reactivity with non-target tissue. Tissues to which the antibody species bind may be identified by exposing the tissue to the antibody; washing the tissue to remove any unbound antibody; and detecting the presence of bound antibody. In vitro histochemical procedures are known in the art. See, e.g., Sanchez-Islas, E. and Leon-Olea, M. (2001) *Nitric Oxide* 5(4): 302-16.

Where the targeting moiety is relatively short, it may be synthesized using standard chemical peptide synthesis techniques. Solid phase synthesis in which the C-terminal amino acid of the sequence is attached to an insoluble support followed by sequential addition of the remaining amino acids in the sequence is contemplated for one aspect for the method for the chemical synthesis of the polypeptides. Techniques for solid phase synthesis are described by Barany and Merrifield, *Solid-Phase Peptide Synthesis*; pp. 3-284 in *The Peptides: Analysis, Synthesis, Biology*. Vol. 2: *Special Methods in Peptide Synthesis, Part A*., Merrifield, et al. *J. Am. Chem. Soc.,* 85: 2149-2156 (1963), and Stewart et al., *Solid Phase Peptide Synthesis,* 2nd ed. Pierce Chem. Co., Rockford, III. (1984).

DNA encoding the antibody or urease may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

Methods of Preparing Antibody-Urease Conjugates

The present technology provides for a method of preparing a composition comprising an antibody-urease conjugate and substantially free of unconjugated urease, such as no more than about 5%, 4%, 3%, 2%, or 1% of urease based on the weight of the antibody-urease conjugate, which method comprises (1) combining the activated antibody and urease in a solvent in which the activated antibody and urease substantially do not react, such as no more than 10%, 5% or 1% reaction per hour, to form a reaction mixture wherein the distribution of the activated antibody and urease in the solvent is uniform, and (2) altering a property of the mixture of (1) such that the activated antibody readily react with the urease to form the antibody-urease conjugate. In some aspects, the property of the mixture of (1) is the pH value. In some aspects, the altering the property of the mixture of (1) comprises increase the pH to a value that the activated antibody readily react with the urease to form the antibody-urease conjugate. In some aspects, the activated antibody readily, e.g., at least 90% or at least 95% of activated antibody, react with the urease in (2) at a rate that the mixture is substantially free of unconjugated urease about 6 hours, about 5 hours, about 4 hours, about 3 hours, about 2 hours, or about 1 hour after the property of the mixture is altered.

In some aspects, the method comprises combining activated antibody and urease in an acidic aqueous buffer having a pH of about 6.0-7.0, such as about 6.5, adjusting the pH to basic pH of about 8.0-9.0, such as about 8.3 to form the antibody-urease conjugate, and purifying the antibody-urease conjugate by ultradiafiltration, wherein the method does not comprise a chromatographic purification step. In some aspects, the aqueous buffer having a pH of about 5 to 8. In some aspects, the activated antibody and urease are combined in the acidic aqueous buffer. In some aspects, the ratio of activated antibody and urease is from about 3 to about 12. In some aspects, the antibody-urease conjugate has a conjugation ratio of 6-15 antibody moieties per urease moiety. In some aspects, the antibody-urease conjugate has a conjugation ratio of 8-11 antibody moieties per urease moiety. In some aspects, the pH adjuster is a buffer agent or a buffer solution. In some aspects, the pH adjuster comprises one or more of hydrochloric acid, sulfuric acid, nitric acid, boric acid, carbonic acid, bicarbonic acid, gluconic acid, sodium hydroxide, potassium hydroxide, aqueous ammonia, citric acid, monoethanolamine, lactic acid, acetic acid, succinic acid, fumaric acid, maleic acid, phosphoric acid, methanesulfonic acid, malic acid, propionic acid, trifluoroacetic acid, a salt thereof, or a combination thereof. In some aspects, the buffer agent comprises one or more of glycin, acetic acid, citric acid, boric acid, phthalic acid, phosphoric acid, succinic acid, lactic acid, tartaric acid, carbonic acid, hydrochloric acid, sodium hydroxide, a salt thereof, or a combination thereof. In some aspects, the buffer solution comprises one or more of glycine hydrochloride buffer, acetate buffer, citrate buffer, lactate buffer, phosphate buffer, citric acid-phosphate buffer, phosphate-acetate-borate buffer, phthalate buffer, or a combination thereof. In some aspects, the buffer is not a phosphate buffer. In some aspects, the acidic buffer is a sodium acetate buffer. In some aspects, the pH is adjusted to the basic pH by a method comprising addition of an aqueous base solution such as a sodium borate solution (e.g., 0.1-5 M, or 1M). Without wishing to be bound by a theory, sodium acetate buffer has low buffer capacity, and is suitable for adjusting the pH to 8.3 by pH 8.5, 1M borate buffer. In some aspects, Tris-HCl buffer (e.g., 1M Tris-HCl) is used to adjust the mixture to pH 8-9, e.g., 8.3.

In some aspects, the reaction times and the antibody/urease ratio are kept as constants. In some aspects, the molar ratio of antibody/urease in the reaction mixture is about 25 or about 21, or about 1.8 to 12 antibodies/urease. In some aspects, the antibody/urease molar ratio is adjusted from 4 to 25. In some aspects, the antibody/urease molar ratio at least 6.

In some aspects, no more than 1% or 2% of unreacted antibody is present in the mixture after purification such as ultradiafiltration. In some aspects, other non-HPLC purification methods can be used. For example, ethanol crystallization/fractionation can be used for purification with lower yield. In some aspects, the molecular weight of the antibody is no more than 50 kDa, such as about 10-20 kDa, or about 13 kDa, and the purification is ultradiafiltration. In some aspects, the method provides the antibody-urease conjugate in a yield of at least about 60% of total protein by weight, about 70% of total protein by weight, about 80% of total protein by weight, or at least 90% of total protein by weight. Total protein means the combined amount (in weight) of urease and AFAIKL2 antibody. In some aspects, no more than 10-20% (by total protein weight) of unconjugated antibody remains in the reaction mixture before purification.

The present technology provides for a stable composition comprising an activated antibody and urease in an acidic aqueous solvent (as described above) and substantially free of antibody-urease conjugate, such as no more than about 5%, 4%, 3%, 2%, or 1% of antibody-urease conjugate based on the weight of urease. The present technology further provides for a composition comprising an antibody-urease conjugate and substantially free of unconjugated urease, such as no more than about 5%, 4%, 3%, 2%, or 1% of urease based on the weight of the antibody-urease conjugate in an aqueous solvent, wherein the aqueous solvent has a pH of about 8-9, e.g., 8.3 (as described above). In some aspects, the composition comprising the antibody-urease conjugate further comprises no more than about 40 to 60% unconjugated antibody by total antibody (activated antibody and unreacted antibody). In some aspects, the composition comprising the antibody-urease conjugate further comprises no more than about 10 to 20% unconjugated antibody by total proteins.

Since urease causes release of ammonia in vivo which has general toxicity and itself does not target tumors, the presence of unconjugated urease increases the risk of urease being present in and producing toxicity to normal tissues. However, due to the size and other properties of urease, the conjugation of antibodies to the urease does not result in sufficient size or other differentials to allow ready separation of the antibody-urease conjugate from unconjugated urease by chromatographic purification methods, especially in a large scale.

The present technology surprisingly provides substantially complete conjugation of urease with antibodies, such that the resulting product is substantially free of unconjugated urease without any chromatographic purification. By substantially free of urease, the compositions described herein delivers substantially all of urease moieties in the composition to the target site through systemic administration. The target delivery of urease to the target site reduces or eliminates the general toxicity of ammonia produced by urease and reduces the amount of urease that needs to be administered in order to produce therapeutic effect. The present technology is especially suitable for preparing in a large scale, such as at least about 1 g, 10 g, 100 g, or 1 kg, the antibody-urease conjugate that is substantially free of urease for clinical uses, in particular for treating metastatic tumors which are difficult or impractical to be treated by local administration of urease.

The present technology also provides for a method of increasing antibody binding affinity to a tumor antigen, comprising conjugating a plurality of the antibody molecules to a urease molecule to form an antibody-urease conjugate, wherein the conjugate has a binding affinity to the tumor antigen at least about 100 times, such as about 200 times, about 300 times, about 400 times, and about 500 times, higher than the un-conjugated antibody. In some aspects, competitive binding assay shows that the binding affinity of the antibody-urease conjugate is about 100 times, about 200 times, about 300 times, about 400 times, and about 500 times stronger than that of the native single domain antibody due to increased avidity. In some aspects, the conjugate has a conjugation ratio of 3, 4, 5, 6, 7, 8, 9, 10, 11, or 12 antibody moieties per urease moiety. In some aspects, the conjugate has a conjugation ratio of about 6 or more antibody moieties per urease moiety. In some aspects, the conjugate has a conjugation ratio of 6, 7, 8, 9, 10, 11, or 12 antibody moieties per urease moiety. In some aspects, the conjugate has a conjugation ratio of 8, 9, 10, or 11 antibody moieties per urease moiety. In some aspects, the conjugate has an average conjugation ratio of about 8, 9, 10, or 11 antibody moieties per urease moiety. In some aspects, the urease is a Jack bean urease. In some aspects, the antibody is a humanized or non-human antibody. In some aspects, the antibody is a single domain antibody. In some aspects, the tumor antigen is expressed by non-small cell lung carcinoma. In some aspects, the antibody has specificity to CEACAM6. In some aspects, the antibody has a binding affinity to CEACAM6 with a $K_d$ value of higher than about $1\times10^{-6}$ M. In some aspects, the conjugate binds to CEACAM6 with a $K_d$ value of no more than about $1\times10^{-8}$ M. In some aspects, the conjugate binds to CEACAM6 with a $K_d$ value of no more than about $1\times10^{-10}$ M. In some aspects, the conjugate binds to CEACAM6 with an $IC_{50}$ value of no more than about 5 nM. In some aspects, the $IC_{50}$ value is about 3.22 nM. In some aspects, the conjugate binds to CEACAM6 with an $IC_{50}$ value of about 20 μg/mL. CEACAM6, also known as non-specific cross-reacting antigen (NCA) or CD66c, is a well characterized cancer antigen. It shares high sequence homology with other human carcinoembryonic antigens such CEACAM1, CEACAM7, and CEACAM8. It is a glycosylphosphoinositol (GPI)-linked cell surface protein but with no known cytoplasmic domain. CEACAM6 expression is significantly elevated in breast, pancreatic, ovarian, lung, and colon cancer tissues.

Composition Formulations

The compositions of the present technology comprise an antibody-urease conjugate substantially free of urease and optionally free of non-aqueous HPLC solvents. In some aspects, the composition is a pharmaceutically acceptable composition. The composition may further comprise a biocompatible pharmaceutical carrier, adjuvant, or vehicle. In some aspects, the composition is in a solid form. In some aspects, the composition is in an aqueous solution comprising about 0.1-10 mg/mL, about 0.5-5 mg/mL, about 1-5 mg/mL, or about 1.5-2.0 mg/mL conjugate. In some aspects, the aqueous solution further comprises an excipient such as one or more of histidine, sucrose, and EDTA. In some aspects, the aqueous solution comprises about 1-20 mM such as 10 mM histidine, about 0.1-5 w/v % such as 1 w/v % sucrose, about 0.1-0.5 mM such as 0.2 mM EDTA. In some aspects, the aqueous solution has a pH of about 6.5 to 7, such as about 6.8. In some aspects, the aqueous solution does not contain phosphate. In some aspects, the composition is a solid form obtained by lyophilization of the aqueous solution. In some aspects, the solid form does not contain phosphate.

The composition may also include other nucleotide sequences, polypeptides, drugs, or hormones mixed with excipient(s) or other pharmaceutically acceptable carriers. Compositions other than pharmaceutical compositions optionally comprise liquid, i.e., water or a water-based liquid.

Pharmaceutically acceptable excipients to be added to pharmaceutical compositions also are well-known to those who are skilled in the art, and are readily available. The choice of excipient will be determined in part by the particular method used to administer the product. Accordingly, there is a wide variety of suitable formulations for use in the context of the present technology.

Techniques for formulation and administration of pharmaceutical compositions may be found in Remington's Pharmaceutical Sciences, 19th Ed., 19th Ed., Williams & Wilkins, 1995, and are well known to those skilled in the art. The choice of excipient will be determined in part by the particular method used to administer the product according to the present technology. Accordingly, there is a wide variety of suitable formulations for use in the context of the present technology. The following methods and excipients are merely exemplary and are in no way limiting.

The pharmaceutical compositions of the present technology may be manufactured using any conventional method, e.g., mixing, dissolving, granulating, levigating, emulsifying, encapsulating, entrapping, melt-spinning, spray-drying, or lyophilizing processes. However, the optimal pharmaceutical formulation will be determined by one of skill in the art depending on the route of administration and the desired dosage. Such formulations may influence the physical state, stability, rate of in vivo release, and rate of in vivo clearance of the administered agent.

The pharmaceutical compositions are formulated to contain suitable pharmaceutically acceptable carriers, and may optionally comprise excipients and auxiliaries that facilitate processing of the active compounds into preparations that can be used pharmaceutically. The administration modality will generally determine the nature of the carrier. For example, formulations for parenteral administration may comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's-solution, Ringer's solutions, or physiologically buffered saline. For tissue or cellular administration, penetrants appropriate to the particular barrier to be permeated are used in the formulation. Such penetrants are generally known in the art. For preparations comprising proteins, the formulation may include stabilizing materials, such as polyols (e.g., sucrose) and/or surfactants (e.g., nonionic surfactants), and the like.

Alternatively, formulations for parenteral use may comprise suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Emulsions, e.g., oil-in-water and water-in-oil dispersions, can also be used, optionally stabilized by an emulsifying agent or dispersant (surface-active materials; surfactants). Liposomes, as described above, containing the active agent may also be employed for parenteral administration.

Alternatively, the pharmaceutical compositions comprising the agent in dosages suitable for oral administration can be formulated using pharmaceutically acceptable carriers well known in the art. The preparations formulated for oral administration may be in the form of tablets, pills, capsules, cachets, lozenges, liquids, gels, syrups, slurries, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets. Oral formulations may employ liquid carriers similar in type to those described for parenteral use, e.g., buffered aqueous solutions, suspensions, and the like.

These preparations may contain one or more excipients, which include, without limitation: a) diluents such as sugars, including lactose, dextrose, sucrose, mannitol, or sorbitol; b) binders such as magnesium aluminum silicate, starch from corn, wheat, rice, potato, etc.; c) cellulose materials such as methyl cellulose, hydroxypropyhnethyl cellulose, and sodium carboxymethyl cellulose, polyvinyl pyrrolidone, gums such as gum arabic and gum tragacanth, and proteins such as gelatin and collagen; d) disintegrating or solubilizing agents such as cross-linked polyvinyl pyrrolidone, starches, agar, alginic acid or a salt thereof such as sodium alginate; or effervescent compositions; e) lubricants such as silica, talc, stearic acid or its magnesium or calcium salt, and polyethylene glycol; f) flavorants and sweeteners; g) colorants or pigments, e.g., to identify the product or to characterize the quantity (dosage) of active agent; and h) other ingredients such as preservatives, stabilizers, swelling agents, emulsifying agents, solution promoters, salts for regulating osmotic pressure, and buffers.

The pharmaceutical composition may be provided as a salt of the active agent, which can be formed with many acids, including but not limited to hydrochloric, sulfuric, acetic, lactic, tartaric, malic, succinic, etc. Salts tend to be more soluble in aqueous or other protonic solvents that are the corresponding free base forms.

The characteristics of the conjugate itself and the formulation of the conjugate can influence the physical state, stability, rate of in vivo release, and rate of in vivo clearance of the administered conjugate. Such pharmacokinetic and pharmacodynamic information can be collected through pre-clinical in vitro and in vivo studies, later confirmed in humans during the course of clinical trials. Guidance for performing human clinical trials based on in vivo animal data may be obtained from a number of sources, including, e.g., http://www.clinicaltrials.gov. Thus, for any compound used in the method of the present technology, a therapeutically effective dose in mammals, particularly humans, can be estimated initially from biochemical and/or cell-based assays. Then, dosage can be formulated in animal models to achieve a desirable circulating concentration range that modulates the conjugate activity. As human studies are conducted, further information will emerge regarding the appropriate dosage levels and duration of treatment for various diseases and conditions.

Toxicity and therapeutic efficacy of the conjugate can be determined by standard pharmaceutical procedures in cell cultures or experimental animals, e.g., for determining the LD50 (the dose lethal to 50% of the population) and the ED50 (the dose therapeutically effective in 50% of the population).

Additional Active Agents

Additional active agents may also be included in the composition of the present technology. The additional active agents, e.g., an anti-tumor agent (an agent active against proliferating cells), may be utilized in the composition prior to, concurrently with, or subsequent to the cells being contacted with a first active agent. For example, after urease has been targeted to the tumor cells, it may have the ability to modulate or regulate the tumor external environment, e.g., through pH changes. Active agents, such as anti-tumor agents, that favor a basic environment will then be more efficacious.

In certain aspects, substrates that are capable of being enzymatically processed by urease are contemplated for use as active agents. In some aspects, the active agent is a substrate that urease may utilize to form ammonium ions, e.g., urea.

Exemplary anti-tumor agents include cytokines and other moieties, such as interleukins (e.g., IL-2, IL-4, IL-6, IL-12 and the like), transforming growth factor-beta, lymphotoxin, tumor necrosis factor, interferons (e.g., gamma-interferon), colony stimulating factors (e.g., GM-CSF, M-CSF and the like), vascular permeability factor, lectin inflammatory response promoters (selectins), such as L-selectin, E-selectin, P-selectin, and proteinaceous moieties, such as C1q and NK receptor protein. Additional suitable anti-tumor agents include compounds that inhibit angiogenesis and therefore inhibit metastasis. Examples of such agents include protamine medroxyprogesteron, pentosan polysulphate, suramin, taxol, thalidomide, angiostatin, interferon-alpha, metalloproteinaseinhibitors, platelet factor 4, somatostatin, thromobospondin. Other representative and non-limiting examples of active agents useful in accordance with the present technology include vincristine, vinblastine, vindesine, busulfan, chiorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, blood products such as hematoporphyrins or derivatives of the foregoing. Other examples of active agents include genetic material such as nucleic acids, RNA, and DNA of natural or synthetic origin, including recombinant RNA and DNA. DNA encoding certain proteins may be used in the treatment of many different types of diseases. For example, tumor necrosis factor or interleukin-2 genes may be provided to treat advanced cancers; thymidine kinase genes may be provided to treat ovarian cancer or brain tumors; and interleukin-2 genes may be provided to treat neuroblastoma, malignant melanoma or kidney cancer. Additional active agents contemplated for use in the present technology are described in U.S. Pat. No. 6,261,537, which is incorporated by reference in its entirety herein. Anti-tumor agents and screens for detecting such agents are reviewed in Monga, M. and Sausville, E. A. (2002) *Leukemia* 16(4):520-6.

In some aspects, the active agent is a weakly basic anti-tumor compound whose effectiveness is reduced by a higher intracellular/lower extracellular pH gradient in a solid tumor. Exemplary weakly basic anti-tumor compounds include doxorubicin, daunorubicin, mitoxanthrone, epirubicin, mitomycin, bleomycin, vinca alkaloids, such as vinblastine and vincristine, alkylating agents, such as cyclophosphamide and mechlorethamine hydrochloride, and antrineoplastic purine and pyrimidine derivatives.

In some aspects, the composition includes urease, and lacks substantially any cytokines, e.g. tumor necrosis factor and/or interferons. In this aspect, urease alone, or with active agents other than cytokines, in combination with small molecule anti-tumor agents, is effective to inhibit cancer cell growth. Thus, in this aspect, the composition may or may not act in concert with endogenous or native cytokines present in the subject being treated, but the composition being administered does not contain additional, exogenous cytokines.

In some aspects, the additional active agent is not pemetrexed and/or carboplatin. In some aspects, the additional active agent is not a folate antimetabolite and/or a platinum agent.

Methods of Delivery and Administration

The antibody-urease conjugate composition may be delivered to the cancer cells by a number of methods known in the art. In therapeutic applications, the composition is administered to a patient having cancer cells in an amount sufficient to inhibit growth of the cancer cell(s). The pharmaceutical compositions can be exposed to the cancer cells by administration by a number of routes, including without limitation, parenteral, enteral, transepithelial, transmucosal, transdermal, and/or surgical.

Parenteral administration modalities include those in which the composition is administered by, for example, intravenous, intraarterial, intraperitoneal, intramedullary, intramuscular, intraarticular, intrathecal, and intraventricular injections, subcutaneous, intragonadal or intratumoral needle bolus injections, or prolonged continuous, pulsatile or planned perfusions or microinfusions using the appropriate pump technology. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration, vaginal administration, and rectal administration. Transdermal administration includes passive or active transdermal or transcutaneous modalities, including, for example, patches and iontophoresis devices, as well as topical application of pastes, salves, or ointments. Surgical techniques include implantation of depot (reservoir) compositions, osmotic pumps, and the like.

Single or multiple administrations of the active agent may be administered depending on the dosage and frequency as required and tolerated by the subject. In any event, the composition should provide a sufficient quantity of the active agent to effectively treat the subject.

In some aspects, the present technology contemplates the use of vesicles such as liposomes and/or nanocapsules as chemical entities for the delivery of the pharmaceutical composition comprising an antibody-urease conjugate to cancer cells. Such formulations may be preferred for the introduction of pharmaceutically-acceptable formulations of the polypeptides, pharmaceuticals, and/or antibodies disclosed herein. The formation and use of liposomes is generally known to those of skill in the art. (See, e.g., Backer, M. V., et al. (2002) *Bioconjug Chem* 13(3):462-7). In a preferred aspect, the disclosed composition may be entrapped in a liposome.

Nanocapsules can generally entrap compounds in a stable and reproducible way (Whelan, J. (2001) *Drug Discov Today* 6(23):1183-84). To avoid side effects due to intracellular polymeric overloading, such ultrafine particles (sized around 0.1 μm) may be designed using polymers able to be degraded in vivo. Biodegradable polyisobutylcyanoacrylate nanoparticles that meet these requirements are contemplated for use in the present technology, and such particles may be easily made, as described in, e.g., Lambert, G., et al. (2001) *Int J Pharm* 214(1-2):13-6. Methods of preparing polyalkyl-cyano-acrylate nanoparticles containing biologically active substances and their use are described in U.S. Pat. Nos. 4,329,332, 4,489,055 and 4,913,908. Nanocapsules are available commercially from sources such as Capsulution, Inc. (www.capsulution.com).

Pharmaceutical compositions containing nanocapsules for the delivery of compositions are described in U.S. Pat. Nos. 5,500,224, 5,620,708 and 6,514,481. U.S. Pat. No. 5,500,224 describes a pharmaceutical composition in the form of a colloidal suspension of nanocapsules comprising an oily phase consisting essentially of an oil containing dissolved therein a surfactant, and suspended therein a plurality of nanocapsules having a diameter of less than 500 nanometers. U.S. Pat. No. 5,620,708 describes compositions and methods for the administration of drugs and other active agents. The compositions comprise an active agent carrier particle attached to a binding moiety which binds specifically to a target molecule present on the surface of a mammalian enterocyte. The binding moiety binds to the target molecule with a binding affinity or avidity sufficient to initiate endocytosis or phagocytosis of the particulate active agent carrier so that the carrier will be absorbed by the enterocyte. The active agent will then be released from the carrier to the host's systemic circulation. In this way, degradation of degradation-sensitive drugs, such as polypeptides, in the intestines can be avoided while absorption of proteins and polypeptides from the intestinal tract is increased. Alternatively, the present technology contemplates release of the active agent in the environment surrounding the target cell. For example, in one aspect, antibody-urease conjugates are released from the nanocapsule following target moiety binding to the target cell, such that urease is released into the microenvironment surrounding the target cell, e.g., a tumor cell. U.S. Pat. Nos. 6,379,683 and 6,303,150 describe methods of making nanocapsules and the use thereof, and are incorporated herein by reference.

The pharmaceutical composition used is administered to a subject in an effective amount. Generally, an effective amount is an amount effective to either (1) reduce the symptoms of the disease sought to be treated; or (2) induce a pharmacological change relevant to treating the disease sought to be treated. For cancer, an effective amount may include an amount effective to: reduce the size of a tumor; slow the growth of a tumor; prevent or inhibit metastases; or increase the life expectancy of the affected subject, the contacting includes adding to the cells a conjugate comprising a targeting moiety and a first coil-forming peptide characterized by a selected charge and an ability to interact with a second, oppositely charged coil-forming peptide to form a stable α-helical coiled-coil heterodimer. Subsequently, a liposome is added to the cells. The liposome comprises an exterior surface and an internal compartment; an active agent, e.g., urease, located within the internal compartment of the liposome; and a plurality of second peptides, wherein each second peptide is connected to the exterior surface of the liposome.

In some aspects, the contacting includes adding liposomes to the cells, wherein the liposomes have the active agent, e.g., antibody-urease conjugates, in entrapped form, and outer surfaces of the liposome includes a cell targeting moiety effective to bind specifically to a target surface, and a hydrophilic polymer coating effective to shield the targeting moiety from interaction with the target surface. The hydrophilic polymer coating may be made up of polymer chains which are covalently linked to surface lipid components in the liposomes through releasable linkages. In some aspects, a releasing agent is added to the tumor cells in an amount effective to cause release of a substantial portion of the linkages in the added liposomes, thereby exposing the targeting moiety to the target surface. The releasable linkages may be reducible chemical linkages such as disulfide, ester and peptide linkages.

In some aspects, a method of liposome-based therapy for a mammalian subject is contemplated. The method includes systemically administering to the subject, e.g., intravenously administering, liposomes having a surface-bound targeting moiety and a hydrophilic polymer coating. The hydrophilic polymer coating, comprised of releasably attached polymer chains, is effective to shield the targeting moiety from interaction with its target. The administered liposomes are allowed to circulate systemically until a desired biodistribution of the liposomes is achieved. A releasing agent is administered to the subject in an amount effective to cause cleaving of a substantial portion, e.g., greater than about 50%, preferably greater than about 70%, and more preferably greater than about 90% of the releasable linkages in the administered liposomes. The targeting moiety is exposed upon release of the hydrophilic polymer chain for interaction with its target.

In some aspects, the liposomes are used for treatment of a solid tumor. The liposomes include antibody-urease conjugate, and optionally, an additional active agent, e.g., an anti-tumor drug, in entrapped form and are targeted to the tumor region by a targeting moiety effective to bind specifically to a tumor-specific antigen. In an exemplary method, liposomes are targeted to the vascular endothelial cells of tumors by including a VEGF ligand in the liposomes, for selective attachment to Flk-1,2 receptors expressed on the proliferating tumor endothelial cells (Niederman, T. M., et al. (2002) *Proc Natl Aced Sci* 99(10): 7009-14).

In some aspects, the liposomes have a size between about 30-400 nm. Liposomes in this size range have been shown to be able to enter tumors through "gaps" present in the endothelial cell lining of tumor vasculature (Maruyama, K, et al. (1999) *Adv Drug Deliv Rev* 40(1-2):89-102).

Following administration of the liposomes, e.g., intravenous administration, and after sufficient time has elapsed to allow the liposomes to distribute through the subject and bind to the tumor, a releasing agent is administered to the subject to release the hydrophilic surface coating from the liposomes. Release of the surface coating is effective to expose the targeting moiety to allow binding of the liposomes to the target cells. In one aspect, the hydrophilic surface coating is attached to the liposomes by pH sensitive linkages. The linkages are released after the liposomes bind to the tumor.

The liposomes in any of the aspects described above may, optionally, include one or more entrapped anti-tumor drugs or imaging agents or both. The liposomes may be added and allowed to distribute, after which a releasing agent can be administered to release the hydrophilic surface coating to expose the attached targeting moiety and initiate binding Liposomes may be prepared and administered as described in U.S. Pat. No. 6,043,094, which is incorporated herein by reference.

Additional delivery agents such as small unilamellar vesicles (SUV's), as described in U.S. Pat. No. 6,180,114, which is incorporated herein by reference in its entirety, may be employed in the present technology.

It is understood by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, may be constrained by the blood-brain barrier which resists the entry of macromolecules into the subarachnoid space. In these types of tumors, the therapeutic composition may preferably be administered directly to the tumor site. Thus, for example, brain tumors can be treated by administering the therapeutic composition directly to the tumor site, e.g., through a bolus injection, microinfusion, or a surgically implanted catheter.

Dosage

For the method of the present technology, any effective administration regimen regulating the timing and sequence of doses may be used. Exemplary dosage levels for a human subject will depend on the mode of administration, extent (size and distribution) of the tumor, patient size, and responsiveness of the cancer to urease treatment.

Where an antibody-urease conjugate composition is administered to, such as injected directly into a tumor, an exemplary dose is about 0.1 to 1,00010 μg/kg body weight, such as about 0.2 to 5 μg/kg, or about 0.5 to 2 μg/kg. The placement of the injection needle may be guided by conventional image guidance techniques, e.g., fluoroscopy, so that the physician can view the position of the needle with respect to the target tissue. Such guidance tools can include ultrasound, fluoroscopy, CT or MRI.

In some aspects, the effectiveness or distribution of the administered dose of antibody-urease conjugates may be monitored, during or after administration of antibody-urease conjugate into the tumor, by monitoring the tumor tissue by a tool capable of detecting changes in pH within the cancerous tissue region of the subject. Such tools may include a pH probe that can be inserted directly into the tumor, or a visualization tool, such as-magnetic resonance imaging (MRI), computerized tomography (CT), or fluoroscopy. MRI interrogation may be carried out in the absence of additional imaging agents, based simply on differences in magnetic properties of tissue as a function of pH. CT or fluoroscopic imaging may require an additional pH-sensitive imaging agent whose opacity is affected by the pH of the tissue medium. Such agents are well known to those of skill in the art.

Before any antibody-urease conjugates administration, the tumor tissue can be visualized by its lower pH relative to surrounding normal tissue. Thus, the normal tissue may have a normal pH of about 7.2, whereas the tumor tissue may be 0.1 to 0.4 or more pH units lower. That is, before any antibody-urease conjugate is injected, the extent of tumor tissue can be defined by its lower pH. Following urease administration, the pH of the tumor region having urease will begin to rise, and can be identified by comparing the resulting images with the earlier pre-dosing images.

By interrogating the tissue in this manner, the degree of change in pH and extent of tissue affected may be monitored. Based on this interrogation, the physician may administer additional composition to the site, and/or may administer composition at additional areas within the tumor site. This procedure may be repeated until a desired degree of pH changes, e.g., 0.2 to 0.4 pH units, has been achieved over the entire region of solid tumor.

Dosing such as by direct injection may be repeated by suitable intervals, e.g., every week or twice weekly, until a desired end point, preferably substantial or complete regression of tumor mass is observed. The treatment efficacy can be monitored, as above, by visualizing changes in the pH of the treated tissue during the course of treatment. Thus, before each additional injection, the pH of the tissue can be visualized to determine the present existing extent of tumor, after which changes in the pH of the tissue can be used to monitor the administration of the new dose of antibody-urease composition to the tissue.

Where the antibody-urease composition is administered parenterally by a method other than direct injection, an exemplary dose of the antibody-urease composition is 100-100,000 international units/kg urease activity/kg subject body weight. As noted herein, the antibody-urease composition in this method includes an antibody for targeting urease to the cancer cells, e.g., site of solid tumor, or for sequestering urease, e.g., in liposomal form, selectively at-the tumor site.

Imaging techniques that are sensitive to changes in tissue pH, may be used to monitor the effectiveness of the dose administered. Since such targeting may take several hours or more, the method may involve monitoring tumor pH, as above, before the injection of antibody-urease composition, and several hours following dosing, e.g., 12-24 hours, to confirm that the tumor site has been adequately dosed, as evidenced by rise in pH of the tumor region. Depending on the results of this interrogation, the method may dictate additional dosing until a desired rise in pH, e.g., 0.2-0.4 pH units, is observed. Once this dose is established, the patient may be treated with a similar dose of the urease composition on a regular basis, e.g., one or twice weekly, until a change in tumor size or condition is achieved.

Final dosage regimen will be determined by the attending physician in view of good medical practice, considering various factors that modify the action of drugs, e.g., the agent's specific activity, the severity of the disease state, the responsiveness of the patient, the age, condition, body weight, sex, and diet of the patient, the severity of any infection, and the like. Additional factors that may be taken into account include time and frequency of administration, drug combination(s), reaction sensitivities, and tolerance/response to therapy. Further refinement of the dosage appropriate for treatment involving any of the formulations mentioned herein is done routinely by the skilled practitioner, especially in light of the dosage information and assays disclosed, as well as the pharmacokinetic data observed in clinical trials. Appropriate dosages may be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active agent or to maintain the desired effect. Accordingly, the pharmaceutical compositions can be administered in a single dose, multiple discrete doses, continuous infusion, sustained release depots, or combinations thereof, as required to maintain desired minimum level of the agent.

Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps for continuous infusion.

Compositions comprising the conjugate in a pharmaceutical acceptable carrier may be prepared, placed in an appropriate container, and labeled for treatment of an indicated condition. Conditions indicated on the label may include, but are not limited to, treatment of various cancer types. Kits, as described below, are also contemplated, wherein the kit comprises a dosage form of a pharmaceutical composition and a package insert containing instructions for use of the composition in treatment of a medical condition.

Generally, the conjugate compositions are administered to a subject in an effective amount. Generally, an effective amount is an amount effective to either (1) reduce the symptoms of the disease sought to be treated; or (2) induce a pharmacological change relevant to treating the disease sought to be treated. For cancer, an effective amount may include an amount effective to: reduce the size of a tumor; slow the growth of a tumor; prevent or inhibit metastases; or increase the life expectancy of the affected subject.

Method of Treatment

The present technology provides for a method of treating cancer in a subject, comprising administering to the subject a therapeutically effective amount of the composition provided herein, thereby treating cancer in the subject. Cancers suitable for treatment by the methods herein include generally carcinomas, leukemias, lymphomas, and sarcomas. Carcinomas may be of the anus, biliary tract, bladder, breast, colon, rectum, lung, oropharynx, hypopharynx, esophagus, stomach, pancreas, liver, kidney, gallbladder and bile ducts, small intestine, urinary tract, ovarian, colon, non-small cell lung carcinoma, genital tract, endocrine glands, thyroid, and skin. Other suitable cancers include carcinoid tumors, gastrointestinal stromal tumors, head and neck tumors, primary tumors, hemangiomas, melanomas, malignant mesothelioma, multiple myeloma, and tumors of the brain, nerves, eyes, and meninges.

In some aspects, the cancers to be treated form solid tumors, such as carcinomas, sarcomas, melanomas and lymphomas. In some aspects, the cancer is one or more of non-small cell lung carcinoma, breast, pancreatic, ovarian, lung, colon cancer, or a combination thereof. In some aspects, the cancer is non-small cell lung carcinoma. In some aspects, the subject is a human.

A therapeutically effective dose can be estimated by methods well known in the art. Cancer animal models such as immune-competent mice with murine tumors or immune-compromised mice (e.g., nude mice) with human tumor xenografts are well known in the art and extensively described in many references incorporated for reference herein. Such information is used in combination with safety studies in rats, dogs and/or non-human primates in order to determine safe and potentially useful initial doses in humans. Additional information for estimating dose of the organisms can come from studies in actual human cancer, reported clinical trials.

In some aspects, the method of treatment for cancer is intended to encompass curing, as well as ameliorating at least one symptom of cancer. Cancer patients are treated if the patient is cured of the cancer, the cancer goes into remission, survival is lengthened in a statistically significant fashion, time to tumor progression is increased in a statistically significant fashion, there is a reduction in lymphocytic or hematopoietic tumor burden based on standard criteria established for each type of lymphocytic or hematopoietic malignancy, or solid tumor burden has been decreased as defined by response evaluation criteria in solid tumors (RECIST 1.0 or RECIST 1.1, Therasse et al. J Natl. Cancer Inst. 92(3):205-216, 2000 and Eisenhauer et al. Eur. J. Cancer 45:228-247, 2009). As used herein, "remission" refers to absence of growing cancer cells in the patient previously having evidence of cancer. Thus, a cancer patient in remission is either cured of their cancer or the cancer is present but not readily detectable. Thus, cancer may be in remission when the tumor fails to enlarge or to metastesize. Complete remission as used herein is the absence of disease as indicated by diagnostic methods, such as imaging, such as x-ray, MRI, CT and PET, or blood or bone marrow biopsy. When a cancer patient goes into remission, this may be followed by relapse, where the cancer reappears.

In some aspects, the treatment is not in combination with pemetrexed and/or carboplatin. In some aspects, the treatment is not in combination with a folate antimetabolite compound and/or a platinum agent.

Kits

In some aspects, this present technology provides kits for inhibiting the growth of tumor cells using the methods described herein. The kits include a container containing one or more active agents. The kits can additionally include any of the other components described herein for the practice of the methods of the present technology.

The kits may optionally include instructional materials containing directions (i.e., protocols) disclosing the use of active agents for inhibiting tumor cell growth. Thus, in one aspect, the kit includes a pharmaceutical composition containing an active agent, preferably a urease enzyme, and instructional materials teaching the administration of the composition to a subject, for the treatment of a cancer in the subject. In one aspect, the instructional material teaches administering the urease composition to a subject in an amount which is dependent on the size, of the tumor and between 0.1 to 100 international units urease activity per $mm^3$ tumor, when the composition is administered by direct injection into the tumor, and in an amount between 100-

100,000 international units/kg international units urease activity/kg subject body weight, when the composition is administered parenterally to the subject other than by direct injection into the tumor.

In another aspect, the instructional material teaches administering the urease composition to a subject who is also receiving a weakly basic anti-tumor compound whose effectiveness is reduced by a higher intracellular/lower extracellular pH gradient in a solid tumor, in an amount of urease effective to reduce or reverse the higher intracellular/lower extracellular pH gradient in a solid tumor.

Alternatively, the instructional material teaches administering the urease composition to a subject containing, or suspected of containing, a solid tumor, under conditions effective to localize the urease in a solid tumor in the subject, interrogating the subject with a diagnostic tool capable of detecting changes in extracellular pH in a subject's tissue, and identifying a tissue region within the subject that shows an elevation in extracellular pH following said administering.

While the instructional materials typically comprise written or printed materials they are not limited to such. Any medium capable of storing such instructions and communicating them to an end user is contemplated by the present technology. Such media include, but are not limited to electronic storage media (e.g., magnetic discs, tapes, cartridges, chips), optical media (e.g., CD ROM), and the like. Such media may include addresses to Internet sites that provide such instructional materials.

EXAMPLES

The following examples are given for the purpose of illustrating various aspects of the disclosure. They are not meant to limit the disclosure in any fashion. One skilled in the art will appreciate that the disclosure is well adapted to carry out the objects and obtain the ends and advantages mentioned, as well any objects, ends and advantages inherent herein. The present examples (along with the methods described herein) are presently representative of preferred aspects. They are exemplary, and are not intended as limitations on the scope of the disclosure. Variations and other uses which are encompassed within the spirit of the disclosure as defined by the scope of the claims will occur to those skilled in the art.

Example 1: L-DOS47: An Antibody-Urease Conjugate Targeting CEACAM6-Expressing Tumors The microenvironment of tumors is often acidic relative to normal tissue. Accumulation of lactate from anaerobic glycolysis in response to regional hypoxia from aberrant vasculature seems to be the direct cause (1, 2). However, cancer cells continue to metabolize glucose anaerobically even in the presence of oxygen (3). This suggests the converted metabolic phenotype and resulting acidic environment may confer a growth advantage to cancer cells (4).

It has been shown that Jack bean urease, which converts urea into ammonia and raises solution pH, is cytotoxic to cancer cells (8). Intratumoral injection of the enzyme in mice bearing human breast and lung xenografts also delayed tumor growth significantly (8). However, intratumoral delivery of cancer therapeutics in a clinical setting is a difficult practice. In patients with advanced and significant metastatic disease, intratumoral injection is not a viable option. A more practical approach is to deliver the enzyme via intravenous injection. However, urease lacks a targeting domain and systemic delivery of the enzyme may result in off-target toxicity. An antibody-enzyme conjugate that targets tumors specifically is used to deliver urease to cancer sites. This antibody used in the conjugate recognizes CEACAM6 specifically in non-small cell lung cancer patients.

A single-domain camelid antibody fragment (AFAIKL2, SEQ ID NO. 1) that recognizes CEACAM6 on lung adenocarcinoma cells (17) was chosen for conjugation to Jack bean urease (DOS47) to generate a cancer therapeutic. The present technology describes some of the pertinent preclinical studies that were conducted on this anti-CEACAM6-urease conjugate (L-DOS47), which is currently in a human phase I clinical study.

The anti-tumor activity of Jack bean urease was combined with the specificity of anti-CEACAM6 single domain antibody in the form of antibody-urease conjugate (L-DOS47). L-DOS47 bound specifically to CEACAM6-expressing cancer cell lines and exerted potent cytotoxic effects. Competitive binding assay showed that the binding affinity of L-DOS47 was about 500 times stronger than that of the native single domain antibody due to increased avidity. Cytotoxicity of L-DOS47 depends on the availability of urea in situ and susceptibility of targeted cells to ammonia toxicity. BxPC-3 cells were protected from L-DOS47 effects by silencing the CEACAM6 gene, while CEACAM6 overexpression rendered the transfected H23 cells susceptible to L-DOS47 cytotoxicity. Immunochemical staining of human normal and cancer tissues showed that L-DOS47 bound preferentially to lung adenocarcinoma, as well as to colon and pancreatic adenocarcinoma with positive but weaker staining. A metastasis study of lung adenocarcinoma A549 cells in mice also showed that L-DOS47 was effective in reducing cancer cell counts in lung at a concentration of 10 μg/mL.

Materials.

Jack bean (*Canavalia ensiformis*) urease was obtained from BioVectra Inc. (PEI, Canada) and further purified by acid precipitation, alcohol fractionation, and ion-exchange chromatography. The purity of the enzyme was >97% as determined by SDS-PAGE, HPLC, and mass spectrometry. One unit of urease is defined as the production of 1 μmole/minute of ammonia at 25° C. and pH 7.6.

A phage library derived from the heavy chain antibody repertoire of a llama was used to identify a single-domain antibody (sdAb) by panning against the non-small cell lung adenocarcinoma A549. The sdAb was designated AFAI (17). The gene sequence of AFAI was optimized for conjugation purpose and renamed as AFAIKL2. The AFAIKL2 antibody was then cloned and expressed in *E. coli* BL21 (DE3) pT7-7 system. The antibody was purified from the inclusion bodies using ion-exchange chromatography. Conjugation of the antibody to urease was performed using the heterobifunctional cross-linker N-succinimidyl(4-iodoacetyl)amino-benzoate (SIAB). The AFAIKL2 antibody was first activated with the NHS ester portion of the SIAB linker via primary amine groups. The activated antibody was bound to urease through iodoacetyl group of the cross-linker to free sulfhydryl groups present on the enzyme. A targeted conjugation ratio (1:6 to 1:10, urease to antibody ratio) was controlled by mixing the high purity urease and activated antibody at a mass ratio of 2:1. The antibody-urease conjugate was purified by ultrafiltration.

Urea, trypsin (tissue culture grade), phenazine ethosulfate (PES), sodium nitroprusside, sodium hypochlorite solution, phenol, NaCl, $KH_2PO_4$, $MgSO_4$, $NaHCO_3$, and glutaraldehyde were purchased from Sigma Chemical Co. (St. Louis, MO). 3-(4,5-dimethylthiazol-2-yl)-5-(3-carboxymethoxyphenyl)-2-(4-sulfophenyl)-2H-tetrazolium (MTS) and trypsin (for use in peptide fragmentation and mass spectrometry analysis), was purchased from Promega Corp. (Madison, WI). Hydrogen peroxide (30%), SIAB, KCl, D-Glucose, HCl, $Na_2HPO_4$, and $NaH_2PO_4$ were purchased from Fisher Scientific (Ottawa, ON). Bovine serum albumin fraction V (BSA) was purchase from Roche (Indianapolis, IN). Ammonium chloride (0.100 M) was purchased from Ricca Chemical (Arlington, TX). Anti-AFAIKL2-peroxidase conjugate was produced by Rockland Immunochemicals (Gilbertsville, PA). Cell culture medium (RPMI), fetal bovine serum, and antibiotics were obtained from Life Technologies (Burlington, ON). Female CrTac:NCr-Foxn1$^{nu}$ nude mice were supplied by Taconic (Hudson, NY). Modified Krebs Ringer buffer (KRB) used in the experiments contained NaCl (98.3 mM), KCl (4.73 mM), $KH_2PO_4$ (1.19 mM), $MgSO_4$ (1.19 mM), D-Glucose (11.7 mM), $Na_2HPO_4$ (11.1 mM), and $NaH_2PO_4$ (2.77 mM), pH 7.2.

Indophenol Assay

The amount of ammonia produced by the urease enzymatic reaction was determined using a modified indophenol assay (18). In brief, Solution A was freshly prepared by dissolving 165 mg of phenol and 132 mg of NaOH pellets in 10 mL of water, followed by adding 66 μL of sodium nitroprusside solution (10 mg/mL). Solution B was prepared by adding 40 μL of sodium hypochlorite to 5 mL of water. Sample solutions (30 μL each) from the whole-cell binding assay (see below) were transferred to a new 96-well plate containing 50 μL/well of 5N NaOH:$H_2O$ (3.3:46.7) and 20 μL/well water. Solution A (50 μL/well) and Solution B (50 μL/well) were added and the plates were then transferred to a microplate reader for color development at 37° C. for 30 minutes. OD was measured at 630 nm. The amount of ammonia produced in the wells was calculated from a calibration curve using ammonia chloride as standards (from 0 to 150 μM).

Whole-Cell Binding Assay of L-DOS47

Cell monolayers were prepared by seeding 100 μL/well of tumor cells ($4\times10^4$ cells/well) in 96-well culture plates and incubated overnight at 37° C. Medium was removed from the plates and the cell monolayers were fixed with 100 μL/well of 0.05% glutaraldehyde (in phosphate buffered saline, PBS) for 10 minutes at room temperature (RT). The plates were then washed with PBS and 120 μL/well of glycine solution (50 mM) was added and incubated at 37° C. for 20 minutes. After incubation, the plates were blocked with 120 μL/well of 1% BSA/PBS at 37° C. for 30 minutes. Then, the plates were washed 3 times with Buffer A (0.05% BSA in PBS) and 80 μL/well of diluted L-DOS47 or DOS47 solutions were added and incubated at 37° C. for 1.5 hours. Binding signal was generated by either urea or antibody methods: (1) With the urea approach, the plates were washed 4 times with Buffer A and 80 μL/well of 20 mM urea (prepared in 0.1M phosphate buffer, pH7.6) was added and incubated at 37° C. for 30 minutes. After incubation, 40 μL/well of 1N HCl was added to stop the reaction. The amount of ammonia produced in each well was determined using the indophenol assay. (2) For the antibody method, endogenous peroxidase was first quenched with 100 μL/well of 0.3% hydrogen peroxide for 30 minutes. before the blocking step. After incubation with the test articles, the plates were washed with PBS and diluted anti-AFAIKL2-peroxidase antibody conjugate (1:8000) were prepared in Buffer A containing 0.05% Tween-20 and 0.1% milk powder. The plates were washed 3 times with Buffer A and 100 μL/well of antibody-peroxidase conjugate was added to the plates. After incubating at 37° C. for 1 hour, the plates were washed 3 times with Buffer A. Peroxidase substrate was prepared at 1 mM in sodium citrate buffer containing 0.03% $H_2O_2$ and 100 μL/well of the substrate solution was added and incubated at RT for 30 minutes. The plates were transferred to a microplate reader for OD measurement at 405 nm.

Cytotoxicity Assay of L-DOS47

Cell monolayers were prepared by seeding 100 μL/well of tumor cells ($4\times10^4$ cells/well) in 96-well culture plates and incubated overnight at 37° C. Medium was removed from each well and 80 μL/well of either L-DOS47 or DOS47 were added and further incubated at 37° C. for 2 hours. After incubation, the plates were washed 3 times with Buffer A. Then, 100 μL/well of urea (20 mM) in KRB was added to the plates, which were incubated at 37° C. overnight. Medium was removed and replaced with 100 μL/well plain medium. Cell viability was determined using MTS cell viability assay, in which a mixture of MTS/PES solution (20:1 vol/vol; MTS, 2 mg/mL; PES, 1 mg/mL) was prepared and 20 μL/well of the mixture was added to the plates. The plates were then incubated at 37° C. for 1-2 hours and OD was measured at 630 nm with reference at 490 nm.

Cell-Based Electrochemiluminescence (ECL) Binding Assay

L-DOS47, AFAIKL2 antibody, and DOS47 were labelled with ruthenium-NHS-ester (Sulfo-Tag, Meso Scale Discovery MSD; Rockville, MD) according to manufacturer's instructions. These ruthenium-tagged proteins allowed direct measurement of binding of L-DOS47 and AFAIKL2 to target antigen. For the direct binding assay, BxPC-3 cell monolayer was prepared on 96-well SECTOR PR High-Bind plate (MSD). After fixing and blocking, various amount of L-DOS47-tag or AFAIKL2-tag were added. The plate was incubated at 37° C. for 1.5 hours. After incubation, the plate was washed two times and filled with Read Buffer (MSD). The ECL signal was then read immediately using the SECTOR PR-100 reader (MSD). For the competitive binding assay, L-DOS47 or AFAIKL2 antibody was used to inhibit the binding of L-DOS47-tag to BxPC-3 cells. L-DOS47-tag at 1 μg/mL was used to bind to BxPC-3 cells. Various concentrations of competitors (L-DOS47 or AFAIKL2) were used to compete the binding of the tagged L-DOS47. After incubation, the plate was washed two times and filled with Read Buffer. The plate was then read immediately using the SECTOR PR-100 reader.

CEACAM6 Gene Knockdown in BxPC-3 Cells

To confirm that CEACAM6 is the specific antigen recognized by L-DOS47, the CEACAM6 gene of the positive cell line BxPC-3 was silenced using HuSH-29 hairpin expression clones from OriGene (Rockville, MD). These plasmids transcribe short hairpin RNA (shRNA) sequences, which block target gene transcription via RNA interference. The BxPC-3 cell was transfected with the HuSH plasmids and stably transfected cells were selected using puromycin. Different clones were obtained from the transfection of HuSH6 (AAGGCGAAAGAGTGGATGGCAACAGTCTA (SEQ ID NO: 5)), HuSH7 (AAGAAGCAACCGGACAGTTCCATGTATAC (SEQ ID NO: 6)), and the control plasmid HuSH-TRS. Two positive stable cell lines (HUSH #6 and HUSH #7) and the control (HUSH-TRS) were obtained by antibiotic selection. These clones were then used to check for binding with L-DOS47 using whole-cell binding assay. After incubation with L-DOS47, the plates were washed 3 times with Buffer A and 80 μL/well of 20 mM urea (prepared in 0.1 M phosphate buffer, pH 7.6) was added. The plates were incubated at 37° C. for 30 minutes.

The enzymatic reaction was stopped by adding 40 μL/well of 1 N HCl. The amount of ammonia produced was determined using the indophenol assay.

Transfection of CEACAM6 Gene to H23 Cells

Mammalian expression vector containing the G418 selectable marker was cloned with PMP-GFP (plasma membrane protein-green fluorescent protein) and CEACAM6 genes. Cellfectin reagent (Life Technologies) was used to transfect the expression vector into H23 cells. In brief, $2\times10^6$ cells/well of H23 cells in 2 mL complete RPMI medium (containing 10% fetal bovine serum and 50 U/ml penicillin and 50 μg/ml streptomycin) were seeded in a 6-well culture plate and incubated at 37° C. overnight. Cellfectin reagent (10 μL) and DNA (1-2 μL) were diluted in 100 μL serum free RPMI medium, respectively. The two diluted solutions were then combined, mixed gently, and incubated at RT for 30 minutes. The plates were washed twice with 1.5 mL serum-free RPMI medium. The combined solution was diluted in 0.8 mL serum-free RPMI medium, mixed gently, and added to the cells. The cells were incubated at 37° C. in a $CO_2$ incubator overnight. Next day, the medium was replaced with 2 mL of complete RPMI medium. The transfected cells co-expressed GFP from the same mRNA as CEACAM6. The transfected cells were selected by incubation in medium containing 400 μg/mL G418 antibiotic. Cells were sorted directly or after incubation with cy5.5 labelled L-DOS47, which indicates surface expression of CEACAM6.

Immunochemical Staining of Human Tumor Tissues by L-DOS47

A total of 400 tissue samples representing 42 cancerous and normal tissues were screened (Axel Wellmann, University Hospital Aachen, RWTH Aachen Germany). The slides were first incubated in a dry oven at 62° C. for 1 hour in a vertical orientation to remove the paraffin. Then, the slides were dewaxed in xylene substitute for 5×4 minutes. The slides were hydrated in 100%, 95%, and 75% ethanol for 2×3 minutes each, and then immersed in tap water for 5 minutes. Endogenous peroxidase was quenched with 0.3% $H_2O_2$ for 30 minutes. Vectastain Elite ABC Kit (Vector Labs, Burlington, ON) was used to detect L-DOS47 binding on the slides. In brief, after washing in PBS for 3×5 minutes, the slides were incubated in blocking serum at 4° C. overnight. The slides were then incubated in L-DOS47 solution (20 μg/mL in Buffer A) at 37° C. for 1.5 hours. After washing with PBS, the slides were incubated with mouse anti-urease antibody (Sigma, 1:1500) at 37° C. for 1 hour. After washing with PBS, the slides were incubated with biotinylated secondary antibody solution (Vector Labs) for 30 minutes. After washing with PBS, the slides were incubated with Vectastain Elite ABC reagent for 30 minutes. After washing with PBS, the slides were incubated in fresh DAB (3,3'-diaminobenzidine) peroxidase substrate solution mix (Vector Labs) at RT for 2 minutes. The reaction was stopped by washing in tap water for 5 minutes. The slides were then counterstained in Meyer's hematoxylin for 10 sec. The slides were dehydrated in 75%, 80%, 95%, and 100% ethanol. After clearing in xylene, the slides were mounted with Clarion Mounting Medium.

A549 Metastasis Study

A549 tumor cells ($5\times10^6$) were seeded and grown in low binding culture plates. Once sufficient numbers were obtained, cells were harvested and resuspended in culture medium at a concentration of $5\times10^6$ cells/mL. Cells were then placed into 6-well, low-binding tissue culture plates at 1 mL/well. L-DOS47 (1 mL) at final concentration of 10 or 15 μg/mL was then added to each well. The isotype control was treated with 10 μg/mL of the V21-DOS47 conjugate (an antibody-urease conjugate targeting vascular endothelial growth factor (VEGF) receptor). The cells were incubated at 37° C. for 4 hours. After incubation, cells were centrifuged and washed 3 times with sterile PBS and resuspended to $1\times10^7$ cells/mL in sterile PBS. Each mouse then received a single inoculation of $1\times10^6$ treated cells. This study consisted of 4 groups of female CrTac:NCr-Foxn1$^{nu}$ mice (Untreated, Isotype, and L-DOS47 (10 and 15 μg/mL)). A total of forty mice (10 per each group) were inoculated with A549 tumor cells intravenously via a tail vein.

Five animals per group were euthanized on Day 22 (3 weeks) while the remaining animals were maintained through Day 71 (10 weeks). Following sacrifice, animals were intratracheally injected with India ink (Calvert Labs; Olyphant, PA); the lungs were then excised and subsequently fixed in Fekete's solution (Calvert Labs). The effect of the test article on tumor metastasis was determined by counting the number of metastatic tumors (foci) in each lung under a dissecting microscope. Representative lungs from each group were photographed.

Binding of L-DOS47 to Various Cancer Cell Lines

Different binding profiles of L-DOS47 were observed among five tumor cell lines—BxPC-3, Capan-1, ZR-75-30, LS174T, and MDA-MB231 (FIG. 1A). The results showed that L-DOS47 bound well to the two pancreatic (BxPC-3 and Capan-1) and breast (ZR-75-30) cell lines, indicating CEACAM6 antigen was expressed on the cell surface. Moderate binding was also observed in the colon cell line LS174T, but no binding was found in the breast cell line MDA-MB231 (negative control). The AFAIKL2 antibody, when conjugated to the urease enzyme, provided specific targeting towards CEACAM6-expressing cells. This was confirmed by the absence of binding signal in cells treated with DOS47 (data not shown).

Cytotoxicity of L-DOS47

FIG. 1B showed that both BxPC-3 and ZR-75-30 are susceptible to L-DOS47 cytotoxicity. A rapid drop in cell survival was observed in these two cell lines treated with less than 1 μg/mL of L-DOS47. Moderate effects were observed in Capan-1 and LS174T cells. L-DOS47 does not have any effects on the negative control cell line MDA-MB231. A list of binding and cytotoxicity results from more cell lines was shown in Table 1. L-DOS47 cytotoxicity depends directly on the binding activity of L-DOS47 on corresponding cell lines. The weaker cytotoxic response of A549 and Capan-1 are due to more tolerant of these two cell lines to ammonia toxicity (data not shown). On the other hand, H23 cells are highly sensitive to ammonia (data not shown). Despite the absence of CEACAM6 antigen on the cell surface, H23 cells still show some weak cytotoxic response to L-DOS47, probably due to the presence of non-specifically bound L-DOS47 in the wells.

TABLE 1

Summary of results obtained from various binding and cytotoxicity studies of L-DOS47 on nine human tumor cell lines

| Cell lines | | Binding assay | Cytotoxicity assay |
|---|---|---|---|
| MDA-MB231 | Breast adenocarcinoma | − | − |
| MCF-7 | Breast carcinoma | − | − |
| ZR-75-30 | Breast ductal carcinoma | +++ | +++ |
| LS174T | Colon adenocarcinoma | ++ | ++ |
| A549 | Lung adenocarcinoma | ++ | + |
| H23 | Lung adenocarcinoma | − | + |
| BxPC-3 | Pancreatic adenocarcinoma | +++ | +++ |

TABLE 1-continued

| Summary of results obtained from various binding and cytotoxicity studies of L-DOS47 on nine human tumor cell lines | | | |
|---|---|---|---|
| Cell lines | | Binding assay | Cytotoxicity assay |
| Capan-1 | Pancreatic adenocarcinoma | +++ | ++ |
| MIA PaCa-2 | Pancreatic carcinoma | + | + |

Where:
+, positive (the number of + indicates the strength of activity);
–, negative Five cell lines (BxPC-3, Capan-1, ZR-75-30, LS174T, and A549) from four human tissues showed strong L-DOS47 binding and good susceptibility to L-DOS47 cytotoxicity (except A549) as shown in Table 1. The cytotoxic effects of L-DOS47 are more or less dependent on the relative binding strength to the cancer cells. The results in the graphs represent the mean (n=3) of representative experiments. The standard deviation (SD) was less than 10% for all values.

Direct and Competitive Binding of L-DOS47 to BxPC-3 Cells

The cell-based electrochemiluminescence binding assay allows direct detection of ruthenium-labelled antibody conjugate bound to tumor cells. In FIG. 2A, both ruthenium-tagged L-DOS47 and AFAIKL2 antibody were found to bind to BxPC-3 cells, whereas ruthenium-tagged DOS47 acted as a negative control. L-DOS47 showed a much higher binding affinity than AFAIKL2 antibody due to higher antibody avidity (6-10 antibodies) presented in L-DOS47. The result was further confirmed using L-DOS47 and AFAIKL2 antibody as competitors to inhibit the binding of ruthenium-tagged L-DOS47 to BxPC-3 cells (FIG. 2B). Both L-DOS47 and AFAIKL2 antibody inhibited the binding of ruthenium-tagged L-DOS47 to BxPC-3, and as expected, L-DOS47 demonstrated a better binding affinity and thus stronger inhibition of binding of ruthenium-tagged L-DOS47 to BxPC-3 than AFAIKL2 antibody. The apparent binding affinities of both L-DOS47 and AFAIKL2 antibody can be compared by the $IC_{50}$ (the amount of competitor required to cause 50% decrease in binding) of the test articles. The $IC_{50}$ of L-DOS47 and AFAIKL2 antibody were estimated to be 2 and 20 μg/mL, respectively; or 3.22 nM for L-DOS47 (MW=622k for a conjugation ratio of 6 antibodies to 1 urease) and 1.55 μM for AFAIKL2 (MW=12.9k). The results suggested that the binding affinity of L-DOS47 is about 500 times of that of the AFAIKL2 antibody.

Overexpression of Transfected CEACAM6 Gene in H23 Cells

After transfection with CEACAM6 gene, a positive clone H23-CC6 #7 was identified. Clones with CEACAM6 level closer to that of A549 cells were obtained by re-sorting the H23-CC6 #7 clone with L-DOS47-cy5.5. Further incubation of the clone with higher amount of G418 antibiotic (800 μg/mL) helped to select the one with higher level of CEACAM6 expression. Although H23-CC6 #7 expressed less CEACAM6 on the cell surface than A549 and BxPC-3 cells, this CEACAM6-transfected clone was even more susceptible than BxPC-3 cells to L-DOS47 cytotoxicity (FIG. 3B) due to its highly susceptibility to ammonia toxicity (data not shown).

CEACAM6 Gene Knockdown in BxPC-3 Cells

Binding of L-DOS47 to two CEACAM6 knockdown clones (HUSH #6 and HUSH #7) was significantly reduced as compared to that of native BxPC-3 cells and the control clone (HUSH-TR3) (FIG. 3C). The experiment clearly showed that the presence of CEACAM6 on the cell surface was important for L-DOS47 binding. Silencing the gene did substantially reduce the binding of L-DOS47.

Immunochemical Staining of Human Tumor Tissues by L-DOS47

Figure 4:
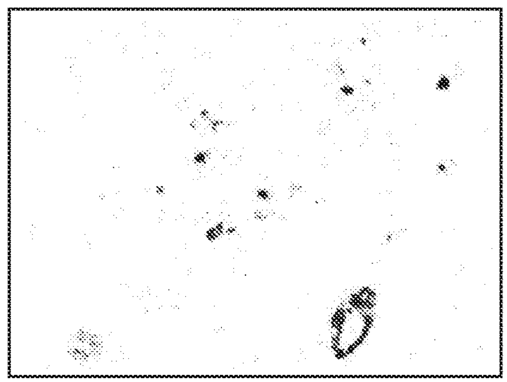
FIG. 4 depicts the immunohistochemical staining of human colon and lung adenocarcinoma with L-DOS47. Positive staining is shown in dark color.
Figure 4:
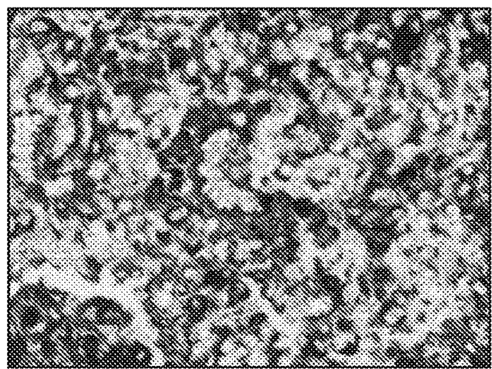

Normal and cancer tissue screening demonstrated that L-DOS47 recognized the adenocarcinoma subtype nearly exclusively (Table 2). Of the over 400 tissue samples screened, which represent 42 groups consisting of various cancerous and matched normal tissues, lung adenocarcinoma tissues showed considerable staining with over 80% of the cells being recognized. Corresponding age-matched normal lung tissues were negative with hints of focal staining in a few activated pneumocytes. The other tissues that showed some positive but weak staining were colon and pancreatic adenocarcinoma. FIG. 4 shows the immunochemical staining of colon and lung adenocarcinoma with L-DOS47.

TABLE 2

Human normal and cancer tissue screening of L-DOS47 binding

| | Tumor Tissue | | Age-matched Normal Tissue |
|---|---|---|---|
| Samples | Positive | Negative | Negative |
| Kidney carcinoma | | 12/12 | 12/12 |
| Parathyroid adenoma | | 1/1 | n/a |
| Placenta, umbilical cord, allantois | n/a | | 1/1 |
| Myofibroblastic tumor | | 1/1 | n/a |
| Prostate carcinoma | | 4/4 | 4/4 |
| Thyroid carcinoma | | 2/2 | 2/2 |
| Pancreas adenocarcinoma | 7/57 weak 8/57 v. weak | 42/57 | 25/25 |
| Neuroendocrine tumors | | 9/9 | n/a |
| Brain, heart muscle, testis, spleen | n/a | | 30/30 |
| Testis - teratoma and seminoma | | 3/3 | 3/3 |
| Parotis tumor | | 1/1 | 1/1 |
| Cervix squamous carcinoma | | 2/2 | n/a |
| Thymoma | | 2/2 | n/a |
| Colon adenocarcinoma | 14/24 weak | 10/24 | 24/24 |
| lymph node metastasis | | 3/3 | |
| Breast adenocarcinoma | | 13/13 | 13/13 |
| lymph node metastasis | | 2/2 | |
| Leiomyoma - lung metastasis | | 1/1 | n/a |
| Ovary carcinoma | | 4/4 | n/a |
| Bladder carcinoma | | 42/42 | 36/36 |
| lymph node metastasis | 1/1 strong | | |
| squamous carcinoma | | 2/2 | |
| metastasis | | | |
| Lung - small cell carcinoma | | 1/1 | 5/5 |
| adenocarcinoma | 5/5 strong | | |
| Stomach adenocarcinoma | | 3/3 | 3/3 |
| Liver carcinoma | | 4/4 | 4/4 |
| Soft tissue tumors | | 3/3 | n/a |
| Melanoma | | 48/48 | 18/18 |
| metastasis | | 18/18 | |

Immunohistochemical staining of human colon and lung adenocarcinoma with L-DOS47 are as shown in FIG. 4.

A549 Metastasis Study

At 3 weeks, mice receiving A549 cells treated with 10 and 15 μg/ml of L-DOS47 showed decreased lung tumor counts, demonstrating a significant decrease ($p<0.05$) as compared to the untreated control group (Table 3). However, no significant decreases in the mean number of tumor cell counts were noted at 10 weeks. Although not statistically significant, treatment with 10 μg/ml L-DOS47 at both 3 and 10 weeks post-treatment showed a consistent decrease in the number of mean tumor cells in comparison to the untreated control group (Table 3). Interestingly, the isotype control (V21-DOS47) also affected and reduced the number of tumor count in the lung. In summary, treatment of A549 cells with L-DOS47 at 10 μg/mL reduced the mean number of lung tumors at 3 weeks post-treatment, but this effect was transient since no significant decreases in mean tumor number were observed by 10 weeks post-treatment.

TABLE 3

Mean number of counted lung tumors in A549 metastasis study

| Group | Cell Treatment | Final Concentration (μg/mL) | Mean number of lung tumors# 3 weeks | Mean number of lung tumors# 10 weeks |
|---|---|---|---|---|
| 1 | Untreated | — | 103.8 ± 30.0 | 110.6 ± 50.0 |
| 2 | Isotype | 10 | 44.6 ± 5.1 | 60.4 ± 14.3 |
| 3 | L-DOS47 | 10 | 28.0* ± 7.2 | 50.0 ± 17.7 |
| 4 | L-DOS47 | 15 | 18.2* ± 7.8 | 112.2 ± 52.5 |

Mean ± sem;

*$p < 0.05$ when compared to the untreated control group.

As shown in Table 3, A549 human lung adenocarcinoma cells were treated with L-DOS47 or isotype control (V21-DOS47) in vitro. After incubation at 37° C. for 4 hours, the cells were washed 3 times with PBS and resuspended in PBS at $1\times10^7$ cells/mL. Each mouse then received a single inoculation of $1\times10^6$ treated cells. Five animals per group were euthanized at 3 weeks and 10 weeks post injection. The effect of the test article on tumor metastasis was determined by counting the number of metastatic tumors in each lung under a dissecting microscope. Metastatic tumor growth in the L-DOS47 treated group was compared to the untreated control group by unpaired t test. Co-injection with L-DOS47 at 3 weeks post-treatment has significantly reduced the number of tumor counts.

Figure 1:
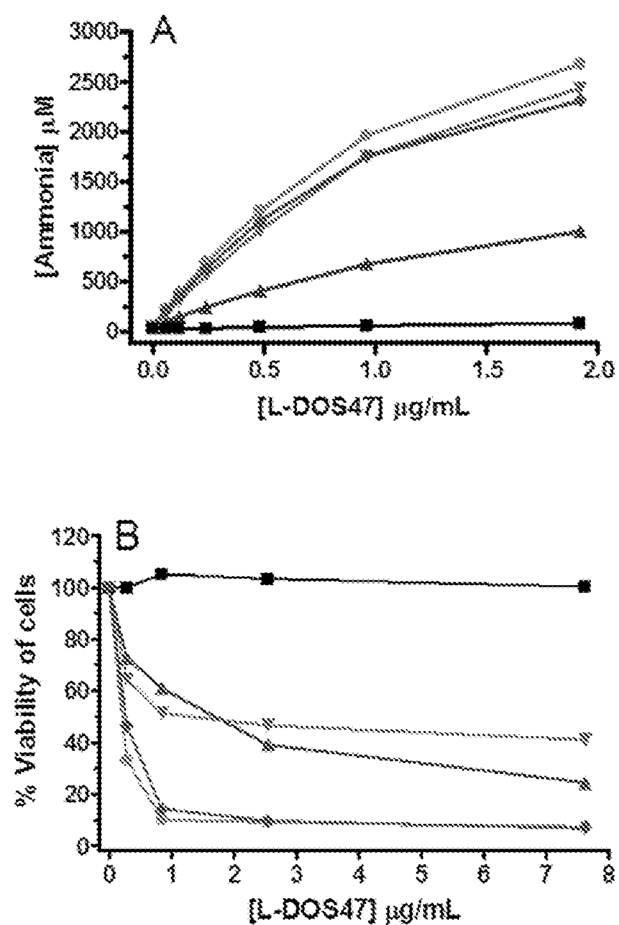
FIG. 1A-B depicts exemplifying binding and cytotoxicity studies of L-DOS47 in cancer cell lines. (A) Direct binding of L-DOS47 to five cancer cell lines: BxPC-3, Capan-1, ZR-75-30, LS174T, and MDA-MB231. The binding signal was represented by the amount of ammonia generated upon incubation with 20 mM urea. Good L-DOS47 binding was observed in BxPC-3 (●), Capan-1 (▼), and ZR-75-30 (♦) cells, whereas moderate binding was observed in LS174T cells (▲) and no binding was found in MDA-MB231 cells (■). In addition, no binding was observed with the unconjugated DOS47 control on corresponding cell lines (data not shown), suggesting that L-DOS47 binding was specific and was contributed by the antibody moiety. (B) L-DOS47 induced cytotoxicity on the cancer cell lines upon addition of 20 mM urea. No effects was observed in MDA-MB231 cells (■), which agreed with the binding study. BxPC-3 (●) and ZR-75-30 (♦) were highly susceptible to L-DOS47, whereas only moderate effects were found in Capan-1 (▼) and LS174T cells (▲).
Figure 2:
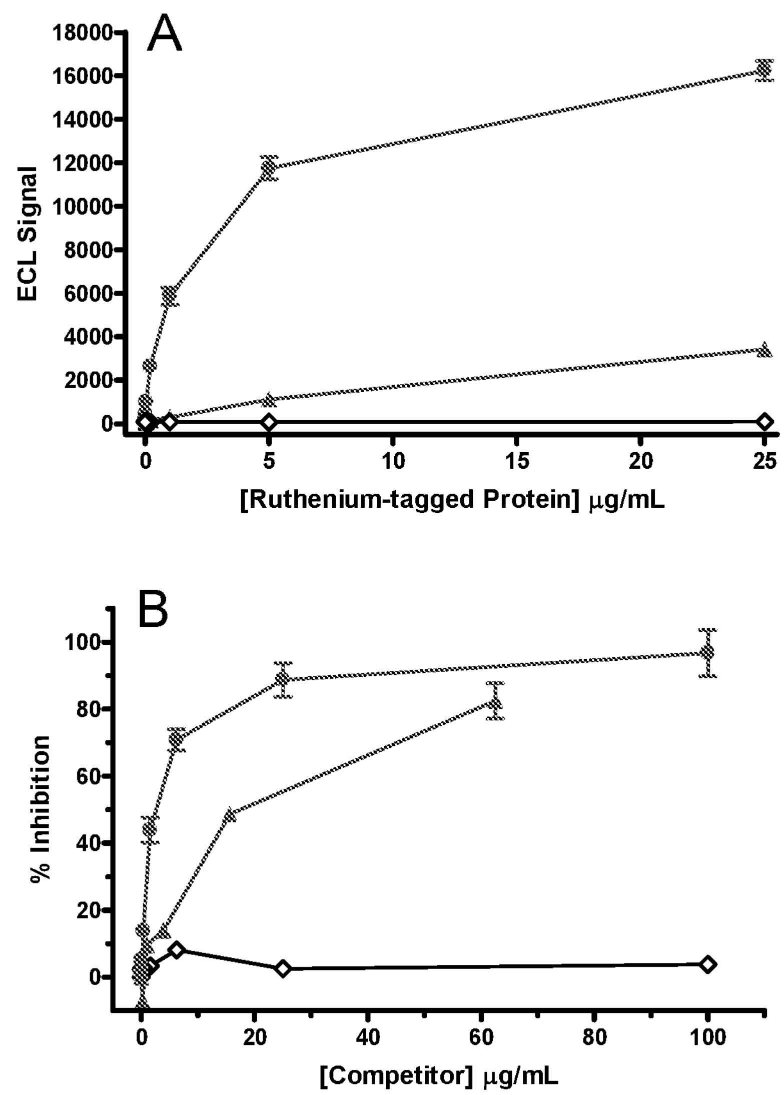
FIG. 2A-B depicts exemplifying direct and competitive binding of L-DOS47, DOS47, and AFAIKL2 antibody to BxPC-3 cells. (A) Binding of ruthenium-tagged L-DOS47, AFAIKL2 antibody, and unconjugated DOS47 to BxPC-3 cells. The electrochemiluminescence assay provides a direct measurement of L-DOS47 and AFAIKL2 antibody binding to BxPC-3 cells. Weak binding signal was observed with the AFAIKL2 antibody (▲), while L-DOS47 showed much stronger binding signal (●) due to the avidity of multiple AFAIKL2 antibodies presented on the antibody conjugate. No binding was observed with the negative control DOS47 (◇). (B) The binding of L-DOS47-tag to BxPC-3 cells was competed with either L-DOS47, AFAIKL2 antibody, or DOS47. The apparent binding affinities of both L-DOS47 and AFAIKL2 antibody can be compared by the $IC_{50}$ (the amount of competitor required to cause 50% decrease in binding) of the test articles. The $IC_{50}$ of L-DOS47 (●) and AFAIKL2 antibody (▲) were estimated as 2 and 20 μg/mL (or 3.22 nM and 1.55 μM), respectively, indicating that the binding affinity of L-DOS47 is about 500 times of that of AFAIKL2 antibody. No inhibition was observed with the negative control DOS47 (◇). The results represent the mean (n=3) of representative experiments.
Figure 3:
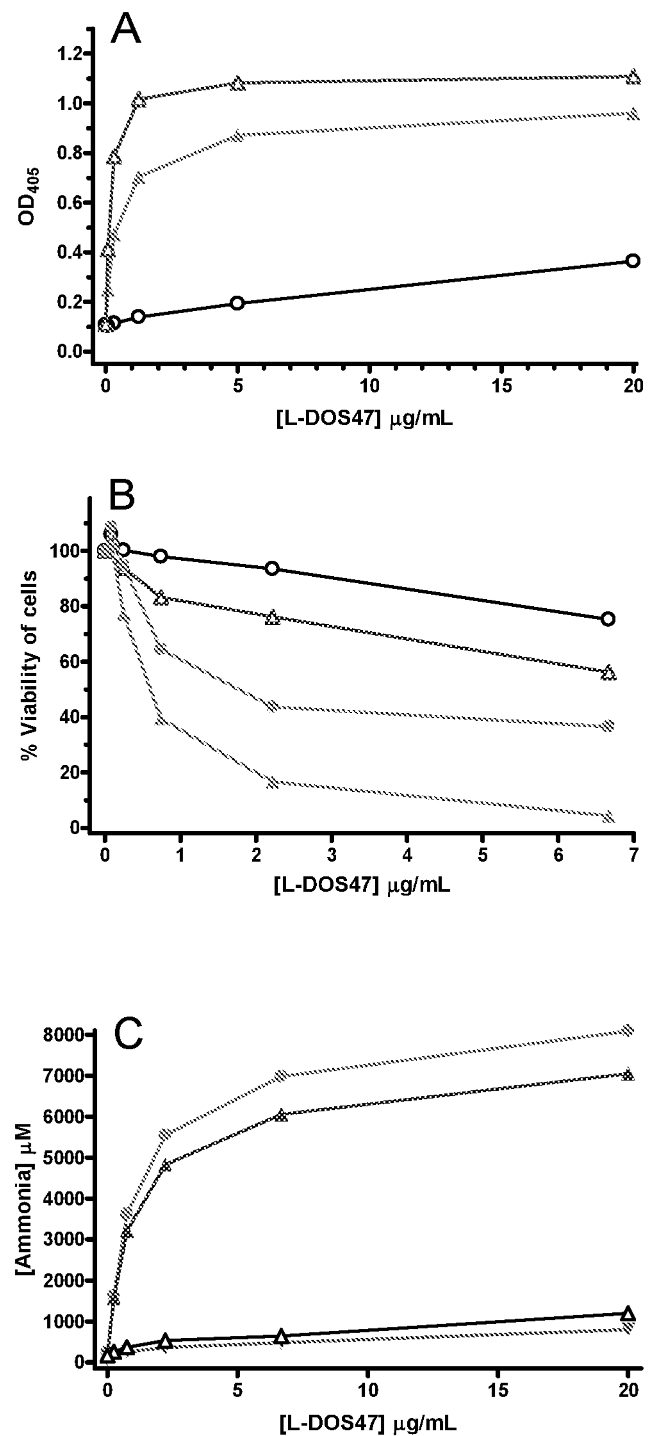
FIG. 3A-C depicts exemplifying overexpression and knockdown of CEACAM6 gene. (A) Binding of L-DOS47 to CEACAM6-transfected H23 cells. The population of the transfected cell line (▲) was enriched by FACS cell sorting together with an increased amount of selection antibiotic. The binding profile as compared to that of the native H23 cells (○) and A549 cells (Δ) showed that CEACAM6 was expressed in the transfected cells at a level lower than that of A549 cells. (B) Cytotoxicity assay of L-DOS47 on CEACAM6-transfected H23 cells. CEACAM6 overexpression in H23 cells (▲) has greatly enhanced their susceptibility to L-DOS47 cytotoxicity as compared to BxPC-3 (●), A549 (Δ), and native H23 (○) cells. Interestingly, the transfected H23 cells were more susceptible to L-DOS47 cytotoxicity than both A549 and BxPC-3 cells, despite weaker L-DOS47 binding was observed in (A). (C) Binding of L-DOS47 to BxPC-3 cells with CEACAM6 gene knocked down. Good binding signal was observed in the native (●) and control (HUSH-TR3 ▲) BxPC-3 cells. However, L-DOS47 binding was lost as the CEACAM6 gene was silenced by shRNA (HUSH #6 ▼ and HUSH #7 Δ), suggesting that CEACAM6 is the surface antigen being recognized by the antibody conjugate. The results represent the mean (n=3) of representative experiments. The standard deviation (SD) was less than 10% for all values.

The use of urease as a potential cancer therapeutic based on ammonia production and local pH elevation mediated by the enzyme was demonstrated (8). However, the lack of selectivity of the enzyme for tumor cells over normal cells has limited its application as cancer therapeutic. The application of antibody-drug conjugate (ADC) or more specifically, antibody-directed enzyme prodrug therapy (ADEPT) of this technology can circumvent this limitation. In this example, a specific form of antibody-urease conjugate (L-DOS47) was made by conjugating CEACAM6-specific llama single domain antibody (AFAIKL2) to urease (DOS47). The conjugated AFAIKL2 antibodies provide the specificity and thus enhance the efficacy of the urease enzyme towards CEACAM6-expressing tumors. The specificity of L-DOS47 for cancer cells expressing CEACAM6 on the cell surface was assessed through in vitro binding studies (FIGS. 1 and 2). The results of these studies demonstrated that L-DOS47 bound to CEACAM6-expressing cell lines (BxPC-3, Capan-1, ZR-75-30, and LS174T), but not to non-expressing cell line (MDA-MB231). In addition, the functional role of CEACAM6 was confirmed by CEACAM6 knockdown and overexpression experiments in cancer cells (FIG. 3). CEACAM6 was overexpressed by transfecting CEACAM6-encoded plasmid into H23 cells, while gene knockdown was performed by small hairpin RNA-mediated depletion of CEACAM6 in BxPC-3 cells. Binding studies showed that L-DOS47 bound to native BxPC-3 cells with high affinity but not to BxPC-3 cells with CEACAM6 gene knocked down (FIG. 3C). In contrast, overexpression of CEACAM6 in H23 cells has rendered the cells susceptible to L-DOS47 binding and cytotoxicity (FIGS. 3A and 3B). These results showed that specific binding of L-DOS47 to CEACAM6 antigen is important for the antibody conjugate to induce tumor cytotoxicity. Another benefit of conjugating antibodies to urease over individual antibody is an overall increase in avidity. The ECL binding assays showed that L-DOS47 with a molar conjugation ratio of 6-10 antibodies to 1 urease bound 500 times better than single antibody to BxPC-3 cells (FIG. 2B). Further binding studies has suggested that an antibody to enzyme conjugation ratio of greater than 6:1 is optimum for L-DOS47 binding to CEACAM6 (Data not shown).

The mechanism of action was investigated through in vitro and in vivo studies. Urease is the active component of L-DOS47 and previous studies have demonstrated that urease is cytotoxic to human tumor cells in vitro (8). Intratumoral administration of urease to A549 (lung) and MCF-7 (breast) tumors in nude mouse significantly inhibited tumor growth (8). However, the cytotoxic efficacy of urease or L-DOS47 also relies on the susceptibility of the tumor cell lines to ammonia. For instance, in FIG. 1A, L-DOS47 bound about equally well to BxPC-3, ZR-75-30, and Capan-1, but Capan-1 showed moderate cytotoxic response as compared to the other two cell lines (FIG. 1B). Capan-1 is less susceptible to ammonia cytotoxic effect as compared to BxPC-3 and ZR-75-30 (data not shown). Similarly, the human lung adenocarcinoma H23 cells are sensitive to the presence of ammonia; once transfected with CEACAM6 gene, the cell line became susceptible to L-DOS47 cytotoxicity (FIG. 3B) despite less CEACAM6 antigens were presented on the cell surface as compared to BxPC-3 (data not shown) and A549 cells (FIG. 3A). In conclusion, for L-DOS47 to exert cytotoxic effects on a tumor, CEACAM6 expression on the cell surface and susceptibility to ammonia are two important requirements.

Immunohistochemical screening of human cancer tissues showed that L-DOS47 was specific to lung, colon, and pancreatic adenocarcinoma (Table 2) but not to corresponding normal tissues. Conjugation of multiple antibodies on the surface of urease has greatly enhanced the specificity towards CEACAM6 antigen (FIGS. 1A and 2) and reduced the non-specific binding nature of the enzyme (data not shown). In vivo studies further confirmed the efficacy of L-DOS47 against tumor xenograft. Tumor growth inhibition was observed in IV administration of L-DOS47 to nude mouse tumor xenograft (data not shown) and metastasis study of A549 lung adenocarcinoma (Table 3). Significant reduction of pulmonary foci was observed in A549 cells treated with 10 or 15 μg/mL L-DOS47 3 weeks post injection (Table 3). However, no significant difference was found after 10 weeks, possibly due to the clearance of L-DOS47 from the animal. The isotype control (V21-DOS47, an anti-VEGFR2-DOS47 conjugate) also caused some degrees of pulmonary foci reduction, despite the fact that A549 cells do not express VEGFR2 under normal condition. Ohwada et al (19) reported that VEGFR functionality was induced in A549 cells after exposure with 50 mM HCl. The suppressed proliferation of the distressed A549 cells could be restored by exogenous VEGF administration, while addition of neutralizing anti-VEGFR1 and anti-VEGFR2 antibodies re-suppressed cell proliferation. However, both VEGF and anti-VEGFR antibodies had no effects on the control cells. Without wish being bound by theory, it is possible that VEGFR2 functionality in A549 cells may be induced during the cell preparation process in this metastasis study. This explains why cell count reduction was observed in the isotype control group. The results from both in vitro and in vivo studies have demonstrated that antibody conjugation on urease enables the antibody-conjugate to specifically target CEACAM6-expressing tumors with good selectivity and efficacy, which provides proof-of-concept for the clinical development of L-DOS47.

Example 2. A Dose Escalation Study of L-DOS47 in Recurrent or Metastatic Non-Squamous NSCLC (Non-Small Cell Lung Cancer)

The primary purpose of this research study is to evaluate how safe, how well tolerated and how effective a range of doses of L-DOS47 in combination with standard doublet therapy of pemetrexed/carboplatin in patients with Stage IV (TNM M1a and M1b) recurrent or metastatic non-squamous Non-Small Cell Lung Cancer.

Primary outcome measures are as follows. Number of patients with adverse events as a measure safety and tolerability of L-DOS47 in combination treatment with pemetrexed/carboplatin is that participants will be followed for 12 weeks. It is designated as safety issue. The AE reporting period starts on Cycle 1 Day 1 up to the last study visit. Secondary outcome measures are as follows. Objective response rate of patients receiving the combination treatment according to RECIST 1.1 is up to 12 weeks, and is not designated as safety issue. Objective tumor response will be assessed according to RECIST version 1.1 in patients who have completed at least 2 cycles of study treatment and who have at least 1 post-treatment disease assessment. Number of patient receiving a sustained clinical benefit is followed up to 12 weeks, and is not designated as safety issue. Defined as the percentage of patients who have achieved complete response, partial response, and stable disease following combination treatment with L-DOS47+pemetrexed/carboplatin. Maximum observed plasma concentration (Cmax) of L-DOS47 after dosing in combination treatment with pemetrexed/carboplatin is up to 12 weeks, and is not designated as safety issue. Pharmacokinetic parameters for L-DOS47 will be determined from plasma samples collected from all patients dosed with L-DOS47. Time to maximum observed plasma concentration (Tmax) of L-DOS47 after dosing in combination treatment with pemetrexed/carboplatin is up to 12 weeks, and is not designated as safety issue. Pharmacokinetic parameters for L-DOS47 will be determined from plasma samples collected from all patients dosed with L-DOS47. Area under the concentration (AUC) vs time curve of L-DOS47 after dosing in combination treatment with pemetrexed/carboplatin is up to 12 weeks, and is not designated as safety issue. Pharmacokinetic parameters for L-DOS47 will be determined from plasma samples collected from all patients dosed with L-DOS47. Terminal elimination half-life of L-DOS47 after dosing in combination treatment with pemetrexed/carboplatin is up to 12 weeks, and is not designated as safety issue. Pharmacokinetic parameters for L-DOS47 will be determined from plasma samples collected from all patients dosed with L-DOS47. The presence of anti-L-DOS47 antibodies for patients dosed with L-DOS47 in combination treatment with pemetrexed/carboplatin is up to 12 weeks, and is designated as safety issue. Serum samples will be collected and analyzed from all patients dosed with L-DOS47.

Experiments involving Pemetrexed and Carboplatin plus L-DOS47 will be conducted. Patients will be recruited into cohorts of L DOS47 escalating doses, with a minimum of 3 and a maximum of 6 patients per cohort. The starting dose of L DOS47 will be 0.59 μg/kg; further possible dose levels that may be assessed are 0.78, 1.04, 1.38 and 1.84 μg/kg. The standard of care doses of pemetrexed [500 mg/m2] and carboplatin [AUC6], respectively, to be administered in combination with L-DOS47, will remain constant across cohorts. A treatment cycle will be 21 days, with patients receiving L DOS47 on cycle Days 1, 8, and 15 and pemetrexed/carboplatin on Day 1 of each treatment cycle. It is planned that patients will receive 4 cycles of combination treatment with L-DOS47+pemetrexed/carboplatin. Patients who have not progressed following the 4 cycles of combination treatment and who have not experienced unacceptable toxicity will have the opportunity to continue to receive L-DOS47 treatment for as long as there is clinical benefit and it is well-tolerated, in the opinion of the Investigator, until disease progression. Patients who are unable to complete 4 cycles of L-DOS47+pemetrexed/carboplatin combination treatment due to pemetrexed/carboplatin toxicity will have the opportunity to continue receiving L-DOS47 treatment following discontinuation of pemetrexed/carboplatin, for as long as there is clinical benefit and it is well-tolerated, in the opinion of the Investigator, until disease progression.

Example 3. A Phase I/II Open-Label, Non-Randomized Dose Escalation Study of Immunoconjugate L-DOS47 for Treating Non-Small Cell Lung Cancer The primary purpose of this research study is to evaluate how safe, how well tolerated and how effective a range of doses of L-DOS47 in patients with non-squamous non-small cell lung cancer when given as a monotherapy.

Primary outcome measures are as follows. The incidence and severity of drug-related adverse events as a measure of safety and tolerability of L-DOS47 are up to 12 weeks, and are designated as safety issue. These are assessed during the AE reporting period starts on Cycle 1 Day 1 up to the last study visit.

Secondary outcome measures are as follows. L-DOS47 related toxicity during the first 2 hours after infusion is during the first 2 hours after infusion, and is designated as safety issue. These are assessed by the incidence and severity of AEs and SAEs and changes in vital signs. The incidence and severity of all reported adverse events and serious adverse events are under the time Frame that Participants will be followed for 12 weeks and the 30 days follow-up period. These are designated as safety issue and are assessed during the AE reporting period starts on Cycle 1 Day 1 up to the last study visit. Changes from baseline for additional safety parameters (clinical laboratory assessments, vital signs, weight, oxygen requirement and 12-lead ECG are under the time frame up to 12 weeks, and are designated as safety issue. Safety parameters include clinical laboratory assessments, vital signs, weight, oxygen requirement and 12-lead ECG. The evaluation of anti-L-DOS47 antibody over time is up to 12 weeks, and is designated as safety issue. Serum samples will be collected and analyzed from all patients dosed with L-DOS47.

Other outcome measures are as follows. Maximum observed plasma concentration (Cmax) of L-DOS47 at each dose level is under the time frame of up to 12 weeks, and is not designated as safety issues. Pharmacokinetic parameters for L-DOS47 will be determined from plasma samples collected from all patient dosed with L-DOS47. Time to maximum observed plasma concentration (Tmax) of L-DOS47 at each dose level is up to 12 weeks, and is not designated as safety issue. Pharmacokinetic parameters for L-DOS47 will be determined from plasma samples collected from all patient dosed with L-DOS47. Area under the concentration (AUC) vs time curve of L-DOS47 at each dose level is measured up to 12 weeks, and not designated as safety issue. Pharmacokinetic parameters for L-DOS47 will be determined from plasma samples collected from all patient dosed with L-DOS47. Terminal elimination half-life of L-DOS47 at each dose level is under the time frame of up to 12 weeks, and not designated as safety issue. Pharmacokinetic parameters for L-DOS47 will be determined from plasma samples collected from all patient dosed with L-DOS47. Patient will be recruited into cohorts of L-DOS47 escalating doses, with a minimum of 3 and a maximum of 6 patients per cohort. The starting dose of L-DOS47 will be 0.12 μg/kg; further possible dose levels include 0.21, 0.33, 0.46, 0.59, 0.78, 1.04, 1.38, 1.84, 2.45, 3.26 and 4.33 Kg/kg. A treatment cycle will be 21 days with patients receiving L-DOS47 on cycle Days 1 and 8.

Patients will be recruited into cohorts, with a minimum of three and a maximum of six patients per cohort. All patients at a given dose level must complete Cycle 1 (3 week period) before escalation in subsequent patients can proceed. The decision for dose escalation to the next dose level will be made after the safety and available pharmacokinetic (PK) data have been reviewed by the Trial Steering Committee (TSC). Escalation of L-DOS47 will continue until a maximum tolerated dose (MTD) is reached. After the MTD of L-DOS47 has been determined in Phase I, up to 20 patients will be enrolled (taken forward from Phase I) to evaluate the preliminary efficacy of L-DOS47 (i.e., response rate using the Response Evaluation Criteria in Solid Tumours [RECIST] version 1.1 criteria, disease progression and survival); monitoring will include radiologic evaluations every second cycle. The safety and tolerability of L-DOS47 will also be further evaluated. Pharmacokinetic information will be collected as well as relevant observations on the activity of L-DOS47.

For all patients, treatment with L-DOS47 will continue either until the patient experiences disease progression, unacceptable toxicity, the patient withdraws consent or has completed four treatment cycles and does not wish to continue with additional cycles, whichever occurs first. After four cycles, patients may continue to receive L-DOS47 for as long as there is sustained clinical benefit and it is well tolerated, in the opinion of the Investigator.

Example 4: Production and Characterization of a Camelid Single Domain Antibody-Urease Enzyme Conjugate for the Treatment of Non-Small Cell Lung Cancer (NSCLC)

The effectiveness of the most commonly used cancer chemotherapeutic drugs is limited by their narrow therapeutic indices and lack of selective effects on tumor cells. Antibody directed enzyme prodrug therapy (ADEPT) improves selectivity by delivering antibody-enzyme conjugates to tumor sites where they bind to tumor associated antigens while the remaining unbound conjugates are eliminated from the bloodstream [20]. Once the antibody-enzyme conjugates accumulate, prodrug is administered and is converted at the tumor site to its active cytotoxic form by the enzyme portion of the antibody-enzyme conjugate, thus achieving selective tumor cell death. Since the ADEPT concept was introduced by Bagshawe in 1987 [20-22], researchers have applied variations of this concept to develop more potent and specific anti cancer drugs. [22-24]. Different generations of galactosidic prodrugs and antibody-galactosidase conjugates were developed in order to reduce systemic toxicity while increasing cytotoxicity of the activated drug [25]. Mutated forms of human purine nucleoside phosphorylase were engineered to enhance the specificity for adenosine-based prodrugs as substrate [26]. In addition, different types of immunoenzyme infusion proteins have been developed to improve enzyme activity and antibody avidity [27-29].

The manufacturing and characterization of L-DOS47 are described, which is a chemical conjugate of a single-domain recombinant antibody and jack bean urease with a conjugation ratio of about 10 antibodies per native urease molecule. The L-DOS47 immunoconjugate uses urea, which is naturally abundant in tumor tissues, as the prodrug to produce ammonia. Selective binding of the AFAIKL2 antibody to tumor associated antigen CEACAM6 [33] on target tumor cells results in the accumulation of urease and consequent hydrolysis of extracellular urea to produce ammonia, which is cytotoxic and creates an alkaline environment unfavorable to cancer cells [34]. Due to the complexity and the size of the conjugate, which can have a molecular weight up to 680 kDa, the conjugation chemistry, reaction and separation procedures were developed to address the challenges in large-scale production. Since urease has multiple potential conjugation sites for the selected antibody, the conjugation ratio of L-DOS47, which is essential to drug potency, was characterized using an Experion SDS micro-channel gel electrophoresis system [31,32]. L-DOS47 conjugate purity was determined by size exclusion chromatography. The chemical identity of L-DOS47 was characterized by mass spectrometric peptide mapping and Western blot. Because a primary amine (K32) is carried on the CDR3 region of the single-domain antibody, the distribution of the conjugation sites at the antibody side was determined by RP-HPLC and MALDI mass spectrometry. The conjugation sites for both the antibody and urease sides were also characterized by ESI mass spectrometry. The effect of conjugation ratio on the affinity of L-DOS47 binding for CEACAM6 was evaluated by ELISA. In vitro studies were performed to confirm L-DOS47 binding and its ability to cause cytotoxicity in CEACAM6-expressing cancer cell lines.

An immunoconjugate (L-DOS47) was developed and characterized as a therapeutic agent for tumors expressing CEACAM6. The single domain antibody AFAIKL2 which targets CEACAM6 was expressed in the *E. coli* BL21 (DE3) pT7-7 system. High purity urease (HPU) was extracted and purified from jack bean mills. AFAIKL2 was activated using N-succinimidyl[4-iodoacetyl] aminobenzoate (SIAB) as the cross-linker then conjugated to urease. The activation and conjugation reactions were controlled by altering pH. Under these conditions, the material ratio achieved conjugation ratios of 8-11 antibodies per urease molecule, the residual free urease content was practically negligible (<2%) and high purity (>95%) L-DOS47 conjugate could be produced using only ultradiafiltration to remove unreacted antibody and hydrolyzed cross-linker. L-DOS47 was characterized by a panel of analytical techniques including SEC, IEC, Western blot, ELISA and LC-$MS^E$ peptide mapping. As the antibody-urease conjugate ratio increased, a higher binding signal was observed. However, the effect was less apparent at conjugation ratios higher than 6 antibodies per urease. The specificity and cytotoxicity of L-DOS47 was confirmed by screening in three cell lines (BxPC-3, A549, and MCF7). BxPC-3, a CEACAM6-expressing cell line was found to be most susceptible to L-DOS47. L-DOS47 is being investigated as a potential therapeutic agent in human Phase I clinical studies for non-small cell lung cancer (NSCLC).

Production of High Purity Urease intermediate Urease (referred to as crude urease or DOS47 hereafter) was procured from BioVectra Inc. (Charlottetown, PE Canada).

Prior to use in conjugation, crude urease was purified to remove jack bean matrix protein contaminants such as canavalin and concanavalin A. Crude urease was dissolved in high purity water and the pH was brought to 5.15 with 10 mM acetic acid, 0.2 mM EDTA (acetate-EDTA buffer) then filtered under vacuum using a slurry of Celite 503. The cake was washed with 10 mM sodium acetate, 1 mM EDTA, pH 5.15 and dried under vacuum. The urease-containing filtrate was cooled to 0-4° C. and fractionated by adding chilled ethanol to a final concentration of 25% (v/v). The mixture was stirred for 15 minutes then filtered under vacuum using washed Celite 503. The cake was washed with acetate-EDTA buffer containing 25% (v/v) ethanol then dried under vacuum.

Cakes were resuspended in acetate-EDTA buffer and the slurry was filtered through Celite under vacuum to collect the filtrate. The resulting cake was washed with acetate-EDTA buffer and dried under vacuum. The wash and the initial filtrate were filtered through a 0.65 μm capsule. This ethanol fractionated urease filtrate was concentrated ~2× using two Sartorius Sartocon 100000 Da MWCO polyethersulfone membranes followed by buffer exchange into acetate-EDTA buffer.

Imidazole and TCEP (Tris (2-carboxyethyl) phosphine hydrochloride) were added to this medium purity urease at final concentrations of 20 mM and 1 mM respectively and the pH was adjusted to 6.5. The protein solution was loaded onto a DEAE-Sepharose Fast Flow column pre-equilibrated with 20 mM imidazole, 1 mM TCEP, pH 6.5 (imidazole-TCEP buffer). All steps were performed at a flow rate of 500 mL/min. The column was washed with imidazole-TCEP buffer followed by imidazole-TCEP buffer containing 80 mM NaCl to remove unbound impurities. Urease was eluted with imidazole-TCEP buffer containing 180 mM NaCl. Fractions with $A_{280}$>0.1 and purity by SEC of ≥90-97% were pooled.

The pooled fractions were concentrated to a target protein concentration of 6-8 mg/mL using two Sartorious Sartocon 100 000 Da MWCO PESU membranes, then diafiltered against acetate-EDTA buffer containing 10 mM sodium acetate, 1 mM EDTA, pH 6.5. The yield from this step is typically >55% of the starting activity. Expression and purification of AFAIKL2 drug intermediate the amino acid sequence of the AFAIKL2 antibody is shown in FIG. 5 (SEQ ID NO. 1).

The antibody gene was expressed in *E. coli* BL21 (DE3) pT7-7 system. One vial of the master cell bank was aseptically inoculated through three seeding steps to 350 L Luria HiVeg (20 g/L) supplemented with 50 mg/L kanamycin, 1 g/L cerelose, 0.02 g/L $MgSO_4$, and 0.01% Biospumex antifoam reagent in a 500 L fermenter. The process was controlled to maintain the dissolved oxygen at >20%, the temperature at 37° C.±2° C., the back pressure between 5-20 psi, the pH at 7.0±0.2, the OD600 between 0.5-40, and the glucose concentration between 1-3 g/L. Once the culture reached an OD600 of 7-10, antibody expression was induced by the addition of IPTG to a final concentration of 1 mM and allowed to continue for 6-8 hours. The cells were harvested by centrifugation, washed and lysed to release the inclusion bodies, then resuspended in 10 volumes of 50 mM imidazole pH 6.8. The cell suspension was homogenized in batches and the homogenate was passed first through a 75 micron stainless steel sanitary screen then through a microfluidizer with a minimum pressure of 10,000 psi for a total of three passes while maintaining the temperature below 10° C. The cell lysate was centrifuged, the insoluble material was pooled and the pellet was resuspended with homogenization in 10 volumes of 1% Triton X-100 with 5 mM DTT. The washed pellet was collected by centrifugation. This wash was repeated and followed by two washes with 25 mM sodium acetate, pH 4.0 containing 5 mM DTT to remove residual Triton X-100 and to buffer the pellet to pH 4.

The pellet containing the washed inclusion bodies was resuspended in 8 M urea, 25 mM DTT, 125 mM sodium acetate, pH 4.0 then solubilized alternately with a Ross homogenizer then an overhead mixer until there was no further change in visual appearance, and then mixed with an overhead mixer alone for a total time of 3 hours. The solubilized inclusion bodies were centrifuged and the clarified supernatant was loaded at 550 mL/min onto a SP-Sepharose XL column that was pre-equilibrated with 8 M urea in 125 mM sodium acetate pH 4.0 (SP equilibration buffer). After the clarified supernatant was loaded, the column was washed with equilibration buffer until the eluate A280 dropped below 0.05, followed by 8 M urea in sodium acetate, pH 4.0 with 50 mM NaCl until the eluate A280 dropped below 0.05. The pump speed was reduced to 275 mL/min and 3 cv of 8 M urea containing 25 mM sodium acetate, 180 mM NaCl, pH 4.0 were applied to the column to elute the AFAIKL2. Fractions with an A280>0.4 and an A280/A260 ratio>1.5 were pooled and analyzed for purity and protein content. The percent yield from this step was typically 35-45%. The pooled material was diluted with SP equilibration buffer to ≤2.5 g/L, the pH was adjusted to 8.0 with 2 M Tris-Cl pH 8.0, DTT was added to 2.5 mM, and the conditioned pool was mixed for 60 minutes to fully reduce the denatured protein. The denatured protein solution was then diluted to a final protein concentration of less than 0.1 mg/mL in the refolding buffer containing 25 mM Tris-Cl, pH 8.5. The refolding was carried out at 2-8° C., and tracked by Ellman's assay and C18 reverse phase HPLC until the level of free sulfhydryl was <0.75 μM and only fully oxidized protein could be detected.

The refolded protein solution was loaded onto a Q-Sepharose XL column pre-equilibrated with 25 mM imidazole pH 6.8 and the column was washed with equilibration buffer until the A280 was <0.05, followed with 25 mM imidazole pH 6.8 containing 50 mM NaCl until the A280 was <0.01. The protein was then eluted with 25 mM imidazole pH 6.8 containing 150 mM NaCl and fractions were collected until the A280 was ≤0.3. Fractions were combined to create a target pool with not less than 97% purity and a yield of not less than 45%. The pool was then concentrated to 3-5 g/L using a UF/DF system with Hydrosart regenerated cellulose 5000 MWCO cartridges, followed by buffer exchange against 10 mM phosphate buffer pH 7.0 and lyophilization.

Conjugation Chemistry

Figure 6:
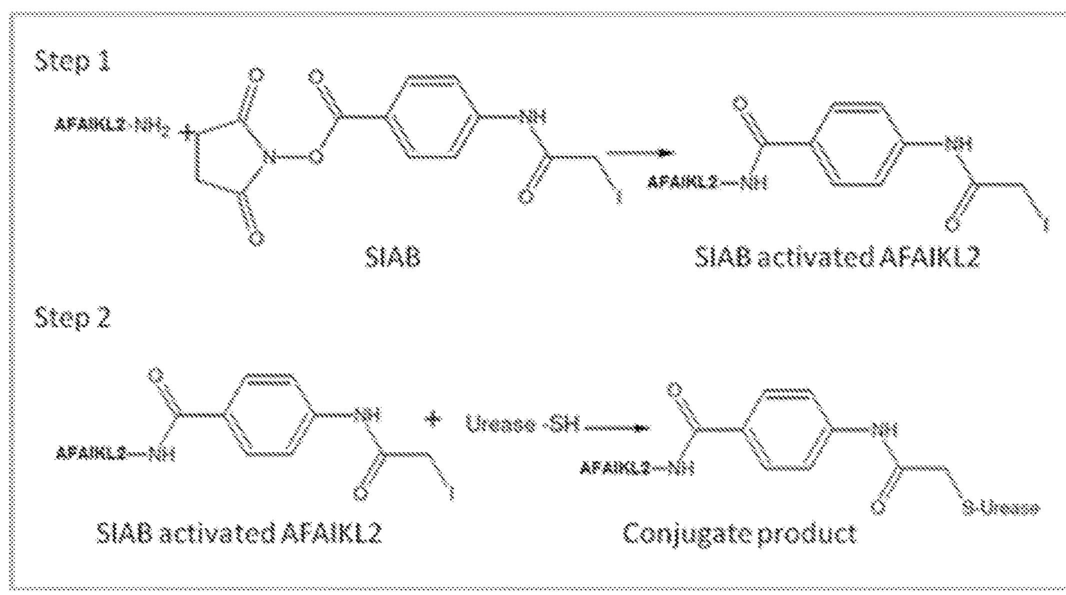
FIG. 6 exemplifies a synthesis of L-DOS47 conjugate product by a two-step reaction. Step 1 is an activation of antibody using SIAB, and Step 2 involves conjugation of the activated antibody with urease enzyme to form the bioconjugate L-DOS47.

The conjugation was carried out in two steps (FIG. 6). In the first step, primary amine groups on AFAIKL2 were activated by reaction with the NHS ester portion of SIAB. In the second step, the activated AFAIK2 was coupled to thiol groups on urease via the iodoacetamide end of SIAB. As shown in FIG. 6, synthesis of L-DOS47 conjugate product is a two-step reaction. Step 1 is an activation of antibody using SIAB and Step 2 involves conjugation of activated antibody with urease enzyme to form the bioconjugate L-DOS47.

Activation of AFAIKL2 antibody Lyophilized AFAIKL2 (25 g) was dissolved in water for injection (WFI). SIAB (2.00 g) was dissolved in anhydrous DMF and added to the AFAIKL2 solution in three equal aliquots with 60 minutes of stirring after each addition. One hour after the final addition of SIAB, any remaining unreacted NHS groups were quenched by addition of a 10× molar excess of glycine over the original amount of SIAB added. To remove the hydrolyzed and glycine quenched SIAB, the reaction solution was concentrated to 10 mg/mL AFAIKL2 using a Sartorious Sartocon 5000 Da MWCO followed by buffer exchange into 10 mM sodium acetate, pH 6.5, 1 mM EDTA.

Conjugation of activated antibody to urease High purity urease (50 g) was mixed with the activated AFAIKL2 in 10 mM sodium acetate pH 6.5, 1 mM EDTA. The pH was then brought to 8.3 by the addition of 1 M sodium borate pH 8.5, which allows the iodoacetyl group on the activated antibody to react with available cysteine residues on the urease. The reaction was allowed to proceed for 90 minutes with stirring. The unreacted iodoacetyl groups were then quenched by addition of 10× molar excess of cysteine over the original amount of SIAB added and the solution was mixed for 60 minutes. To remove unconjugated AFAIKL2, the L-DOS47 was concentrated to a target of 6 mg/mL using a 100 000 Da MWCO Sartorious Sartocon followed by buffer exchange into 10 mM L-histidine, pH 6.8, 0.2 mM EDTA. Sucrose was added to a final concentration of 1% w/v and the L-DOS47 was diluted to a target concentration of 1.8 g/L with 10 mM L-histidine, pH 6.8, 0.2 mM EDTA.

Size Exclusion Chromatography (SEC) for purity evaluation A Waters 2695 HPLC system with a 996 PAD was employed with Empower 2 software for data acquisition and processing. Chromatograms were recorded over 210-400±4 nm with the signal at 280 nm extracted for processing. Separation was performed on a Superose 6 100/300 GL column (GE). Proteins were eluted in 10 mM phosphate, 50 mM NaCl, 0.2 mM EDTA, pH 7.2. Separation was carried out with an isocratic flow at 0.5 mL/min after injection of 1000 of neat samples. The column was run at room temperature while the sample temperature was controlled at 5±2° C.

Ion Exchange Chromatography (IEC) for residual urease A Waters 2695 HPLC system with an 996 PAD and Empower software was employed. Chromatograms were acquired over 210-400 nm±4 nm with the signal at 280 nm extracted for processing. The column (Mono-Q 5/50 GL, GE) was run at room temperature while the sample temperature was controlled at 5±2° C. The elution buffers contained 50 mM acetate, 0.025% polysorbate 80 (super pure, HX2, NOF Corporation, Tokyo) with (Buffer B) or without (Buffer A) 0.70M NaCl, pH 5.50. The column was equilibrated with 15% Buffer B and 85% Buffer A for 6 min at 1 mL/min flow rate (6 CV) before samples were injected. After a wash cycle (15% Buffer B at 1.0 mL/min for 6 min), proteins were eluted by a gradient of 15-60% Buffer B in 20 minutes with a 0.5 mL/min flow rate. After cleaning with 100% Buffer B for 6 minutes at 1.0 mL/min, the column was re-equilibrated with 15% Buffer B before the next sample injection. 800 μl of neat L-DOS47 samples were spiked with HP urease reference standard to final percentages of 0-8% w/w and 50 μl/sample were injected. Peak height was used to calculate residual urease content using standard addition as the calibration method.

Experion SDS micro channel gel electrophoresis is used for determination of conjugation ratio. A BioRad Experion automated electrophoresis system and a BioRad SDS gel electrophoresis kit (Pro260 Kit) were employed to analyze L-DOS47 conjugation ratios. Samples were diluted with Tris-HCl buffer (10 mM, 0.2 mM EDTA, pH 7.0) to a target protein concentration of 0.5 mg/ml, then 4 μl diluted sample or molecular weight ladder was mixed with 2 μl sample buffer and briefly centrifuged. Samples were heated at 70° C. for 10 minutes then loaded onto the micro-channel chip after the system and channels were primed with gel-stain solution. Electropherograms were recorded automatically by the Experion software.

Western blot for identity characterization L-DOS47 test samples and AFAIKL2/HPU controls were resolved by SDS-PAGE gel electrophoresis then transferred to a nitrocellulose membrane using the Invitrogen iBlot system. Duplicate blots were made from gels run in parallel. Confirmation of AFAIKL2 identity requires detection using a rabbit anti-AFAIKL2 IgG primary antibody (Rockland) with secondary detection using a goat anti-rabbit IgG conjugated to alkaline phosphatase (AP)(Sigma). Confirmation of urease identity requires detection using a rabbit anti-urease IgG primary antibody (Rockland) with secondary detection using a goat anti-rabbit IgG conjugated to AP (Sigma). For detection using anti-AFAIKL2 IgG, L-DOS47 samples were diluted to 0.002 mg/mL in 1×TBS containing 0.1 mg/mL BSA then mixed 1:1 with protein gel loading buffer, heated to 70° C. for 10 minutes, and 0.01 μg of L-DOS47 was loaded per lane. For detection using anti-urease IgG, L-DOS47 samples were diluted to 0.02 mg/mL in 1×TBS containing 0.1 mg/mL BSA then mixed 1:1 with protein gel loading buffer, heated to 70° C. for 10 minutes, and 0.1 μg of L-DOS47 were loaded per lane. Final development of the Western blots was performed with AP buffer containing NBT/BCIP.

ELISA of L-DOS47 with Different Conjugation Ratios

To study the effect of conjugation ratio on the affinity of L-DOS47 binding to its targeting antigen CEACAM6, L-DOS47 conjugates with different conjugation ratios were produced at bench scale by adjusting the AFAIKL2/HPU molar ratios during conjugation. The conjugation ratios of the resulting conjugates were determined by SDS-Experion and protein concentrations were determined by micro Lowry using a Total Protein Kit (Sigma, TP0200). Microtiter plates were coated with 100 μL/well of CEACAM6-A, the domain-A of full CEACAM6 antigen (2.5 μg/ml in PBS) and incubated at room temperature for 6 hours. The plates were washed twice with Buffer A (0.05% BSA in PBS), blocked with 150 μL/well 3% BSA/PBS at 4° C. overnight, then washed twice with Buffer A. All subsequent steps were performed at room temperature with gentle shaking. L-DOS47 (100 μL/well) was added and incubated for 2 hours, the plates were washed 3 times with Buffer A then 100 μL/well of anti-urease IgG (1:12000, Rockland) was added and incubated for 1 hour. After three washes with Buffer A, 100 μL/well goat anti-rabbit IgG-AP (1:6000, Sigma) was added and incubated for 1 hour. After three washes with Buffer A, 100 μL/well AP substrate solution was added and incubated for 25 min. Absorbance was determined at 405 nm.

Determination of Activation Sites on AFAIKL2 Antibody

To prepare fluorescein-labeled cysteine (Cys-FL), cysteine was reacted in excess with NHS-ester fluorescein (Pierce) in 1M borate, pH 8.0 for 60 minutes at room temperature. The reaction solution was separated by RP-HPLC with a C8 column. The Cys-FL peak fraction was identified by MALDI mass spectrometry and its concentration was determined by spectrometry according to its extinction coefficient at 493 nm and pH 7. Peak fraction aliquots were lyophilized and stored in the dark at −20° C. The AFAIKL2 antibody was first activated with the SIAB cross-linker at bench scale and hydrolyzed SIAB was removed by a G25 desalting column prepared in-house. The activated antibody was allowed to react with the fluorescein-labeled cysteine (Cys-FL) in 100 mM borate buffer pH 8.3 for 90 minutes at room temperature. The reaction solution was buffer exchanged with 30 mM ammonium hydrogen carbonate by a G25 desalting column and the resulting AFAIKL2-Cys-FL was diluted to 0.5-0.8 mg/mL in 30 mM ammonium hydrogen carbonate containing 20% acetonitrile. Trypsin (Promega) was added to a final protein to trypsin ratio of 20:1 and the digestion was carried out at 37° C. for 36 hours. The resulting tryptic digest was reduced by adding 0.1M TCEP to a final concentration of 2 mM then separated by reverse phase HPLC (Agilent 1100 system with a Zobax 300SB-C18 column, 5 μm, 4.6×150 mm, gradient from 0 to 45% acetonitrile, 0.025% TFA in 55 minutes), and absorption was recorded at 420 nm. Because the SIAB activated lysine on AFAIKL2 was linked to the fluorescein labeled cysteine, it was not likely to be accessible by trypsin and the peptide ($X_nKX_m$)-Cys-FL should be generated. Peak fractions containing fluorescein modified peptides were collected and MALDI-mass spectrometry in Reflectron mode (Micromass Tof 2e) was applied. The HPLC peak areas of the corresponding peptides were used to calculate the distribution percentage of each activation site.

Peptide mapping and identification of conjugated peptides were done by ESI mass spectrometry. A Waters Xevo G2 QTOF mass spectrometer and an Acquity UPLC system H class with a BEH300 C18 column (1.7 μm, 2.1×150 mm) were employed. Each L-DOS47 sample (1.5-2.0 mg/mL, 50.0 μl) was mixed with 0.063±0.003 g guanidine-HCl. After the salt was fully dissolved, 1.50 μL of 0.7M DTT was added and the solution was incubated at 60° C. for 30 minutes. 10.0 μL of 0.20M iodoacetamide (IAA) was added and the pH was adjusted to 8.0-8.5 with saturated Tris-Base solution. The sample was incubated at 37° C. for 60 minutes. 50.0 μL of each alkylated sample was mixed with 15.0 μL of 0.1M $CaCl_2$ and 80.0 μL Tris buffer (50 mM Tris-HCl, pH 8.0), then 3.00 μL of 0.5 mg/ml trypsin solution was added. The tryptic digestion was carried out at 37° C. for 20-24 hours. After tryptic digestion, 50.0 μL of the digest was mixed with 0.50 μL neat formic acid for LC-MS analysis. The column temperature was set at 60° C. and Solvent A (0.075% v/v formic acid in water) and Solvent B (0.075% formic acid in acetonitrile) were used for UPLC separation. The UPLC was performed with a flow rate of 0.15 mL/min with a gradient from 0 to 55% Solvent B in 80 minutes.

LC-MS analysis was controlled by Masslynx V4.1 software. LC-$MS^E$ TIC (total ion counts) data acquisition was carried out in an M/Z range of 50-2000 Da in resolution mode with a scan rate of 0.3/s, capillary voltage 3.0 kV, sample cone voltage 25V, extraction cone voltage 4.0 kV. The high energy collision induced fragmentation TIC data acquisition was performed with collision energy ramped from 20 to 40V. Ion source temperature was set at 100° C., and desolvation temperature was set at 300° C. Desolvation gas flow was 600 L/hour. A real time lock mass TIC raw data set (scan/20 s) was acquired with 100 fmole/μL Glu-Fib B at a flow rate of 3.0 μL/minute.

Mass spectrometric raw data were processed with BioPharmalynx (v1.2) in peptide map mode with a resolution of 20000. A lock mass of 785.8426 Da was applied for real time point to point mass calibration. The low energy MS ion intensity threshold was set at 3000 counts, and the $MS^E$ high energy ion intensity threshold was set at 300 counts. Mass match tolerances were set at 15 ppm for both MS and $MS^E$ data sets. AFAIKL2 and urease amino acid sequences were input into the sequence library for peptide matching/identification. Variable modifiers including Deamidation N, Deamidation succinimide N, Oxidation M, Oxidation 2×M, +K, +Na, and a fixed modifier of Carbamidomethyl C (for alkylated cysteine) were applied for peptide map analysis. To identify the conjugated peptides on the AFAIKL2 side, the cysteine-containing peptides of urease plus the linkage section of cross-linker SIAB ($C_9H_7O_2N$, 161.0477 Da) were created as variable modifiers and included in the variable modifier library. In this case, Carbamidomethyl C was included as a variable modifier. To identify the conjugated peptides on the urease side, the lysine-in-middle peptides $X_nKX_m$ of AFAIKL2 plus the linkage section of SIAB were created as variable modifiers and included in the variable modifier library.

Whole-cell Binding Assay of L-DOS47

Cell monolayers were prepared by seeding 100 μL/well of MCF-7, BxPC-3, and A549 cells ($4\times10^4$ cells/well) in 96-well culture plates and incubating overnight at 37° C. Medium was then removed from the plates and the cell monolayers were fixed with 100 μL/well of 0.05% glutaraldehyde in PBS for 10 min at room temperature (RT). The plates were then washed with PBS and 120 μL/well of 50 mM glycine was added. After incubation at 37° C. for 20 min, the plates were blocked with 120 μL/well of 1% BSA/PBS at 37° C. for 30 min. The plates were then washed 3 times with Buffer A (0.05% BSA in PBS) and 80 μL/well of diluted L-DOS47 or DOS47 were added and incubated at 37° C. for 1.5 hours. The plates were washed 4 times with Buffer A and 80 μL/well of 20 mM urea in 0.1M PBS, pH 7.6 was added and incubated at 37° C. for 30 min. After incubation, 40 μL/well of 1N HCl was added to stop the reaction. The amount of ammonia produced in each well was determined using a modified indophenol assay. In brief, Solution A was freshly prepared by dissolving 165 mg phenol and 132 mg NaOH in 10 mL of water, followed by adding 66 μL sodium nitroprusside solution (10 mg/mL). Solution B was prepared by adding 40 μL sodium hypochlorite to 5 mL water. Sample solutions (30 μL each) from the whole-cell binding assay were transferred to a new 96-well plate containing 50 μL/well of 5N NaOH:$H_2O$ (3.3:46.7) and 20 μL/well water. Solution A (50 μL/well) and Solution B (50 μL/well) were added and the plates were then transferred to a microplate reader for color development at 37° C. for 30 minutes. OD was measured at 630 nm. The amount of ammonia produced in the wells was calculated from a calibration curve using 0 to 150 mM ammonium chloride as standards.

Cytotoxicity assay of L-DOS47 Cell monolayers were prepared by seeding 100 μL/well of MCF-7, BxPC-3, and A549 cells ($4\times10^4$ cells/well) in 96-well culture plates and incubating overnight at 37° C. Medium was then removed from the plates and 80 μL/well of diluted L-DOS47 or DOS47 were added and further incubated at 37° C. for 2 hours. After incubation, the plates were washed 3 times with KR-II buffer/0.05% BSA and 100 μL/well of 20 mM urea solution was added. The plates were incubated at 37° C. overnight then medium was removed and replaced with 100 μL/well plain medium. Cell viability was determined using a MTS cell viability assay, in which a 21:1 v/v solution of MTS/PES (MTS, 2 mg/mL; PES, 1 mg/mL) was prepared and 20 μL/well of the mixture was added to the plates. The plates were then incubated at 37° C. for 1 hour and OD was measured at 630 nm with reference at 490 nm.

Figure 7:
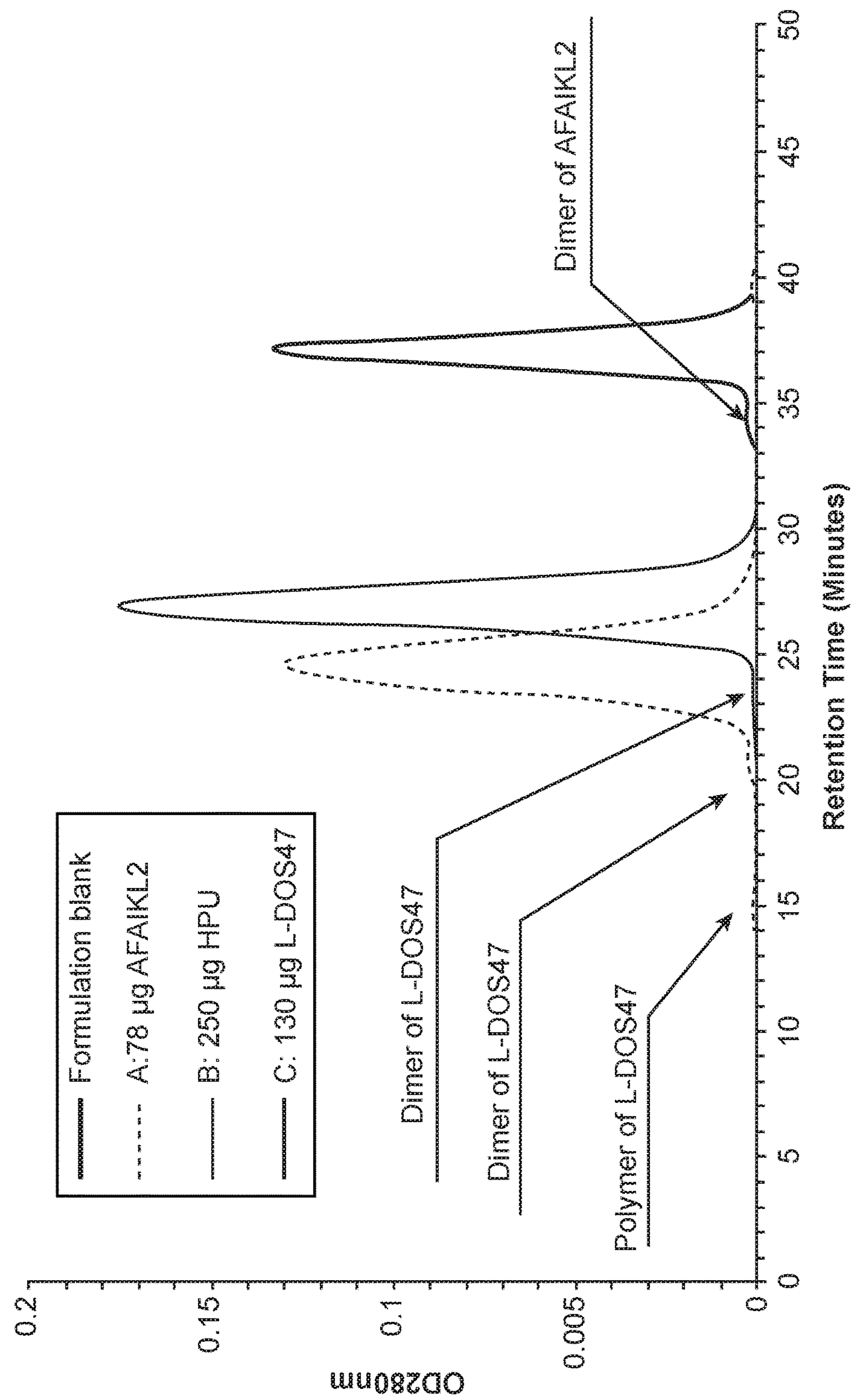
FIG. 7 depicts exemplifying size exclusion chromatograms of formulation blank, AFAIKL2, high purity urease (HPU) and conjugate L-DOS47. A very small peak for dimer for each constituent appears in front of the respective monomer peaks. Formulation blank contains 10 mM histidine, 1% sucrose, 0.2 mM EDTA, pH 6.8.

Jack bean urease is a hexameric enzyme consisting of six identical subunits of approximately 91 kDa each with 15 unbonded cysteine residues per subunit. The AFAIKL2 antibody contains seven primary amines and a disulfide bond. The primary amines on the antibody and the cysteine residues on the urease are the bases for chemical conjugation through a heterobifunctional cross linker. However, the molecular size of the conjugate and the nature of the two proteins created challenges in scale-up production, purification, and characterization of the conjugate product. The immunoconjugate must be soluble and stable in aqueous media near physiological pH for use as parenteral drug; therefore, the isoelectric point (pI) of the recombinant antibody required careful sequence design since urease is extracted from a plant source and its pI (observed pI 4.8-5.1) could not be altered. Optimization to ensure reaction uniformity and removal of residual reactants and side products was critical to conjugation chemistry. Though several cross linkers [24, 30] are widely used for protein conjugations and were screened during development, N-succinimidyl[4-iodoacetyl] aminobenzoate (SIAB) was chosen for L-DOS47 conjugate production because of the differences in optimum pH for the two cross-linking reactions. During production, the antibody is activated with the cross-linker at pH 7.0 then buffer exchanged to pH 6.5 and mixed with urease. The antibody is then linked to urease by increasing the pH of the reaction media to 8.3. Because the reaction rate linking activated AFAIKL2 to urease is very low at pH 6.5, and material uniformity in a large reaction vessel is ensured by premixing at pH 6.5. Therefore, the distribution of residual free urease and the subspecies of urease-$(Ab)_x$ are solely determined by probability and material molar ratios. At conjugation ratios of 8-11 antibodies/urease the residual urease content is theoretically negligible and the L-DOS47 conjugate can be purified using ultradiafiltration to remove unreacted antibody and hydrolyzed cross-linker. Size exclusion chromatograms of L-DOS47 conjugate, free AFAIKL2, and free urease are shown in FIG. 7.

Figure 8:
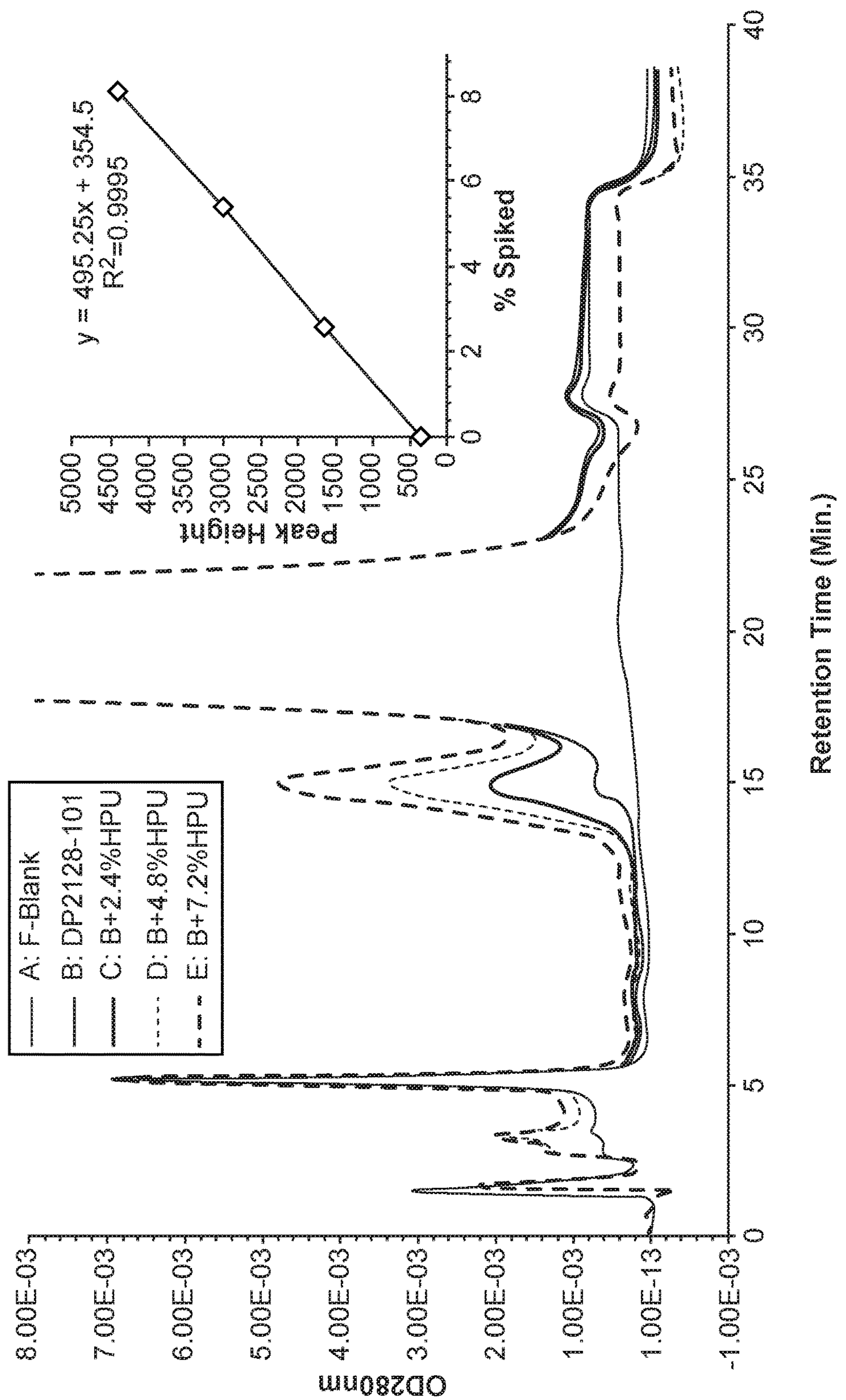
FIG. 8 depicts exemplifying Ion Exchange Chromatograms of formulation blank (A), L-DOS47 (B) and L-DOS47 spiked with 2.4% (C), 4.8% (D) and 7.2% (E) HP urease (HPU). Formulation blank contains 10 mM histidine, 1% (w/v) sucrose, 0.2 mM EDTA, pH 6.8.

The L-DOS47 conjugate elutes at ~24.6 minutes, the dimer (possibly linked by a disulfide bond or by an AFAIKL2 molecule activated with two SIAB) elutes as a small unresolved peak at 20.5 minutes, and the polymer elutes as a trace peak at the void time (~15 minutes). A trace peak at ~40 minutes represents the buffer components. The L-DOS47 conjugate peak width is slightly larger than but comparable to that of free urease, suggesting an evenly distributed conjugation reaction. Free antibody elutes at 37 minutes. A small unresolved peak at the front of the antibody peak represents non-covalent dimer. High purity of the antibody (>95%) is typically observed in the production lots, with its high molecular weight species including dimers not exceeding 5%. HPU typically elutes with a major peak at ~26.9 minutes, a small dimer peak at 24 minutes, and a trace polymer peak at 15 minutes. Purification of crude urease to HPU resulted in ~97% monomer while the sum of dimer and polymer is not more than 3%. Greater than 95% L-DOS47 purity is typically achieved from simple purification using only ultradiafiltration. Because the SEC is run under native conditions, it can determine changes in effective molecular weights due to degradation and dissociation of protein quaternary structures; therefore, this method is also used as a stability indicating assay for L-DOS47. The presence of residual free urease in L-DOS47 was evaluated using ion exchange chromatography (FIG. 8).

The residual free urease elutes at 15.33 minutes, which is very close to the spiked urease peak (15.42 minutes). The HPU peak is fairly well resolved from the large L-DOS47 peak ($R_s$ of 1.48). As shown in the insert of FIG. 8, the standard addition method (L-DOS47 spiked with 2.4%, 4.8% and 7.2% w/w HPU) to determine residual urease content exhibits good linearity ($R^2$ of 0.9995). The calculated residual urease content of this sample is 0.72%, and residual urease has not exceeded 2% in all production lots to date, demonstrating that the residual urease is practically negligible under these conditions and the manufacturing process does not require an additional step to separate the L-DOS47 conjugate from unconjugated urease.

During L-DOS47 production, each of the six monomeric urease subunits can be conjugated with zero, one, two, three, or four AFAIKL2 molecules; therefore, under denaturing conditions SDS-Experion of L-DOS47 produces a pattern of multiple discrete peaks/bands from ~90-155 kDa. Additionally, during the antibody activation reaction, a small portion of the antibody can be randomly activated with two SIAB per antibody molecule (AFAIKL2-$(SIAB)_2$) which results in conjugation of each of those antibody molecules to two subunits of urease. The one-antibody-two-subunits consequently produces a smaller second set of poorly resolved peaks/bands ranging from 200-260 kDa.

Figure 9:
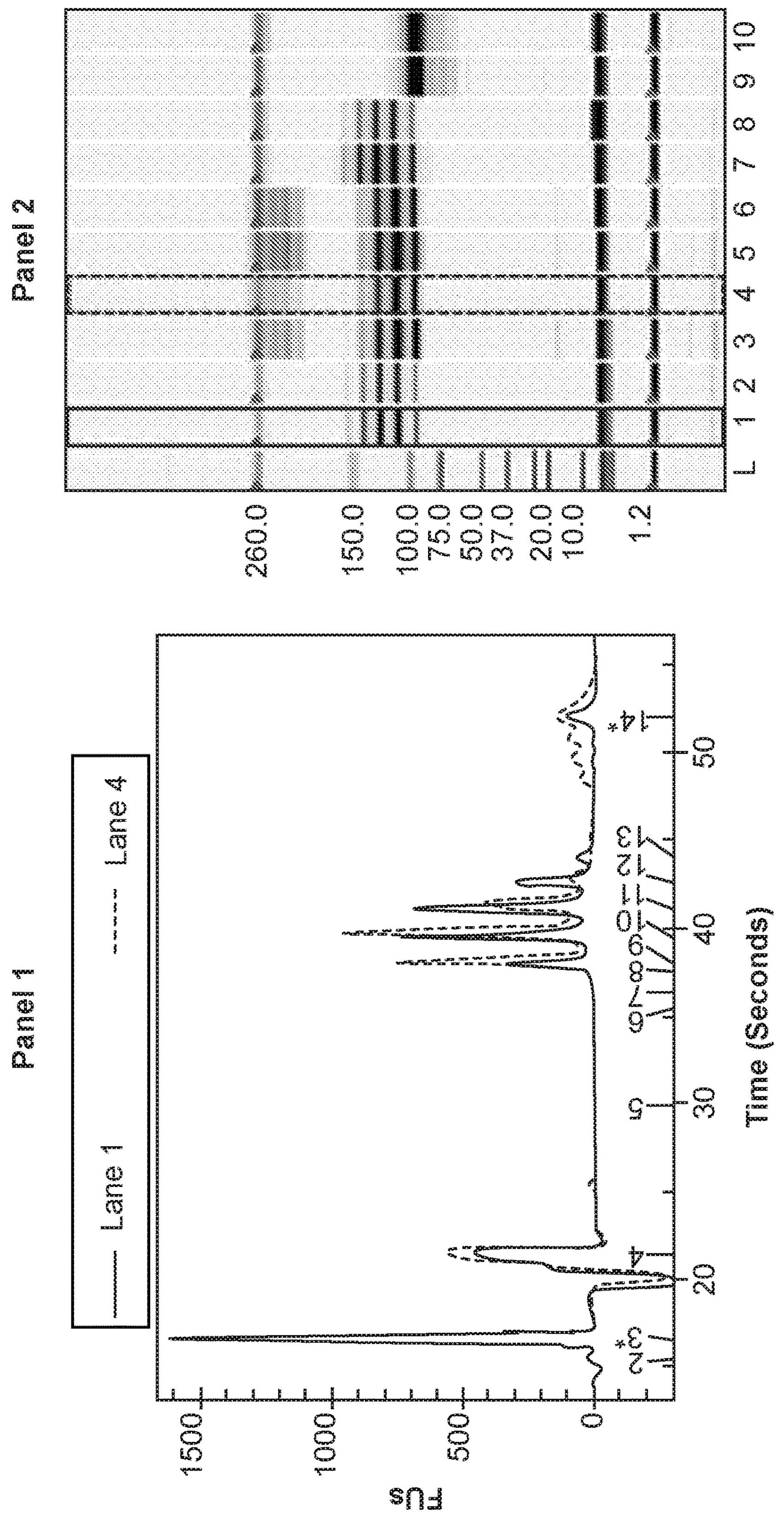
FIG. 9 depicts an exemplifying snapshot of an Experion SDS window. Panel 1: overlay of electropherograms of lanes 2 and 4. Panel 2: Lane L, molecular weight (MW) ladder; Lanes 1, 2, 7 and 8: L-DOS47 produced with activated AFAIKL2 that had undergone additional IEC purification; Lanes 3-6: L-DOS47 produced with AFAIKL2 that had not undergone additional IEC; Lane 9 and 10, HPU. In panel 1, the numbers 2-14 in Panel 1 on the x-axis are the peak numbers of the electropherogram from Lane 1; 3* represents the lowest molecular weight marker peak and 14* the highest MW marker peak for the internal MW standard.

In FIG. 9, Panel 2 depicts a virtual gel image and Panel 1 contains an overlay of the electropherograms from lanes 1 and 4. The L-DOS47 bench scale sample in lanes 1-2 and 7-8 was produced with activated AFAIKL2 that had been purified by ion exchange chromatography before the second reaction of the conjugation. Because the AFAIKL2-$(SIAB)_2$ species was removed, the resulting conjugate lacked the inter-cross-linked subunits and a only single set of peaks/bands was observed. In the L-DOS47 sample in lanes 3-6, the AFAIKL2 had been used directly in conjugation after the activation step without additional purification and consequently the small second set of peaks/bands is present. Lanes 9 and 10 were overloaded with an HPU sample.

Figure 10:
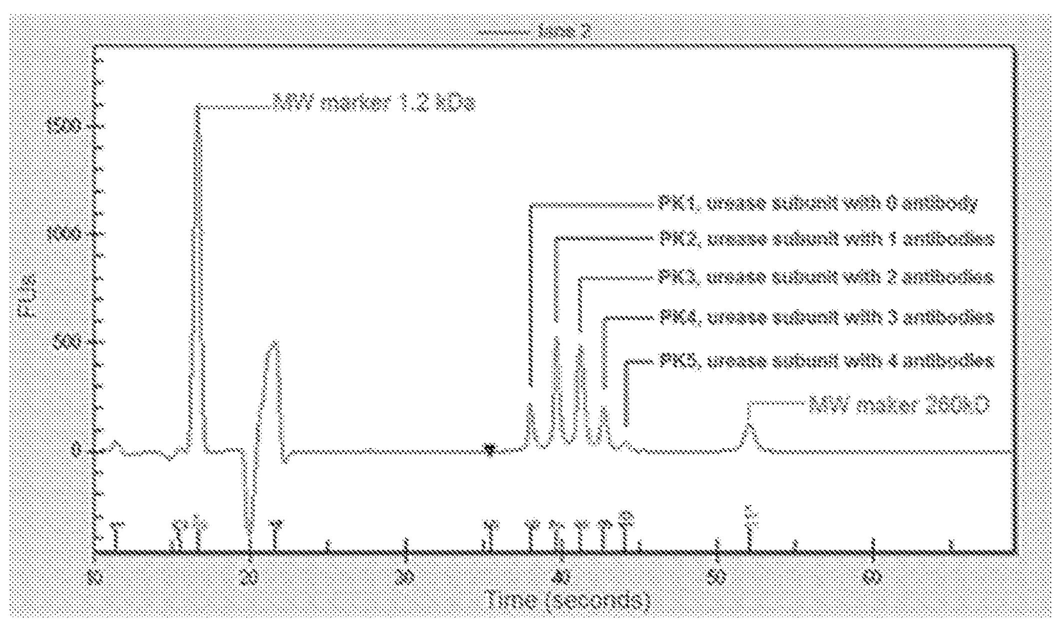
FIG. 10 depicts an exemplifying electropherogram of L-DOS47 (lane 2 from FIG. 9) showing the discrete peaks for urease subunits linked with 0-4 antibody molecules. The numbers 1-11 on the x-axis are the peak numbers; 3* represents the lowest molecular weight marker peak and 11* the highest MW marker peak for the internal MW standard.

The peak areas (FIG. 9, Panel 1) and band intensities (FIG. 9, Panel 2) depend on the relative abundances of urease subunits linked with the corresponding number of antibody molecules. The peak areas are integrated by the software after baseline correction and the L-DOS47 conjugation ratio (CR) is calculated as follows (see FIG. 10, representing lane 2 of the gel from FIG. 9):

$$CR=6*(PK_1*0+PK_2*1+PK_3*2+PK_4*3+PK_5*4)/(PK_1+PK_2+PK_3+PK_4+PK_5)$$

Where $PK_i$ (i=1-5) is the peak area of the urease subunit linked with i−1 antibody molecules.

Because the activated antibody does not undergo ion exchange chromatographic purification during large scale production of L-DOS47, the second poorly resolved set of peaks appears in electropherograms of these samples. However, the two sets of peaks are expected to have similar intensity patterns since the activation site distribution is determined by probability and by the molar ratio of antibody to SIAB. This second set of peaks is therefore not used to calculate conjugation ratios because the bands are poorly resolved and overlap with the 260 kDa molecular weight marker. While the AFAIKL2-$(SIAB)_2$ species could theoretically generate dimer or polymer conjugates by linking to two subunits from different native urease molecules, the minimal levels (less than 3%) of combined dimer and polymer peak areas observed in the size exclusion chromatogram of L-DOS47 sample (FIG. 7) suggest that most of the AFAIKL2-$(SIAB)_2$ species contribute to inter-subunits linkage of a single native urease molecule to produce monomer L-DOS47 and not to inter-molecular linkages to produce dimer and polymer conjugates. In addition, the presence of these dimer and polymer peaks in SEC chromatograms could logically be attributed to disulfide linkages because similar peaks also appeared in size exclusion chromatograms of HP urease. Therefore, the second set of peaks in the electrophoregrams is not employed as a parameter for quality control.

The conjugation ratio of L-DOS47 is critical to its affinity for CEACAM6, the tumor antigen targeted by the antibody.

Figure 11:
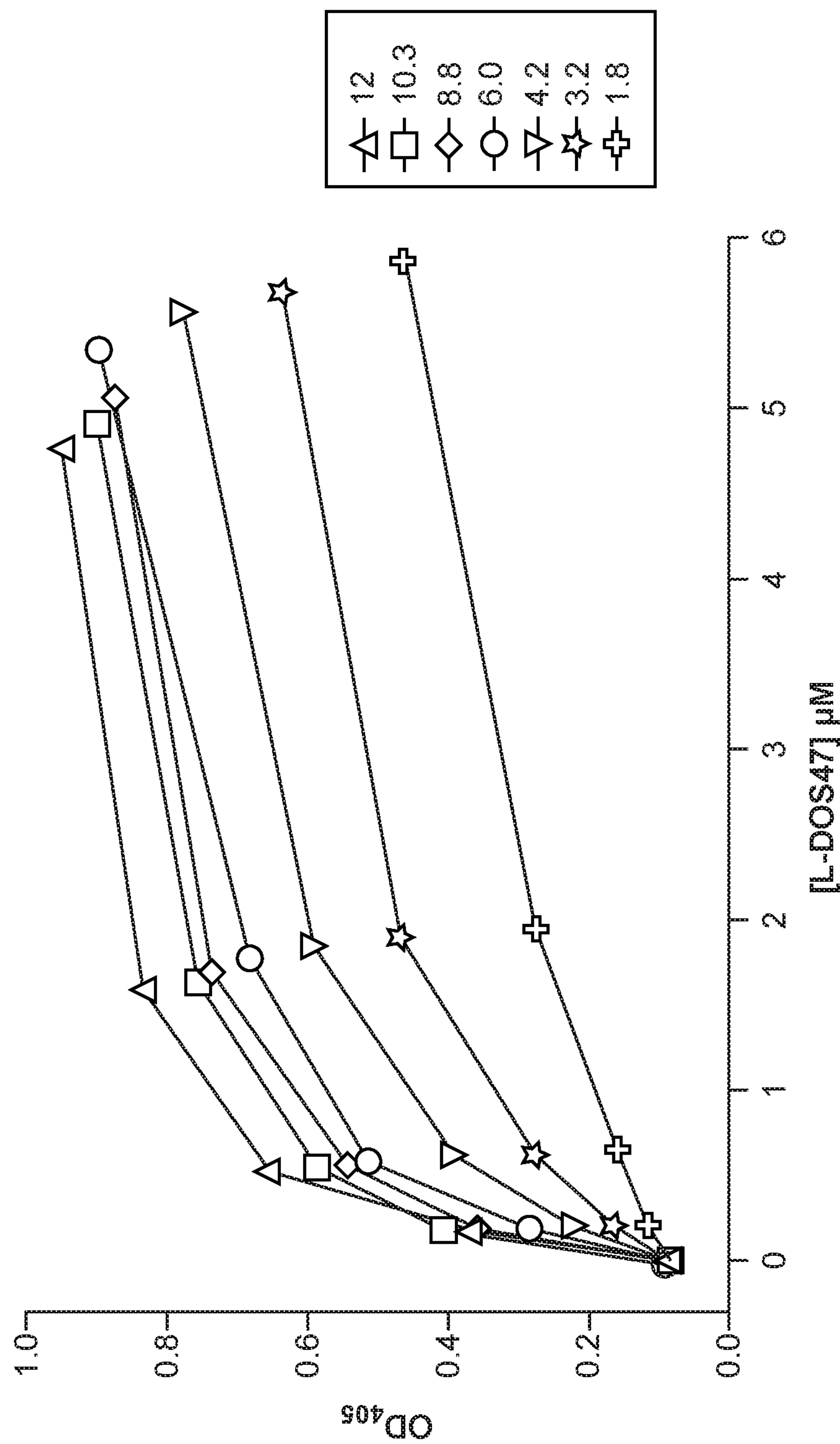
FIG. 11 depicts exemplifying effect of conjugation ratio on the binding activity of L-DOS47. L-DOS47 was prepared with different antibody conjugation ratios (from 1.8 to 12). Direct binding of the L-DOS47 samples to immobilized CEACAM6-A molecules was determined.

L-DOS47 with different conjugation ratios (1.8 to 12 AFAIK per urease) were produced by adjusting the AFAIKL2/HP urease molar ratios to evaluate the effect of conjugation ratio on binding affinity. The binding affinity of L-DOS47 to immobilized CEACAM6-A was found to be directly proportional to the number of antibodies conjugated to urease (FIG. 11). The more antibodies conjugated, the higher the binding signal was observed. However, the effect was less profound at conjugation ratios of 6 or more.

Figure 12:
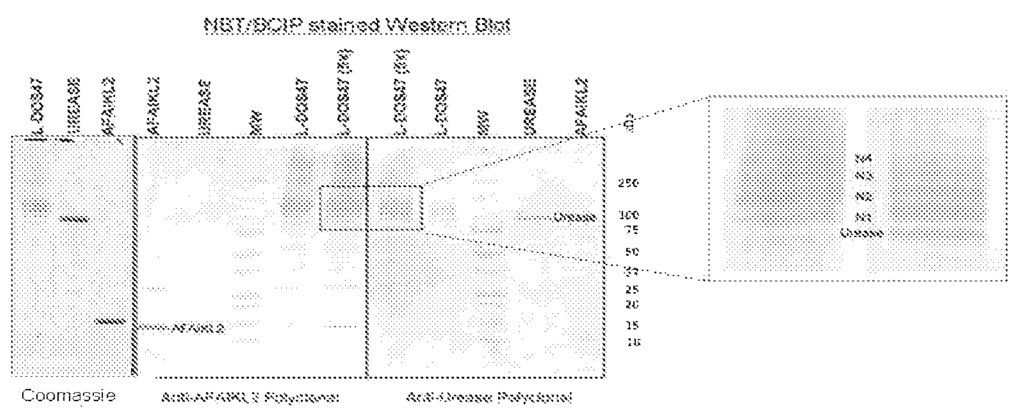
FIG. 12 depicts an exemplifying western blot of AFAIKL2, Urease, and L-DOS47. Left panel: Gel electrophoresis of L-DOS47, urease, and AFAIKL2 (Coomassie blue stained). Middle panel: Western blot of AFAIKL2, urease, and L-DOS47 (standard load and 5× overload)

Analysis of L-DOS47 by dual Western blotting (FIG. 12) confirms the banding pattern seen via SDS-Experion. The inset box shows an enlargement of the boxed region of the main blot in which the urease and conjugated species (N1-N4 corresponding to urease with 1 to 4 conjugated AFAIKL2 respectively) are labeled. When probed with an anti-urease antibody, the 91 kDa urease band is the most strongly visualized and the intensity of the higher molecular weight bands (corresponding to more highly conjugated species) decreases. In contrast, when probed with an anti-AFAIKL2 antibody, the 91 kDa band is barely visible and the next two higher molecular weight bands are most intense (N1 and N2). This is due to the fact that they are the dominant bands in the conjugate. The ability of L-DOS47 to be visualized by both the anti-AFAIKL2 and anti-urease antibodies demonstrates the presence of both species in the conjugate, and the specificity of the antibodies is confirmed by the fact that the anti-AFAIKL2 antibody does not bind to urease and the anti-urease antibody does not bind to AFAIKL2.

Because L-DOS47 is a chemical conjugate of AFAIKL2 and urease, tryptic peptides from both the antibody and the urease enzyme as well as covalently cross-linked peptides of both proteins should be detected from tryptic digests of the conjugate. ESI LC-MS$^E$ peptide mapping was performed to characterize the conjugate. As shown in the associated content, peptides from AFAIKL2 appeared in the L-DOS47 spectrum but not in the HP urease spectrum. From the tryptic digests of L-DOS47, the peptide coverages for both the AFAIKL2 and urease amino acid sequences were 100% with a typical mass error of less than 6 ppm and each of the peptides was confirmed by its high energy MS/MS b/y fragment ions with mass errors of less than ±15 ppm.

To identify the activation sites of AFAIKL2 and to determine the distribution of each conjugation site, AFAIKL2 was activated using SIAB then conjugated to fluorescein labeled cysteine (Cys-FL). After trypsin digestion of the resulting AFAIKL2-Cys-FL and separation by RP-HPLC chromatography, the peak fractions were collected for MALDI-MS to identify the Cys-FL linked antibody tryptic peptides. Because only the SIAB activated sites can be linked to Cys-fluorescein, for which the maximum absorption wavelength in 0.025% TFA is 420 nm, only activated peptide peaks should be detected at 420 nm. For example, if lysine #32 of AFAIKL2 is activated by SIAB, it should be linked to Cys-FL and this tryptic digestion site will be missed during tryptic digestion; therefore, a peak with a molecular mass of 2768.113 Da should be observed which represents the Cys-FL linked lysine-in-middle peptide, (LSCAAHDPIFDK$_{32}$NLMGWG)-Cys-FL (SEQ ID NO: 7), denoted as L2K$_{32}$-Cys-FL. The RP-HPLC chromatogram of a tryptic digest of AFAIKL2-Cys-FL is shown in FIG. 13.

The identified conjugated peptides with detected mass values are also labeled at the corresponding HPLC peaks in FIG. 13. According to the amino acid sequence of the antibody, the primary amines from the six lysine residues and the N-terminal amine are theoretically available for the activation reaction. However, in practice only four of them were substantially activated. This is most likely due to the tertiary structure of the antibody exposing those four primary amines on the surface while burying the others inside the native structure. The distribution of each activation site (Table 4) was calculated according to its peak area and the sum of all the identified HPLC peak areas in FIG. 13.

TABLE 4

HPLC peak area and distribution percentage of each activation site on AFAIKL2

| $Lys_{76}$($L2K_{76}$) | | $Lys_{44}$ ($L2K_{44}$) | | $Met_1$($L2M_1$) | | $Lys_{32}$ ($L2K_{32}$) | |
|---|---|---|---|---|---|---|---|
| Area | % | Area | % | Area | % | Area | % |
| 185 | 35 | 107 | 20 | 140 | 26 | 97 | 18 |

As shown in Table 4, the most active site of the antibody for the cross linker is L2K$_{76}$, followed by L2M$_1$ and then L2K$_{44}$. L2K$_{32}$ is essential for antibody binding and is also the least active site, but still contributed to ~18% of total reactivity. For L-DOS47, the cross-linker activated AFAIKL2 was covalently linked to the cysteine residues exposed on the surface of the urease quaternary structure. Therefore, the covalently cross-linked peptides should be detected from the peptide spectrum of a tryptic digest of L-DOS47.

To identify those covalently cross-linked peptides, ESI LC-MS$^E$ raw data of the tryptic digests from L-DOS47 samples were processed by BiopharmaLynx but searched with a variable-modifier library containing a set of user-created modifiers for all 15 cysteine residues on the urease side. According to the activation distribution in Table 4, those user created modifiers were the three lysine-in-middle peptides plus the linkage portion of SIAB ($C_9H_5O_2N$, 159.0320 Da) (denoted as L2K$_{76}$, L2K$_{44}$ and L2K$_{32}$), and the N-terminal methionine plus the linkage (denoted as L2M$_1$). The results (detail in associated content) demonstrated that among the 15 cysteine residues of each urease subunit, only 6 were substantially conjugated. The most accessible cysteine is UC$_{824}$, followed in order by UC$_{663}$, UC$_{59}$, UC$_{207}$, UC$_{329}$ and UC$_{268}$. Cysteine residue Cys$_{592}$, which is essential to urease enzyme activity, was not substantially conjugated. The relative accessibilities of the four cross-linker activated AFAIKL2 sites to each of the six cysteine residues on the urease side were also different. For example, UC$_{329}$ was only accessible to L2M$_1$. Those substantial conjugation sites were also confirmed by their MS/MS fragment profiles. As an example, the conjugated peptide, L2K$_{32}$UC$_{663}$ whose sequence is (LSCAAHDPIFDKNLMGWGR (SEQ ID NO: 8))-linkage-(CDSSDNDNFR (SEQ ID NO: 9)) and which has a peptide mass of 3517.4873 was identified with a mass match error of 2.1 ppm by searching it as CDSSDNDNFR a urease peptide (SEQ ID NO: 9) modified with (LSCAAHDPIFDKNLMGWGR (SEQ ID NO: 8))-linkage (2346.0674 Da) from the AFAIKL2 side as the modifier. The same peptide was also identified with a mass match error of 2.1 ppm by searching it as LSCAAHDPIFDKNLMGWGR (SEQ ID NO: 8) a AFAIKL2 peptide modified with the linkage-(CDSSDNDNFR (SEQ ID NO: 9)) (1330.4520 Da) from the urease side as the modifier. The high energy collision induced MS/MS spectrum of this conjugated peptide was mapped with 9 b/y fragment ions from the urease side by searching it as a urease peptide modified with the modifier from the AFAIKL2 side. The same spectrum was also mapped with 14 b/y ions from the AFAIKL2 side by searching it as an AFAIKL2 peptide with the modifier from the urease side.

Different L-DOS47 binding profiles were observed among BxPC-3, A549, and MCF7 cell lines (FIG. 14). The results showed that L-DOS47 bound well to the pancreatic cell line BxPC-3, indicating that CEACAM6 antigen was expressed on the cell surface. Moderate binding was observed in the lung cell line A549, but no binding was found in the breast cell line MCF7. The AFAIKL2 antibody, when conjugated to the urease enzyme (DOS47), provided specific targeting towards CEACAM6-expressing cells. This was confirmed by the absence of binding signal in the three cell lines treated with the unconjugated DOS47 control.

BxPC-3 cells were very susceptible to L-DOS47 cytotoxicity (FIG. 15), as shown by the rapid drop in cell survival observed when the cells were treated with less than 1 μg/mL of L-DOS47. Moderate cytotoxicity was observed in A549 cells, while no effects were observed in MCF7, consistent with the results of the binding study. In addition, the negative control DOS47 had no cytotoxic effect on any of the cell lines.

Procedures developed for the conjugation and purification of the L-DOS47 immunoconjugate were successfully employed in its large-scale production. Using the established conjugation chemistry and reaction conditions, good uniformity was achieved by pre-mixing the cross-linker activated antibody with the HP urease intermediate then adjusting the pH to activate the conjugation reaction. At conjugation ratios of 8-11 antibodies per urease molecule, the residual urease content was practically negligible and the L-DOS47 conjugate could be purified using only ultradiafiltration to remove unreacted antibody and hydrolyzed cross-linker and a challenging step to separate residual urease from the final immunoconjugate was avoided. This procedure yielded a high purity L-DOS47 product (>95%) with free urease at less than 2%. The binding affinity of L-DOS47 to immobilized CEACAM6-A as evaluated by ELISA was directly proportional to the number of antibodies conjugated to urease, and leveled off when the conjugation ratio was greater than 6. Conjugation ratios have ranged from 9 to 11 antibodies per urease molecule for all large-scale batches, demonstrating that optimum conjugation had been achieved under these conditions. The dual antibody Western Blot assay confirmed the chemical identity of the conjugate. ESI LC-$MS^E$ peptide mapping analysis achieved 100% sequence recoveries for both the antibody and urease from the L-DOS47 immunoconjugate. Peptide sequences with more than 3 amino acid residues including the C-terminal and N-terminal sequences of both AFAIKL2 and urease were confirmed by MS/MS b/y fragment maps of the corresponding peptides. Effective conjugation sites (4 at the AFAIKL2 side and 6 at the urease side) were identified by ESI LC-$MS^E$ peptide mapping analysis of L-DOS47 samples. Those cross-linked peptides were confirmed by MS/MS b/y fragment maps of the related peptides from both the antibody and the urease sides.

The specificity of L-DOS47 towards the two CEACAM6-expressing cell lines BxPC-3 and A549 was illustrated by the absence of binding and cytotoxic activities of DOS47 versus the antibody-conjugated L-DOS47 counterpart. Among the three cell lines tested, BxPC-3 showed the strongest binding signal whereas A549 only demonstrated moderate binding. The binding signal of BxPC-3 was about five times of that of A549. The results were consistent with those observed in the cytotoxicity assays. L-DOS47 induced a much higher cytotoxic effect on BxPC-3 than A549. No cytotoxic response was observed in MCF-7 due to the lack of L-DOS47 binding. L-DOS47 is being investigated as a potential therapeutic agent in human Phase I clinical studies for non-small cell lung cancer.

It is to be understood that while the present disclosure has been described in conjunction with the above aspects, that the foregoing description and examples are intended to illustrate and not limit the scope of the present disclosure. Other aspects, advantages and modifications within the scope of the present disclosure will be apparent to those skilled in the art to which the present disclosure pertains.

The present disclosure is not to be limited in scope by the specific aspects described which are intended as single illustrations of individual aspects of the present disclosure, and any compositions or methods, which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

REFERENCES

1. Stubbs M, McSheehy P M J, Griffiths J R, et al. Causes and consequences of tumor acidity and implications for treatment. Mol Med Today 2000; 6:15-9.
2. Raghunand N, Gillies R J. pH and Chemotherapy. In: Goode J A, Chadwick D J, eds. The tumor microenvironment: causes and consequences of hypoxia and acidity. Chichester: John Wiley & Sons Ltd. 2001; 199-211.
3. Schornack P A, Gillies R J. Contributions of cell metabolism and $H^+$ diffusion to the acidic pH of tumors. Neoplasia 2003; 5:135-45.
4. Helmlinger G, Sckell A, Dellian M, et al. Acid production in glycolysis-impaired tumors provides new insights into tumor metabolism. Clin Cancer Res 2002; 8:1284-91.
5. Izumi H, Torigoe T, Ishiguchi H, et al. Cellular pH regulators: potentially promising molecular targets for cancer chemotherapy 2003; 29:541-9.
6. Robey I F, Baggett B K, Kirkpatrick N D, et al. Bicarbonate increases tumor pH and inhibits spontaneous metastases. Cancer Res 2009; 69:2260-8.
7. Mahoney B P, Raghunand N, Baggett B, et al. Tumor acidity, ion trapping and chemotherapeutics I. Acid pH affects the distribution of chemotherapeutic agents in vitro. Biochem Pharmacol 2003; 66:1207-18.
8. Wong W Y, DeLuca C I, Tian B, et al. Urease-induced alkalinization of extracellular pH and its antitumor activity in human breast and lung cancers. J Exp Ther Oncol 2005; 5:93-9.
9. Teicher B A, Chari R V J. Antibody conjugate therapeutics: Challenges and potential. Clin Cancer Res 2011; 17:6389-97.
10. Xu G, McLeod H L. Strategies for enzyme/prodrug cancer therapy. Clin Cancer Res 2001; 7:3314-24.
11. Kuespert Kl, Pils S, Hauck C R. CEACAMs: their role in physiology and pathophysiology. Curr Opin Cell Biol 2006; 18:565-71.

12. Pavlopoulou A, Scorilas A. A comprehensive phylogenetic and structural analysis of the carcinoembryonic antigen (CEA) gene family. Genome Biol Evol 2014; 6:1314-26.
13. Blumenthal R D, Hansen H J, Goldenberg D M. Inhibition of adhesion, invasion, and metastasis by antibodies targeting CEACAM6 (NCA-90) and CEACAM5 (carcinoembryonic antigen). Cancer Res 2005; 65:8809-17.
14. Baral T N, Murad Y, Nguyen T D, et al. Isolation of functional single domain antibody by whole cell immunization: implications for cancer treatment. J Immunol Methods 2011; 371:70-80.
15. Strickland L A, Ross J, Williams S, et al. Preclinical evaluation of carcinoembryonic cell adhesion molecule (CEACAM) 6 as potential therapy target for pancreatic adenocarcinoma. J Pathol 2009; 218:380-390.
16. Duxbury M S, Matros E, Ito H, et al. Systemic siRNA-mediated gene silencing: A new approach to targeted therapy of cancer. Annals of Surgery 2004; 240:667-76.
17. Zhang J, Li Q, Nguyen T D, et al. A pentavalent single-domain antibody approach to tumor antigen discovery and the development of novel proteomics reagents. J Mol Biol 2004; 341:161-9.
18. Weatherburn M W. Phenol-hypochlorite reaction for determination of ammonia. Anal Chem 1967; 39:971-4.
19. Ohwada A, Yoshioka Y, Iwabuchi K, et al. VEGF regulates the proliferation of acid-exposed alveolar lining epithelial cells. Thorax 2003; 58:328-32.
20. Napier, M. P. et al., (2000) Antibody-directed Enzyme Prodrug Therapy: Efficacy and Mechanism of Action in Colorectal Carcinomal. *Clinical Cancer Research* 6, 765-772.
21. Bagshawe, K. D. (1987) Antibody directed enzymes revive anti-cancer prodrugs concept. *Br. J. Cancer* 56, 531-532.
22. Bagshawe K. D. (2006) Antibody-directed enzyme prodrug therapy (ADEPT) of cancer. *Expert Rev Anticancer Ther* 6, 1421-1431.
23. Tietze, L. F. and Feuerstein, T. (2003) Enzyme and Proton-Activated Prodrugs for a Selective Cancer Therapy. *Curr. Pharm. Des.* 9, 2155-2175.
24. Denny, W. A. (2004) Tumor-activated Prodrugs—A New Approach to Cancer Therapy. *Cancer Invest.* 22, 604-619.
25. Pasquetto M. V., Vecchia, L., Covini, D., Digilio, R., and Scotti, C., (2011) Targeted Drug Delivery Using Immunoconjugates: Principles and Applications *Journal of Immunother* 34, 611-628.
26. Tietze, L. F., and Krewer, B. (2009) Antibody-directed enzyme prodrug therapy: a promising approach for a selective treatment of cancer based on prodrugs and monoclonal antibodies. *Chem Biol Drug Des* 74, 205-211.
27. Afshar, S., Asai. T., and Morrison, S. L. (2009) Humanized ADEPT Comprised of an Engineered Human Purine Nucleoside Phosphorylase and a Tumor Targeting Peptide for Treatment of Cancer. *Mol Cancer Ther* 2009, 8 1-9.
28. Afshar, S., Olafsen, T., Wu A. M., and Morrison, S. L., (2009) Characterization of an engineered human purine nucleoside phosphorylase fused to an anti-her2/neu single chain Fv for use in ADEPT. *J Exp Clin Cancer Res* 28:147.
29. Alderson R. A., Toki, B. e., Roberge, M., Geng, W., Basler, J., Chin, R., Liu, A., Ueda, R., Hodges, D., Escandon, E., Chen, T., Kanavarioti, T., Babé, L., Senter, P. D., Fox, J. A., Schellenberger, V., (2006) Characterization of a CC49-Based Single-Chain Fragment-$\hat{\alpha}$-Lactamase Fusion Protein for Antibody-Directed Enzyme Prodrug Therapy (ADEPT). Bioconjugate Chem, 17, 410-418.
30. http://www.piercenet.com/method/crosslinking-applications
31. Kim, J. H., Kim, Y-W., Kim, I-W., Park, D. C., Kim, Y. W., Lee, K-H., Jang, C. K., Ahn, W. S., (2013) Identification of candidate biomarkers using the Experion™ automated electrophoresis system in serum samples from ovarian cancer patients. *International Journal of Oncology* 42940, 1257-1262.
32. Chan, O. T. M., and Herold, D. A., (2009) Chip Electrophoresis as a Method for Quantifying Total Albumin in Cerebrospinal Fluid. *Journal of the Association for Laboratory Automation* 14, 6-11.
33. Zhang, J., Li, Q., Nguyen, T. D., Tremblay, T-L., Stone, E., To, R., Kelly, J., and MacKenzie, C. R., (2004) A pentavalent single-domain antibody approach to tumor antigen discovery and the development of novel proteomics reagents. *J Mol Biol* 41 161-1699.
34. Wong, W. Y., DeLuca, C. I., Tian, B., Wilson, I., Molund, S., Warriar, N., Govindan, M. V., Sega, 1 D., and Chao, H., (2005) Urease-induced alkalinization of extracellular pH and its antitumor activity in human breast and lung cancers. *J Exp Ther Oncol* 5, 93-9.

What is claimed is:

1. A pharmaceutical composition comprising:

a pharmaceutically acceptable aqueous solution suitable for intravenous injection, and a single domain antibody-urease conjugate, wherein the conjugate has a conjugation ratio of 3, 4, 5, 6, 7, 8, 9, 10, 11, or 12 single domain antibody moieties per urease moiety, the single domain antibody having binding specificity to CEACAM6 and an amino acid sequence of SEQ ID NO: 1 or an amino acid sequence with at least 95% sequence identity with SEQ ID NO: 1, wherein the conjugate has urease activity;

wherein said composition is substantially free of unconjugated urease.

2. The pharmaceutical composition of claim 1, wherein the unconjugated urease is less than 5%.

3. The pharmaceutical composition of claim 1, which is free of non-aqueous HPLC solvents.

4. The pharmaceutical composition of claim 1, wherein the pH is about 6.8.

5. The pharmaceutical composition of claim 1, wherein the conjugate has a conjugation ratio of 6, 7, 8, 9, 10, 11, or 12 single domain antibody moieties per urease moiety.

6. The pharmaceutical composition of claim 5, wherein the conjugate has a conjugation ratio of 8, 9, 10, 11, or 12 single domain antibody moieties per urease moiety.

7. The pharmaceutical composition of claim 1, wherein the conjugate has an average conjugation ratio of about 6 or more single domain antibody moieties per urease moiety.

8. The pharmaceutical composition of claim 1, wherein the conjugate has an average conjugation ratio of about 8-11 single domain antibody moieties per urease moiety.

9. The pharmaceutical composition of claim 1, wherein the urease is a Jack bean urease.

10. The pharmaceutical composition of claim 1, wherein the single domain antibody is a humanized or non-human antibody.

11. The pharmaceutical composition of claim 1, wherein the single domain antibody has a binding affinity to CEACAM6 with a $K_d$ value of higher than about $1\times10^{-6}$ M.

12. The pharmaceutical composition of claim 11, wherein the conjugate has a binding affinity to CEACAM6 with a $K_d$ value of no more than about $1\times10^{-8}$ M.

13. The pharmaceutical composition of claim 12, wherein the conjugate has a binding affinity to CEACAM6 with a $K_d$ value of no more than about $1\times10^{-10}$ M.

14. The pharmaceutical composition of claim 1, wherein the conjugate has a binding affinity to CEACAM6 with an $IC_{50}$ value of no more than about 5 nM.

15. The pharmaceutical composition of claim 14, wherein the $IC_{50}$ value is about 3.22 nM.

16. The pharmaceutical composition of claim 1, wherein the conjugate binds to CEACAM6 with an 1050 value of about 20 μg/mL.

17. The pharmaceutical composition of claim 1, wherein the single domain antibody comprises the amino acid sequence of SEQ ID NO: 1.

18. A method of treating cancer in a subject, comprising administering to the subject a therapeutically effective amount of the composition of claim 1, thereby treating cancer in the subject.

19. The method of claim 18, wherein the cancer is one or more of non-small cell lung carcinoma, breast, pancreatic, ovarian, lung, colon cancer, or a combination thereof.

20. The method of claim 19, wherein the cancer is non-small cell lung carcinoma.

21. The method of claim 19, wherein the subject is a human.

22. The pharmaceutical composition of claim 1, wherein the composition is lyophilized.

23. The pharmaceutical composition of claim 1, wherein the composition comprises up to about 2.0 mg/mL conjugate.

24. A pharmaceutical composition comprising:

a single domain antibody-urease conjugate having a conjugation ratio of 3, 4, 5, 6, 7, 8, 9, 10, 11, or 12 single domain antibody moieties per urease moiety, wherein each of said single domain antibodies is specific for binding to CEACAM6 and is represented by an amino acid sequence of SEQ ID NO: 1 or an amino acid sequence sharing at least 95% sequence identity with SEQ ID NO: 1 that maintains binding specificity to CEACAM6, wherein the conjugate has urease activity; and less than 5% unconjugated urease.

25. The pharmaceutical composition of claim 24, wherein the conjugate has 6 to 12 single domain antibody moieties conjugated per urease moiety.

26. A pharmaceutical aqueous composition for intravenous injection into a subject for treatment of a CEACAM6 expressing tumor, the composition comprising:

a single domain antibody-urease conjugate comprising 6 to 12 single domain antibody moieties per urease moiety, the single domain antibody having an amino acid sequence of SEQ ID NO: 1 that specifically binds to CEACAM6 or an amino acid sequence sharing at least 95% sequence identity with SEQ ID NO: 1 that maintains binding specificity to said CEACAM6, wherein the conjugate has urease activity, wherein said single domain antibody-urease conjugate has a binding specificity to CEACAM6 about 500 times or higher than an un-conjugated single domain antibody of amino acid SEQ ID NO: 1, and wherein said composition is substantially free of unconjugated urease.

* * * * *

SEQUENCE LISTING

```
<160> NUMBER OF SEQ ID NOS: 9

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Val Gln Leu Gln Ala Ser Gly Gly Gly Val Val Gln Pro Gly
1               5                   10                  15

Gly Ser Leu Arg Leu Ser Cys Ala Ala His Asp Pro Ile Phe Asp Lys
            20                  25                  30

Asn Leu Met Gly Trp Gly Arg Gln Ala Pro Gly Lys Gln Arg Glu Tyr
        35                  40                  45
```

```
Val Ala Thr Ile Ser Gly Ser Gly Gly Thr Asn Tyr Ala Ser Ser Val
    50                  55                  60

Glu Gly Arg Phe Thr Ile Ser Arg Asp Asn Ala Lys Lys Thr Val Tyr
65                  70                  75                  80

Leu Gln Met Asn Asp Leu Lys Pro Glu Asp Thr Ala Val Tyr Tyr Cys
                85                  90                  95

Asn Ser Ala Phe Ala Ile Trp Gly Gln Gly Thr Gln Val Thr Val Ser
            100                 105                 110

Ser Gly Gly Gly Glu Glu Asp Asp Gly Lys
        115                 120


<210> SEQ ID NO 2
<211> LENGTH: 840
<212> TYPE: PRT
<213> ORGANISM: Canavalia ensiformis

<400> SEQUENCE: 2

Met Lys Leu Ser Pro Arg Glu Val Glu Lys Leu Gly Leu His Asn Ala
1               5                   10                  15

Gly Tyr Leu Ala Gln Lys Arg Leu Ala Arg Gly Val Arg Leu Asn Tyr
            20                  25                  30

Thr Glu Ala Val Ala Leu Ile Ala Ser Gln Ile Met Glu Tyr Ala Arg
        35                  40                  45

Asp Gly Glu Lys Thr Val Ala Gln Leu Met Cys Leu Gly Gln His Leu
    50                  55                  60

Leu Gly Arg Arg Gln Val Leu Pro Ala Val Pro His Leu Leu Asn Ala
65                  70                  75                  80

Val Gln Val Glu Ala Thr Phe Pro Asp Gly Thr Lys Leu Val Thr Val
                85                  90                  95

His Asp Pro Ile Ser Arg Glu Asn Gly Glu Leu Gln Glu Ala Leu Phe
            100                 105                 110

Gly Ser Leu Leu Pro Val Pro Ser Leu Asp Lys Phe Ala Glu Thr Lys
        115                 120                 125

Glu Asp Asn Arg Ile Pro Gly Glu Ile Leu Cys Glu Asp Glu Cys Leu
    130                 135                 140

Thr Leu Asn Ile Gly Arg Lys Ala Val Ile Leu Lys Val Thr Ser Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Thr Ala Val Arg Phe Glu Pro Gly Asp Cys Lys
        195                 200                 205

Ser Val Thr Leu Val Ser Ile Glu Gly Asn Lys Val Ile Arg Gly Gly
    210                 215                 220

Asn Ala Ile Ala Asp Gly Pro Val Asn Glu Thr Asn Leu Glu Ala Ala
225                 230                 235                 240

Met His Ala Val Arg Ser Lys Gly Phe Gly His Glu Glu Glu Lys Asp
                245                 250                 255

Ala Ser Glu Gly Phe Thr Lys Glu Asp Pro Asn Cys Pro Phe Asn Thr
            260                 265                 270

Phe Ile His Arg Lys Glu Tyr Ala Asn Lys Tyr Gly Pro Thr Thr Gly
        275                 280                 285

Asp Lys Ile Arg Leu Gly Asp Thr Asn Leu Leu Ala Glu Ile Glu Lys
    290                 295                 300
```

```
Asp Tyr Ala Leu Tyr Gly Asp Glu Cys Val Phe Gly Gly Gly Lys Val
305                 310                 315                 320

Ile Arg Asp Gly Met Gly Gln Ser Cys Gly His Pro Pro Ala Ile Ser
                325                 330                 335

Leu Asp Thr Val Ile Thr Asn Ala Val Ile Ile Asp Tyr Thr Gly Ile
            340                 345                 350

Ile Lys Ala Asp Ile Gly Ile Lys Asp Gly Leu Ile Ala Ser Ile Gly
        355                 360                 365

Lys Ala Gly Asn Pro Asp Ile Met Asn Gly Val Phe Ser Asn Met Ile
    370                 375                 380

Ile Gly Ala Asn Thr Glu Val Ile Ala Gly Glu Gly Leu Ile Val Thr
385                 390                 395                 400

Ala Gly Ala Ile Asp Cys His Val His Tyr Ile Cys Pro Gln Leu Val
                405                 410                 415

Tyr Glu Ala Ile Ser Ser Gly Ile Thr Thr Leu Val Gly Gly Gly Thr
            420                 425                 430

Gly Pro Ala Ala Gly Thr Arg Ala Thr Thr Cys Thr Pro Ser Pro Thr
        435                 440                 445

Gln Met Arg Leu Met Leu Gln Ser Thr Asp Asp Leu Pro Leu Asn Phe
    450                 455                 460

Gly Phe Thr Gly Lys Gly Ser Ser Ser Lys Pro Asp Glu Leu His Glu
465                 470                 475                 480

Ile Ile Lys Ala Gly Ala Met Gly Leu Lys Leu His Glu Asp Trp Gly
                485                 490                 495

Ser Thr Pro Ala Ala Ile Asp Asn Cys Leu Thr Ile Ala Glu His His
            500                 505                 510

Asp Ile Gln Ile Asn Ile His Thr Asp Thr Leu Asn Glu Ala Gly Phe
        515                 520                 525

Val Glu His Ser Ile Ala Ala Phe Lys Gly Arg Thr Ile His Thr Tyr
    530                 535                 540

His Ser Glu Gly Ala Gly Gly Gly His Ala Pro Asp Ile Ile Lys Val
545                 550                 555                 560

Cys Gly Ile Lys Asn Val Leu Pro Ser Ser Thr Asn Pro Thr Arg Pro
                565                 570                 575

Leu Thr Ser Asn Thr Ile Asp Glu His Leu Asp Met Leu Met Val Cys
            580                 585                 590

His His Leu Asp Arg Glu Ile Pro Glu Asp Leu Ala Phe Ala His Ser
        595                 600                 605

Arg Ile Arg Lys Lys Thr Ile Ala Ala Glu Asp Val Leu Asn Asp Ile
    610                 615                 620

Gly Ala Ile Ser Ile Ile Ser Ser Asp Ser Gln Ala Met Gly Arg Val
625                 630                 635                 640

Gly Glu Val Ile Ser Arg Thr Trp Gln Thr Ala Asp Lys Met Lys Ala
                645                 650                 655

Gln Thr Gly Pro Leu Lys Cys Asp Ser Ser Asp Asn Asp Asn Phe Arg
            660                 665                 670

Ile Arg Arg Tyr Ile Ala Lys Tyr Thr Ile Asn Pro Ala Ile Ala Asn
        675                 680                 685

Gly Phe Ser Gln Tyr Val Gly Ser Val Glu Val Gly Lys Leu Ala Asp
    690                 695                 700

Leu Val Met Trp Lys Pro Ser Phe Phe Gly Thr Lys Pro Glu Met Val
705                 710                 715                 720
```

```
Ile Lys Gly Gly Met Val Ala Trp Ala Asp Ile Gly Asp Pro Asn Ala
                725                 730                 735

Ser Ile Pro Thr Pro Glu Pro Val Lys Met Arg Pro Met Tyr Gly Thr
            740                 745                 750

Leu Gly Lys Ala Gly Gly Ala Leu Ser Ile Ala Phe Val Ser Lys Ala
        755                 760                 765

Ala Leu Asp Gln Arg Val Asn Val Leu Tyr Gly Leu Asn Lys Arg Val
    770                 775                 780

Glu Ala Val Ser Asn Val Arg Lys Leu Thr Lys Leu Asp Met Lys Leu
785                 790                 795                 800

Asn Asp Ala Leu Pro Glu Ile Thr Val Asp Pro Glu Ser Tyr Thr Val
                805                 810                 815

Lys Ala Asp Gly Lys Leu Leu Cys Val Ser Glu Ala Thr Thr Val Pro
            820                 825                 830

Leu Ser Arg Asn Tyr Phe Leu Phe
        835                 840


<210> SEQ ID NO 3
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ile Gln Asn Pro Ala Ser Ala Asn Arg Ser Asp Pro Val Thr Leu Asn
1               5                   10                  15

Val Leu Tyr Gly Pro Asp Gly Pro Thr Ile Ser Pro Ser Lys Ala Asn
            20                  25                  30

Tyr Arg Pro Gly Glu Asn Leu Asn Leu Ser Cys His Ala Ala Ser Asn
        35                  40                  45

Pro Pro
    50


<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ile Gln Asn Pro Ala Ser Ala Asn Arg Ser Asp
1               5                   10


<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

aaggcgaaag agtggatggc aacagtcta                                        29


<210> SEQ ID NO 6
<211> LENGTH: 29
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 6

aagaagcaac cggacagttc catgtatac                                      29


<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Ser Cys Ala Ala His Asp Pro Ile Phe Asp Lys Asn Leu Met Gly
1               5                   10                  15

Trp Gly Cys


<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ser Cys Ala Ala His Asp Pro Ile Phe Asp Lys Asn Leu Met Gly
1               5                   10                  15

Trp Gly Arg


<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Asp Ser Ser Asp Asn Asp Asn Phe Arg
1               5                   10
```